(12) United States Patent
Li et al.

(10) Patent No.: US 11,692,229 B2
(45) Date of Patent: *Jul. 4, 2023

(54) FAST DIAGNOSIS AND PERSONALIZED TREATMENTS FOR ACNE

(71) Applicant: The Regents of the University of California, Oakland, CA (US)

(72) Inventors: Huiying Li, Los Angeles, CA (US); Shuta Tomida, Santa Monica, CA (US); Robert L. Modlin, Sherman Oaks, CA (US); Jeffery F. Miller, Santa Monica, CA (US); Sorel T. Fitz-Gibbon, Los Angeles, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/033,034

(22) Filed: Sep. 25, 2020

(65) Prior Publication Data
US 2021/0123092 A1 Apr. 29, 2021

Related U.S. Application Data

(60) Continuation of application No. 16/390,575, filed on Apr. 22, 2019, now abandoned, which is a
(Continued)

(51) Int. Cl.
*C12Q 1/689* (2018.01)
*C12Q 1/6883* (2018.01)
(Continued)

(52) U.S. Cl.
CPC ............ *C12Q 1/689* (2013.01); *A61K 35/741* (2013.01); *A61K 35/76* (2013.01);
(Continued)

(58) Field of Classification Search
CPC .. C12Q 1/689; C12Q 1/6883; C12Q 2600/16; C12Q 1/701; C12Q 2600/112;
(Continued)

(56) References Cited

U.S. PATENT DOCUMENTS

| 5,643,584 A | 7/1997 | Farng et al. |
| 5,836,999 A | 11/1998 | Eckhouse et al. |

(Continued)

FOREIGN PATENT DOCUMENTS

| EP | 0914778 A1 | 5/1999 |
| WO | WO-01/81581 A2 | 11/2001 |

(Continued)

OTHER PUBLICATIONS

"Propionibacterium acnes gene for 16S ribosomal RNA, complete sequence," NCBI Database Accession No. AB097215 (2002).

(Continued)

*Primary Examiner* — Jana A Hines
(74) *Attorney, Agent, or Firm* — Foley Hoag LLP; David P. Halstead; Allison L. Gilder

(57) ABSTRACT

Methods of diagnosing and treating patients afflicted with acne, including diagnosing one as having acne if the individual possesses RT4, RT5, RT7, RT8, RT9, or RT10. Methods for treating acne include administering an effective amount of a drug specifically targeting RT4, RT5, RT7, RT8, RT9, or RT10, such as small molecules, antisense molecules, siRNAs, biologics, antibodies, phages, vaccines, or combination thereof.

8 Claims, 39 Drawing Sheets

Specification includes a Sequence Listing.

Related U.S. Application Data continuation of application No. 15/257,423, filed on Sep. 6, 2016, now Pat. No. 10,364,473, which is a division of application No. 14/385,576, filed as application No. PCT/US2013/032551 on Mar. 15, 2013, now abandoned.

(60) Provisional application No. 61/612,290, filed on Mar. 17, 2012.

(51) Int. Cl.
| | | |
|---|---|---|
| A61K 39/05 | (2006.01) | |
| A61K 35/741 | (2015.01) | |
| A61K 35/76 | (2015.01) | |
| A61K 39/02 | (2006.01) | |
| C12N 7/00 | (2006.01) | |
| C12Q 1/70 | (2006.01) | |

(52) U.S. Cl.
CPC .......... *A61K 39/0208* (2013.01); *A61K 39/05* (2013.01); *C12N 7/00* (2013.01); *C12Q 1/6883* (2013.01); *C12Q 1/701* (2013.01); *C12N 2795/00032* (2013.01); *C12Q 2600/112* (2013.01); *C12Q 2600/156* (2013.01); *C12Q 2600/16* (2013.01)

(58) Field of Classification Search
CPC .................. C12Q 2600/156; A61K 39/05; A61K 35/741; A61K 35/76; A61K 39/0208; C12N 2795/00032
See application file for complete search history.

(56) References Cited

U.S. PATENT DOCUMENTS

| | | | |
|---|---|---|---|
| 6,121,036 | A | 9/2000 | Ghanbari et al. |
| 6,726,913 | B1 | 4/2004 | Van Kampen et al. |
| 7,005,257 | B1 | 2/2006 | Haas et al. |
| 7,867,711 | B2 | 1/2011 | Yoshii et al. |
| 8,529,892 | B2 | 9/2013 | Blaser et al. |
| 8,906,668 | B2 | 12/2014 | Henn et al. |
| 9,011,834 | B1 | 4/2015 | McKenzie et al. |
| 9,011,885 | B2 | 4/2015 | Saurat |
| 9,028,841 | B2 | 5/2015 | Henn et al. |
| 9,180,147 | B2 | 11/2015 | McKenzie et al. |
| 9,446,080 | B2 | 9/2016 | McKenzie et al. |
| 9,533,014 | B2 | 1/2017 | Henn et al. |
| 9,737,592 | B1 | 8/2017 | Bermudes et al. |
| 9,889,165 | B2 | 2/2018 | Taylor et al. |
| 10,293,007 | B2* | 5/2019 | Taylor .................... A61P 17/00 |
| 10,364,473 | B2* | 7/2019 | Li .......................... C12Q 1/701 |
| 2004/0157837 | A1 | 8/2004 | Serbedzija et al. |
| 2006/0121015 | A1 | 6/2006 | Collins et al. |
| 2009/0035329 | A1 | 2/2009 | Blaser et al. |
| 2010/0226890 | A1 | 9/2010 | Holland et al. |
| 2013/0224745 | A1 | 8/2013 | Hogan et al. |
| 2014/0044677 | A1 | 2/2014 | Qvit-Raz et al. |
| 2014/0147425 | A1 | 5/2014 | Henn et al. |
| 2014/0199281 | A1 | 7/2014 | Henn et al. |
| 2015/0005373 | A1 | 1/2015 | Saurat |
| 2015/0086581 | A1 | 3/2015 | Li et al. |
| 2015/0094351 | A1 | 4/2015 | Saurat |
| 2015/0152486 | A1 | 6/2015 | Mouyna et al. |
| 2015/0190435 | A1 | 7/2015 | Henn et al. |
| 2015/0361436 | A1 | 12/2015 | Hitchcock et al. |
| 2016/0074505 | A1 | 3/2016 | Kovarik et al. |
| 2017/0042856 | A1 | 2/2017 | Saurat |
| 2017/0058328 | A1 | 3/2017 | Li et al. |
| 2017/0065647 | A1 | 3/2017 | Kim et al. |
| 2017/0151291 | A1 | 6/2017 | Henn et al. |
| 2017/0165302 | A1 | 6/2017 | Henn et al. |
| 2017/0304373 | A1 | 10/2017 | Taylor et al. |
| 2018/0078588 | A1 | 3/2018 | Taylor et al. |
| 2019/0008930 | A1 | 1/2019 | Modlin et al. |
| 2019/0030090 | A1* | 1/2019 | Li .......................... A61K 8/606 |
| 2019/0249149 | A1* | 8/2019 | Modlin ................. C12N 15/11 |
| 2019/0314428 | A1* | 10/2019 | Patzold ................... A61K 9/06 |
| 2019/0316183 | A1* | 10/2019 | Li .......................... A61P 17/10 |
| 2021/0123092 | A1* | 4/2021 | Li .......................... A61K 35/76 |
| 2021/0128641 | A1 | 5/2021 | Kim et al. |
| 2021/0137997 | A1* | 5/2021 | Li .......................... C12Q 1/04 |
| 2021/0177920 | A1* | 6/2021 | Weinstock ............ A61K 45/06 |
| 2021/0393510 | A1* | 12/2021 | Hitchcock ........... A61K 9/0014 |

FOREIGN PATENT DOCUMENTS

| | | | |
|---|---|---|---|
| WO | WO-03/033515 A1 | 4/2003 | |
| WO | WO-07/056680 A2 | 5/2007 | |
| WO | WO-2009/105592 A2 | 8/2009 | |
| WO | WO-10/065735 A2 | 6/2010 | |
| WO | WO-2011/149099 A1 | 12/2011 | |
| WO | WO-2013/142378 A1 | 9/2013 | |
| WO | WO-2015/195845 A1 | 12/2015 | |
| WO | WO-2017/136738 A2 | 8/2017 | |
| WO | WO-2017136738 A2 * | 8/2017 | ........... A61K 31/714 |

OTHER PUBLICATIONS

Agak et al., "Phenotype and Antimicrobial Activity of Th17 Cells Induced by Propionibacterium Acnes Strains Associated With Healthy and Acne Skin," J Invest Dermatol, 138(2):316-324 (2017).
Alexeyev, et al., "Shooting at skin Propionibacterium acnes: to be or not to be on target," J Invest Dermatol, 133(9): 2292-2294 (2013).
Bik et al., "Bacterial diversity in the oral cavity of 10 healthy individuals," The ISME Journal, 4(8):962-974(2010).
Bojar, et al., "Acne and Propionibacterium Acnes," Clinics in Dermatology. 22(5): 375-379 (2004).
Brzuszkiewicz, E. et al., "Comparative Genomics and Transcriptomics of *Propionibacterium Acnes*," PLoS One6:e21581 6(6) (2011).
Craft, et al., "Response to the commentaries on the paper: Propionibacterium acnes strain populations in the human skin microbiome associated with acne," J Invest Dermatol. 133(9): 2295-2297 (2013).
Eady et al., "Propionibacterium acnes resistance: a worldwide problem," Dermatology, 206(1):54-56 (2003).
Eady, et al., "A distinct acne microbiome: fact or fiction?" J Invest Dermatol, 133(9): 2294-2295 (2013).
Extended European Search Report for EP Application No. 17002012.7 dated Jun. 4, 2018.
Extended European Search Report for EP Application No. 1921844.8 dated May 13, 2020.
Extended European Search Report issued by the European Patent Office in corresponding Application No. EP 15788711.8, dated Nov. 21, 2017.
Farrar et al., "Genome Sequence and Analysis of a Propionibacterium Acnes Bacteriophage," Journal of Bacteriology, 189(11): 4161-4167 (2007).
Fitz-Gibbon, S. et al., "*Propionibacterium Acnes* Strain Populations in the Human Skin Microbiome Associated with Acne," J. Invest Dermatol., 133(9):2152-2160 (2013).
GenBank Accession No. AE017283.1, Propionibacterium acnes KPA171202, complete genome, Nov. 21, 2011.
Grice, E.A et al., "Topographical and Temporal Diversity of the Human Skin Microbiome," Science, 324(5931 ):1190-1192 (2009).
Jahns et al., "Simultaneous Visualization of Propionibacterium Acnes and Propionibacterium Granulosum with Immunofluorescence and Fluorescence in Situ Hybridization," Anaerobe, 23: 48-54 (2013).
Johnson et al., "Strain-Level Differences in Porphyrin Production and Regulation in Propionibacterium acnes Elucidate Disease Associations," mSphere, 1(1):e00023-15 (2016).
Kasimatis, G. et al., "Analysis of Complete Gemones of *Propionibacterium Acnes* Reveals a Novel Plasmid and Increased Pseudogenes in an Acne Associated Strain," Biomed Res Int., 2013:1-11 (2013).

(56) References Cited

OTHER PUBLICATIONS

Kilian et al., "Multilocus Sequence Typing and Phylogenetic Analysis of Propionibacterium acnes," Journal of Clinical Microbiology, 50(4): 1158-1165 (2012).
Leyden et al., "The Evolving Role of Propionibacterium Acnes in Acne," Seminars in Cutaneous Medicine and Surgery, 20(3): 139-143 (2001).
Li et al., "An Unbalanced Microbiome on the Face May Be Key to Acne Development," Microbiology Society, Charles Darwin House, 12 Roger Street, London WC1N 2JU, UK; Barnard E, HPC-Household and Personal Care Today, 2017, Newsletter May, May 30, 2017.
Li, H. et al., "Metagemonic Study of the Human Skin Microbiome Associated with Acne," Nature Proceedings, Posted Nov. 22, 2010.
Lomholt, H.B. et al., "Population Genetic Analysis of *Propionibacterium Acnes* Identifies a Subpopulation and Epidemic Clones Associated with Acne," PLoS One, 5(8):e12277 (2010).
Marinelli, L.J. et al., "*Propionibacterium Acnes* Bacteriophages Display Limited Genetic Diversity and Broad Killing Activity against Bacterial Skin Isolates," MBio, 3(5):1-13 (2012).
Marinelli, L.J. et al., "Propionibacterium Acnes Bacteriophages Display Limited Genetic Diversity and Broad Killing Activity Against Bacterial Skin Isolates," Poster (2011).
Marinelli, L.J. et al., "*Propionibacterium Acnes* Bacteriophages Display Limited Genetic Diversity and Broad Killing Activity Against Bacterial Skin Isolates," Poster 2012.
McDowell, A. et al., "A Novel Multilocus Sequence Typing Scheme for the Opportunistic Pathogen *Propionibacterium Acnes* and Characterization of Type I Cell Surface-Associated Antigens," Microbiology, 157:1990-2003 (2011).
McDowell, A. et al., "An Expanded Multilocus Sequence Typing Scheme for *Propionibacterium Acnes*: Investigation of 'Pathogenic', 'Commensal' and Antibiotic Resistant Strains," PLoS One, 7(7): e 41480 (2012).
McDowell, Andrew et al. "The Opportunistic Pathogen Propionibacterium acnes: Insights into Typing, Human Disease, Clonal Diversification and CAMP Factor Evolution," PLOS One; 8(9): e70897 (pp. 1-22) (Sep. 2013).
Miura et al., "Quantitative PGR of Propionibacterium Acnes DNA in Samples Aspirated from Sebaceous Follicles on the Normal Skin of Subjects With or Without Acne," J Med Dent Sci, 57: 65-74 (2010).
Nagy et al., "MALDI-TOF MS fingerprinting facilitates rapid discrimination of phylotypes I, II and III of Propionibacterium acnes," Anaerobe, 20:20-26 (2013).
Nakatsuji, T. et al., "Antibodies Elicited by Inactivated Propionibacterium Acnes-Based Vaccines Exert Protective Immunity and Attenuate the IL-8 Production in Human Sebocytes: Relevance to Therapy for Acne Vulgaris," J. Invest. Dermatol., 128(10):2451-2457 (2008).
Nakatsuji, T. et al., "Antimicrobial Property of Lauric Acid Against *Propionibacterium Acnes*: Its Therapeutic Potential for Inflammatory Acne Vulgaris," J. Invest. Dermatol., 129:2480-2488 ((2009).
NCBI Accession No. PRJNA49191, Cutibacterium acnes HL110PA3 [Taxonomy IDS: 765079]: (2010).
NCBI Biosample SAMN00189249; sampler name: 71451, MIGS: cultured Bacterial/Archeal sample from Propionibacterium acnes HL110PA3: (2010).
Shu et al., "Fermentation of Propionibacterium acnes, a commensal bacterium in the human skin microbiome, as skin probiotics against methicillin-resistant *Staphylococcus aureus*," PLoS One, 8(2):e55380 (2013).
Tomida, S. et al., "Pan-Genome and Comparative Genome Analyses of *Propionibacterium Acnes* Reveal Its Genomic Diversity in the Healthy and Diseased Human Skin Microbiome," mBio, 4(3): e00003-13 (2013).
Woo et al., "Then and now: use of 16S rDNA gene sequencing for bacterial identification and discovery of novel bacteria in clinical microbiology laboratories," Clinical Microbiology and Infection, 14(10):908-934 (2008).
Yu et al., "Different Propionibacterium acnes phylotypes induce distinct immune responses and express unique surface and secreted proteomes," J Investig Dermatol, 136(11):2221-2228 (2016).
Henseler et al., "Mycoses in patients with psoriasis or atopic dermatitis" Mycoses, 40(1):22-28 (1997).

* cited by examiner

\* CRISPR spacers that match to the sequence in locus 2, which is highly homologous to the sequence in *Clostridium leptum*.
\*\* CRISPR spacers that match to the sequence in locus 3, which is highly homologous to the sequence in *Clostridium leptum*.

FIGURE 22, Panel A

| Genetic Alteration | RPA17202 Locus_tag | Product Name | Length (bp) | SK137 Locus_tag | Product Name | Length (bp) |
|---|---|---|---|---|---|---|
| TAGATA deletion in type II fbase deletion at 124th nt | PPA1796' | triacylglycerol lipase precursor | 1,020 | HMPREF0675_4855' | triacylglycerol lipase | 888 |
| | NA | NA | NA | HMPREF0675_4856' | triacylglycerol lipase | 1,014 |
| TACA insertion in type IA/IB at 505th nt | PPA1425' | putative lysophospholipase | 1,134 | HMPREF0675_4479' | putative lysophospholipase L2 | 498 |
| | | | | HMPREF0675_4480' | putative lysophospholipase L2 | 168 |
| | | | | HMPREF0675_4481' | putative lysophospholipase L2 | 426 |
| 13bp insertion in IB-3/type II | PPA0594' | putative lysophospholipase | 939 | HMPREF0675_3655/3657 | hypothetical protein | 924 |
| 10C in SK137, normaly 9C | PPA1761 | cardiolipin synthetase | 1,269 | HMPREF0675_4816' | phospholipase D domain protein | 1,188 |
| | | | | HMPREF0675_4817 | hypothetical protein | |
| Premature stop codon at 170th nt | PPA2142' | putative lysophospholipase | 1,122 | HMPREF0675_5205' | lysophospholipase L2 domain protein | 1,122 |
| | | | | HMPREF0675_5206' | lysophospholipase L2 | |
| Conserved | PPA1953' | patatin-like phospholipase | 1,503 | HMPREF0675_5014' | phospholipase, patatin family | 1,503 |
| Conserved | PPA2038' | lipase/acylhydrolase | 909 | HMPREF0675_5101 | GDSL-like protein | 909 |
| Conserved | PPA2105' | triacylglycerol lipase precursor | 1,020 | HMPREF0675_5159' | triacylglycerol lipase | 1,020 |
| Conserved | PPA1035' | putative lipase | 1,287 | HMPREF0675_4092/4094 | hypothetical protein | 1,287 |
| Conserved | PPA1101' | putative esterase/lipase YbF | 819 | HMPREF0675_4163 | hydrolase, alpha/beta domain protein | 819 |
| Conserved | PPA1987' | putative lysophospholipase | 957 | HMPREF0675_5031 | hydrolase, alpha/beta domain protein | 957 |
| Conserved | PPA2317' | lipase/esterase | 930 | HMPREF0675_5390 | hydrolase, alpha/beta domain protein | 930 |
| Conserved | NA | NA | NA | HMPREF0675_5037' | phospholipase, patatin family | 1,032 |

FIGURE 22, Panel B

Figure 25
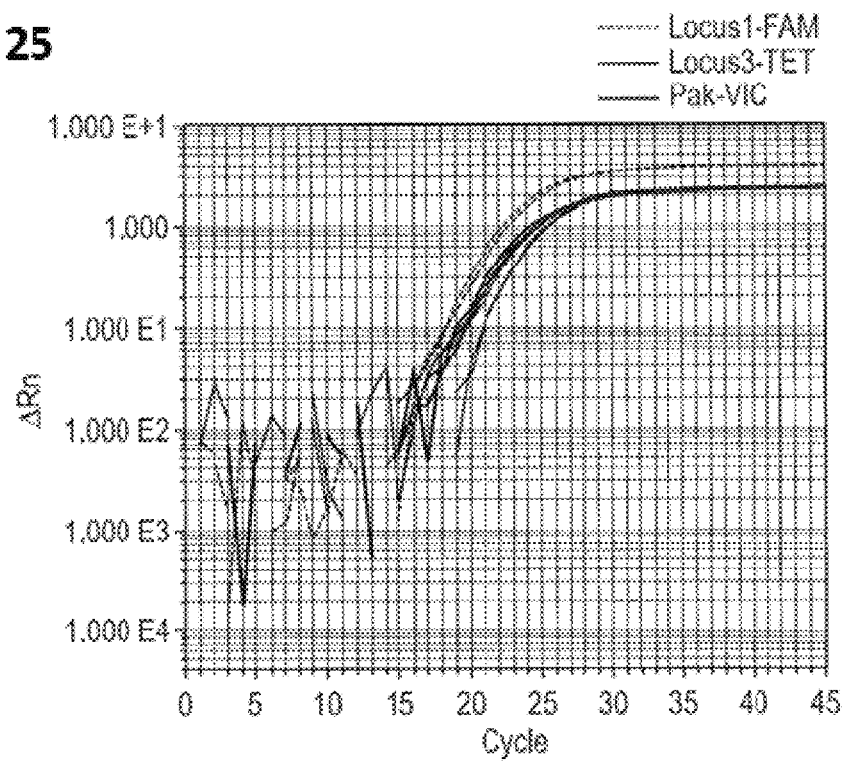
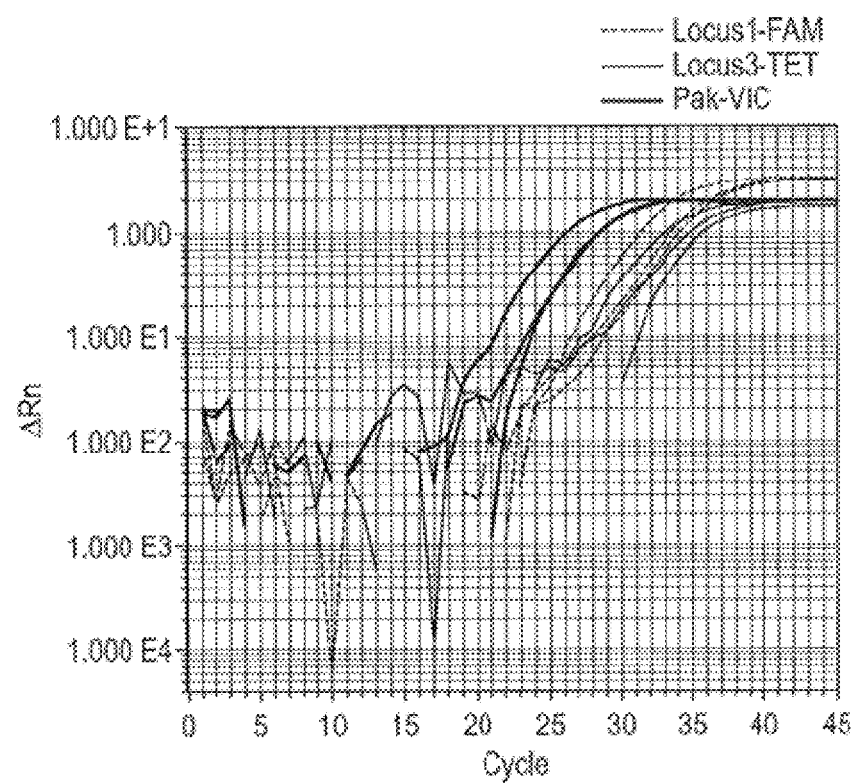

Panel A**

Panel B**

Panel C**

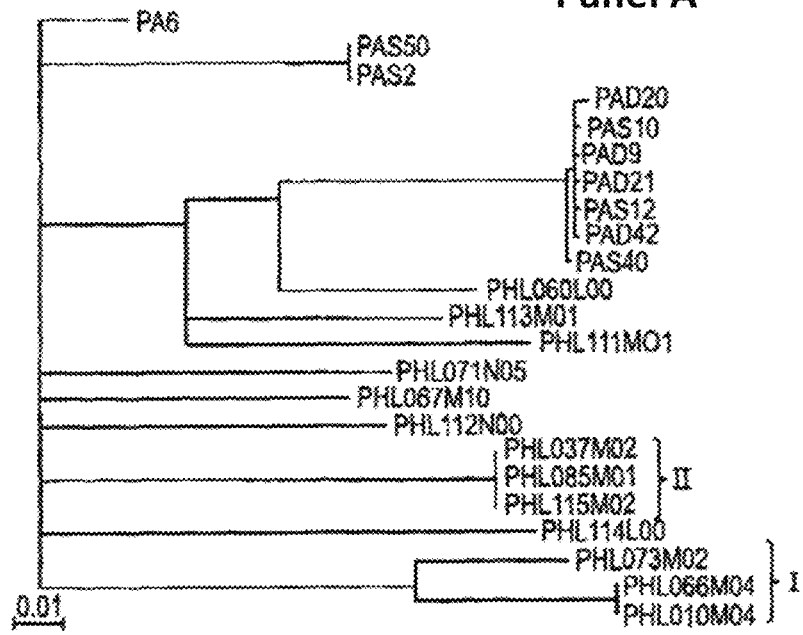
Figure 32 Panel A
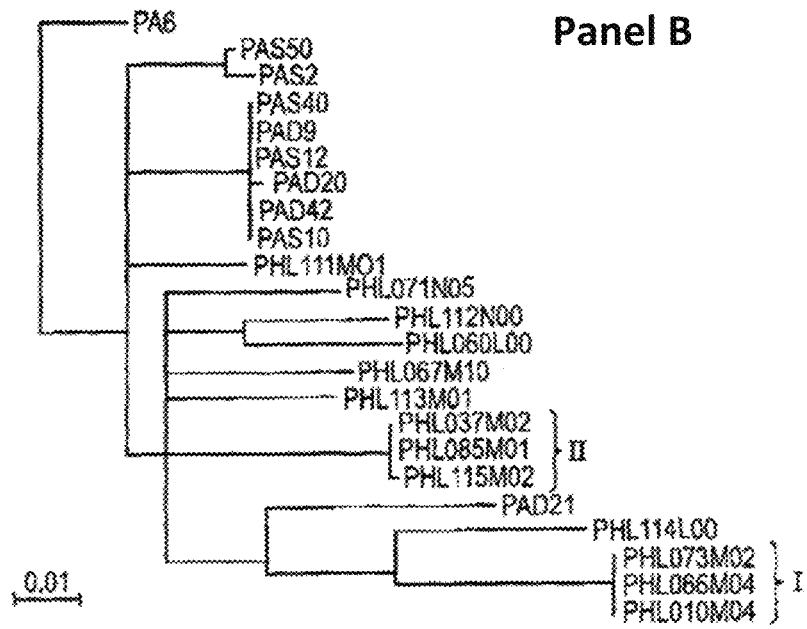
Figure 32 Panel B

FAST DIAGNOSIS AND PERSONALIZED TREATMENTS FOR ACNE

CROSS-REFERENCE TO RELATED APPLICATIONS

This application is a continuation application of U.S. patent application Ser. No. 16/390,575, filed Apr. 22, 2019, which is a continuation application of U.S. patent application Ser. No. 15/257,423, filed Sep. 6, 2016, which is a divisional application of U.S. National Stage application Ser. No. 14/385,576, filed Sep. 16, 2014, which claims priority to International Application No. PCT/US2013/032551, filed on Mar. 15, 2013, which claims priority to U.S. Provisional Patent Application No. 61/612,290, filed on Mar. 17, 2012, each of which is incorporated by reference herein in its entirety for all purposes.

STATEMENT REGARDING FEDERALLY SPONSORED RESEARCH

This invention was made with government support under Grant Numbers AR057503 and GM099530, awarded by the National Institutes of Health. The government has certain rights in the invention.

SEQUENCE LISTING

The instant application contains a Sequence Listing which has been submitted electronically in ASCII format and is hereby incorporated by reference in its entirety. Said ASCII copy was submitted on Sep. 6, 2016 and is 3348.71 kilobytes in size.

BACKGROUND OF THE INVENTION

Acne is a skin condition that causes pimples or "zits." This includes whiteheads, blackheads, and red, inflamed patches of skin (such as cysts). Acne occurs when tiny pores on the surface of the skin become clogged. Each pore opens to a follicle. A follicle contains a hair and an oil gland. The oil released by the gland helps remove old skin cells and keeps your skin soft. When glands produce too much oil, the pores can become blocked. Dirt, bacteria, and cells build up. The blockage is called a plug or comedone. If the top of the plug is white, it is called a whitehead. If the top of the plug is dark, it is called a blackhead. If the plug breaks open, swelling and red bumps occur. Acne that is deep in your skin can cause hard, painful cysts. This is called cystic acne.

Acne is most common in teenagers, but anyone can get acne. 85% of teenagers have acne. Hormonal changes may cause the skin to be more oily. Acne tends to run in families. It may be triggered by hormonal changes related to puberty, menstrual periods, pregnancy, birth control pills, or stress; greasy or oily cosmetic and hair products; certain drugs (such as steroids, testosterone, estrogen, and phenytoin); or high levels of humidity and sweating.

Various treatments exist for the treatment of acne. In general, acne treatments work by reducing oil production, speeding up skin cell turnover, fighting bacterial infection, reducing the inflammation or doing all four. These types of acne treatments include over-the-counter topical treatments, antibiotics, oral contraceptives and cosmetic procedures. Acne lotions may dry up the oil, kill bacteria and promote sloughing of dead skin cells. Over-the-counter (OTC) lotions are generally mild and contain benzoyl peroxide, sulfur, resorcinol, salicylic acid or sulfur as their active ingredient. Studies have found that using topical benzoyl peroxide along with oral antibiotics may reduce the risk of developing antibiotic resistance. Antibiotics may cause side effects, such as an upset stomach, dizziness or skin discoloration. These drugs also increase your skin's sun sensitivity and may reduce the effectiveness of oral contraceptives. For deep cysts, antibiotics may not be enough. Isotretinoin (Amnesteem, Claravis, Sotret) is a powerful medication available for scarring cystic acne or acne that doesn't respond to other treatments. However, isotretinoin has many side effects, such as dry skin, depression, severe stomach pain, and muscle/joint/back pain, and can cause birth defects in babies whose mothers use isotretinoin. Oral contraceptives, including a combination of norgestimate and ethinyl estradiol (Ortho Tri-Cyclen, Previfem, others), can improve acne in women. However, oral contraceptives may cause other side effects, such as headaches, breast tenderness, nausea, and depression. Chemical peels and microdermabrasion may be helpful in controlling acne. These cosmetic procedures, which have traditionally been used to lessen the appearance of fine lines, sun damage, and minor facial scars, are most effective when used in combination with other acne treatments. They may cause temporary, severe redness, scaling and blistering, and long-term discoloration of the skin.

In addition to the negative side-effects caused by the currently available treatments, there is no treatment available that is personalized to patients to target specific bacteria causing acne on an individual level. Additionally, it will be useful for dermatologists to know which strains are dominant on the skin of a patient at the time of diagnosis in order to personalize acne treatments. Thus, there exists a need in the art for methods of personalized diagnoses and treatment of acne.

BRIEF SUMMARY OF THE INVENTION

The present invention is directed to methods of diagnosis and personalized treatment in patients afflicted with acne.

In one embodiment, the invention provides a method for determining whether an individual possesses acne comprising: obtaining a skin sample from an individual; isolating bacterial DNA from said sample; amplifying 16S ribosomal DNA in said sample; sequencing said amplified DNA products; and typing the individual's DNA based on one or more of the ten major ribotypes (RTs) of *P. acnes* strains, RT1-RT10 (SEQ ID NOs 1-10), wherein said typing occurs by determining whether said individual possesses one or more of RT1-RT10 and wherein said individual is diagnosed as having acne if said individual possesses RT4, RT5, RT7, RT8, RT9, or RT10. For example, said individual may be diagnosed as having acne if said individual possesses RT4 (SEQ ID NO:4), RT5 (SEQ ID NO:5), or RT8 (SEQ ID NO:8).

In another embodiment, the invention provides a method for diagnosing different types of acne comprising: obtaining a skin sample from a subject; isolating bacterial DNA from said sample; amplifying 16S ribosomal DNA in said sample; sequencing said amplified DNA products; and typing the subject's DNA based on one or more of the five major microbiome types of *P. acnes* strains, wherein said subject is diagnosed as having acne if said subject is typed to microbiome IV or V.

In yet another embodiment, the invention provides a method for rapidly diagnosing acne comprising: obtaining a skin sample from a subject; isolating bacterial DNA from said sample; using one or more primer sets to amplify said DNA; and analyzing said amplified DNA for the presence of a sequence having at least 95% homology with at least one of SEQ ID NOs 29-32 and 82-434, wherein said subject is diagnosed as having acne if the presence of a sequence having at least 95% homology with at least one of SEQ ID NOs 29-32 and 82-434 exists. For example, said amplified DNA may be analyzed for the presence of a sequence having at least 99% homology with at least one of SEQ ID NOs 29-32 and 82-434 and wherein said subject is diagnosed as having acne if the presence of a sequence having at least 99% homology with at least one of SEQ ID NOs 29-32 and 82-434 exists. As another example, said amplified DNA may be analyzed for the presence of at least one of SEQ ID NOs 29-32 and 82-434 and wherein said subject is diagnosed as having acne if the presence of at least one of SEQ ID NOs 29-32 and 82-434 exists.

In another embodiment, the invention provides a method for rapidly diagnosing acne comprising: obtaining a skin sample from a subject; isolating bacterial DNA from said sample; using one or more primer sets to amplify said DNA; using one or more probes to detect said amplified DNA; and analyzing said probe signals for the presence of Locus 1 (at least one sequence having at least 95% homology to at least one of SEQ ID NOs 29 and 82-97), Locus 2 (at least one sequence having at least 95% homology to at least one of SEQ ID NOs 30 and 98-186), Locus 3 (at least one sequence having at least 95% homology to at least one of SEQ ID NOs 31 and 187-423), and/or Locus 4 (at least one sequence having at least 95% homology to at least one of SEQ ID NOs 32 and 424-434), wherein said subject is diagnosed as having acne if one or more of Loci 1-4 are present. For example, the signals may be analyzed for the presence of Locus 1, Locus 2, Locus 3, and/or Locus 4 based upon at least 99% homology or 100% homology.

In the foregoing methods, a primer of said primer sets may be selected from the group consisting of SEQ ID NOs 11, 12, 17, and 18 (for Locus 1), SEQ ID NOs 13, 14, 20, and 21 (for Locus 2), SEQ ID NOs 15, 16, 23, and 24 (for Locus 3), and SEQ ID NOs 26 and 27 (for Locus 4). In the foregoing methods, said probes may be SEQ ID NO:19 (for Locus 1), SEQ ID NO:22 (for Locus 2), SEQ ID NO:25 (for Locus 3), and SEQ ID NO:28 (for Locus 4).

In yet another embodiment, the invention provides a vaccine for the prevention and/or treatment of acne caused by *P. acnes* comprising a heat inactivated *P. acnes* strain, an attenuated protein of said strain, or combination thereof, wherein said strain is an RT4 strain, an RT5 strain, an RT7 strain, an RT8 strain, an RT9 strain, or an RT10 strain.

In yet another embodiment, the invention provides a vaccine for the prevention and/or treatment of acne caused by *P. acnes* comprising a heat inactivated *P. acnes* strain, an attenuated protein of said strain, or combination thereof identified to be specific to a subject based on 16S rDNA sequence analysis of the strains of *P. acnes* affecting said subject.

With regard to the vaccines, said heat inactivated *P. acnes* strain, attenuated protein, or combination thereof may be specific for at least one of unique genomic loci, regions, or sequences identified for the strains of *P. acnes*. Said heat inactivated *P. acnes* strain, attenuated protein, or combination thereof may be specific for at least one of Locus 1 (SEQ ID NOs 29 and 82-97), Locus 2 (SEQ ID NOs 30 and 98-186), Locus 3 (31 and 187-423), and Locus 4 (32 and 424-434). In yet another embodiment, the invention provides a method for the personalized treatment of acne comprising determining the strains of *P. acnes* affecting a subject and treating said subject with an active ingredient directed to at least one detected strain of *P. acnes*, wherein the active ingredient comprises a drug targeting specific strains of *P. acnes*, wherein the targeting drug comprises small molecules, antisense molecules, siRNA, biologics, antibodies, and combinations thereof targeting genomic elements specific for strains of *P. acnes* associated with acne.

In yet another embodiment, the invention provides a method for treating acne comprising: administering an effective amount of a probiotic that comprises at least one strain of *P. acnes* that is associated with healthy or normal skin based on its 16S rDNA. Said strain may be an RT6 strain. Said strain may have at least 95% homology to SEQ ID NO:51, SEQ ID NO:52, SEQ ID NO:53, or SEQ ID NO:54, such as at least 99% homology or 100% homology.

In yet another embodiment, the invention provides a method for treating acne comprising: administering an effective amount of a metabolite produced by a strain of *P. acnes* that is associated with healthy or normal skin, wherein said metabolite is selected from the group comprising bacterial culture supernatant, cell lysate, proteins, nucleic acids, lipids, and other bacterial molecules. Said strain may be an RT6 strain. Said strain may have at least 95% homology to SEQ ID NO:51, SEQ ID NO:52, SEQ ID NO:53, or SEQ ID NO:54, such as at least 99% homology or 100% homology.

In yet another embodiment, the invention provides a method for treating acne in a subject comprising: administering an effective amount of a drug specifically targeting RT4, RT5, RT7, RT8, RT9, or RT10, when said subject is determined to possess RT4, RT5, RT7, RT8, RT9, or RT10, respectively. The earlier-described methods may be performed prior to administration of said drug. Said drug may be a small molecule, antisense molecule, siRNA, biologic, antibody, or combination thereof.

In yet another embodiment, the invention provides a composition comprising at least one strain of *P. acnes* that is associated with healthy or normal skin. Said strain may be an RT6 strain. Said strain may have at least 95% homology to SEQ ID NO:51, SEQ ID NO:52, SEQ ID NO:53, or SEQ ID NO:54, such as at least 99% homology or 100% homology.

In yet another embodiment, the invention provides a method for diagnosing IB-3-based acne comprising: obtaining a skin sample from a subject; isolating bacterial DNA from said sample; using one or more primer sets to amplify said DNA; and analyzing said amplified DNA for the presence of a sequence having at least 95% homology with at least one of SEQ ID NOs 55-81, wherein said subject is diagnosed as having IB-3-based acne if the presence of a sequence having at least 95% homology with at least one of SEQ ID NOs 55-81 exists.

In yet another embodiment, the invention provides a method for the personalized treatment of acne comprising determining the strain(s) of acne affecting a subject and administering to said subject an effective amount of at least one phage specifically directed to said strain(s). For example, the subject may be treated with phage directed against an RT4 strain, an RT5 strain, an RT7 strain, and RT8 strain, an RT9 strain, and/or an RT10 strain.

In yet another embodiment, the invention provides a method for treating an individual suffering from acne of microbiome type I comprising administering to said individual an effective amount of a phage, wherein said phage is selected from the group consisting of: PHL113M01 (SEQ ID NO:36), PHL111M01 (SEQ ID NO:33), PHL082M00 (SEQ ID NO:47), PHL060L00 (SEQ ID NO:34), PHL067M10 (SEQ ID NO:42), PHL071N05 (SEQ ID NO:41), PHL112N00 (SEQ ID NO:35), PHL037M02 (SEQ ID NO:40), PHL085N00 (SEQ ID NO:46), PHL115M02 (SEQ ID NO:43), PHL085M01 (SEQ ID NO:44), PHL114L00 (SEQ ID NO:37), PHL010M04 (SEQ ID NO:38), and PHL066M04 (SEQ ID NO:39).

In yet another embodiment, the invention provides a method for treating an individual suffering from acne of microbiome type I with IB-3 strain comprising administering to said individual an effective amount of a phage, wherein said phage is selected from the group consisting of: PHL082M00 (SEQ ID NO:47) and PHL071N05 (SEQ ID NO:41).

In yet another embodiment, the invention provides a method for treating an individual suffering from acne of microbiome type II comprising administering to said individual an effective amount of a phage, wherein said phage is selected from the group consisting of: PHL113M01 (SEQ ID NO:36), PHL060L00 (SEQ ID NO:34), PHL112N00 (SEQ ID NO:35), and PHL085M01 (SEQ ID NO:44).

In yet another embodiment, the invention provides a method for treating an individual suffering from acne of microbiome type III or dominant RT8 comprising administering to said individual an effective amount of a phage, wherein said phage is selected from the group consisting of: PHL113M01 (SEQ ID NO:36), PHL111M01 (SEQ ID NO:33), PHL082M00 (SEQ ID NO:47), PHL060L00 (SEQ ID NO:34), PHL067M10 (SEQ ID NO:42), PHL071N05 (SEQ ID NO:41), PHL112N00 (SEQ ID NO:35), PHL037M02 (SEQ ID NO:45), PHL085N00 (SEQ ID NO:46), PHL115M02 (SEQ ID NO:43), PHL085M01 (SEQ ID NO:44), PHL114L00 (SEQ ID NO:37), PHL073M02 (SEQ ID NO:40), PHL010M04 (SEQ ID NO:38), and PHL066M04 (SEQ ID NO:39).

In yet another embodiment, the invention provides a method for treating an individual suffering from acne of microbiome type IV comprising administering to said individual an effective amount of a phage, wherein said phage is selected from the group consisting of: PHL113M01 (SEQ ID NO:36), PHL111M01 (SEQ ID NO:33), PHL082M00 (SEQ ID NO:47), PHL060L00 (SEQ ID NO:34), PHL067M10 (SEQ ID NO:42), PHL071N05 (SEQ ID NO:41), PHL112N00 (SEQ ID NO:35), PHL037M02 (SEQ ID NO:45), PHL085N00 (SEQ ID NO:46), PHL115M02 (SEQ ID NO:43), PHL085M01 (SEQ ID NO:44), PHL114L00 (SEQ ID NO:37), PHL073M02 (SEQ ID NO:40), PHL010M04 (SEQ ID NO:38), and PHL066M04 (SEQ ID NO:39).

In yet another embodiment, the invention provides a method for treating an individual suffering from acne of microbiome type V comprising administering to said individual an effective amount of a phage, wherein said phage is selected from the group consisting of: PHL113M01 (SEQ ID NO:36), PHL111M01 (SEQ ID NO:33), PHL082M00 (SEQ ID NO:47), PHL060L00 (SEQ ID NO:34), PHL067M10 (SEQ ID NO:42), PHL071N05 (SEQ ID NO:41), PHL112N00 (SEQ ID NO:35), PHL037M02 (SEQ ID NO:45), PHL085N00 (SEQ ID NO:46), PHL115M02 (SEQ ID NO:43), PHL085M01 (SEQ ID NO:44), PHL114L00 (SEQ ID NO:37), PHL073M02 (SEQ ID NO:40), PHL010M04 (SEQ ID NO:38), and PHL066M04 (SEQ ID NO:39).

In yet another embodiment, the invention provides a method for treating a *Propionibacterium humerusii*-associated malady comprising administering to said individual an effective amount of a phage, wherein said phage is selected from the group consisting of: PHL113M01 (SEQ ID NO:36), PHL111M01 (SEQ ID NO:33), PHL082M00 (SEQ ID NO:47), PHL067M10 (SEQ ID NO:42), PHL071N05 (SEQ ID NO:41), PHL085N00 (SEQ ID NO:46), PHL085M01 (SEQ ID NO:44), PHL114L00 (SEQ ID NO:37), PHL073M02 (SEQ ID NO:40), and PHL010M04 (SEQ ID NO:38).

In yet another embodiment, the invention provides a kit for diagnosing acne in a subject, wherein said kit comprises: at least one primer selected from the group comprising SEQ ID NOs 11-18, 20, 21, 23, 24, 26, and 27; and instructions for use.

In yet another embodiment, the invention provides a kit for diagnosing acne in a subject, wherein said kit comprises: at least one primer selected from the group comprising SEQ ID NOs 11-18, 20, 21, 23, 24, 26, and 27; at least one probe selected from the group comprising SEQ ID NOs 19, 22, 25, and 28; and instructions for use.

BRIEF DESCRIPTION OF THE FIGURES

FIG. 25 reflects qPCR triplex amplification plots for clinical samples #1 (A) and #2 (B) showing amplification of *P. acnes* Locus 1, Locus 3, and Pak.

FIG. 32 shows the phylogentic trees constructed based upon the nucleotide sequences of amidase (A) and head protein (B) from all phages, including the sequences from Lood et al. The phylogenetic relationships among the phages from the previous study remain the same in these trees. Groups I and II remain the same as in the genome shown in FIG. 30.

DETAILED DESCRIPTION

Figure 1:
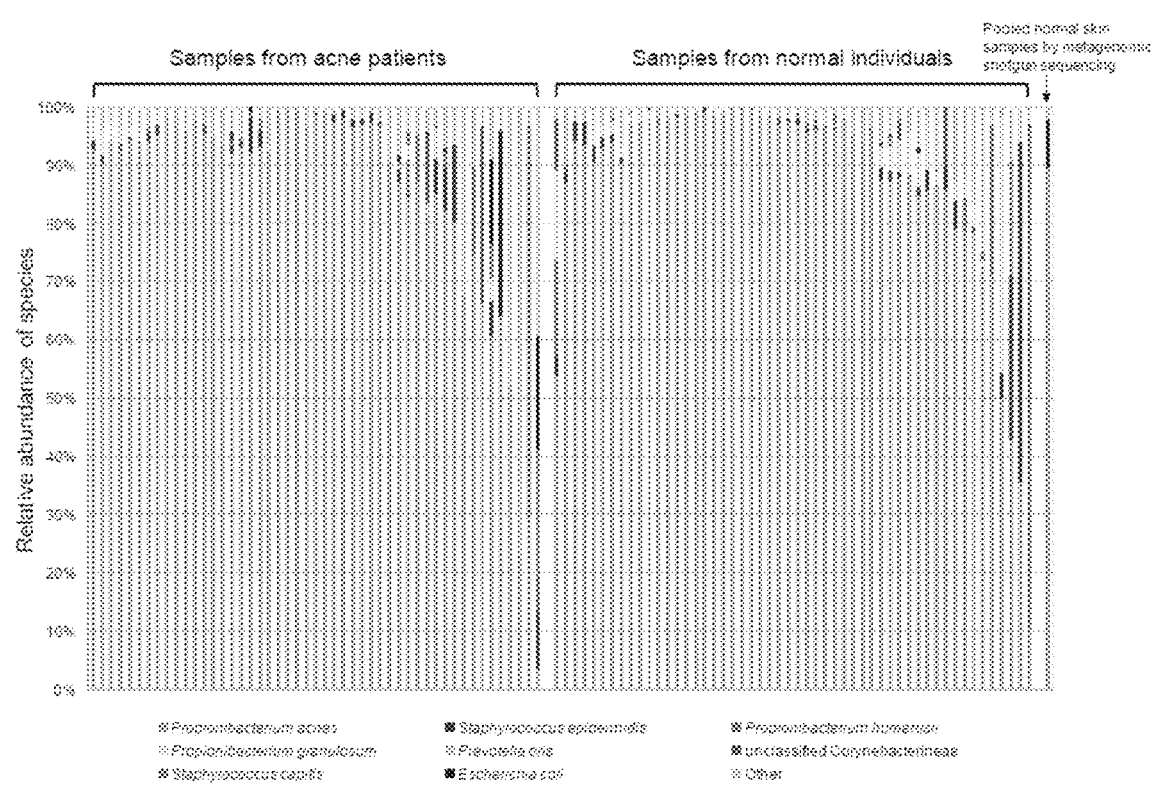
FIG. 1 shows that *P. acnes* dominates the microbiota of pilosebaceous units, accounting for 87% of the clones. *P. acnes* was dominant in pilosebaceous units in both acne patients and individuals with normal skin. By 16S rDNA sequencing, *P. acnes* sequences accounted for 87% of all the clones. Species with a relative abundance greater than 0.35% are listed in order of relative abundance. Species distribution from a metagenomic shotgun sequencing of pooled samples from normal individuals confirmed the high abundance of *P. acnes* in pilosebaceous units, as shown on the far right column.

In one embodiment, the invention provides a method for determining whether an individual possesses acne comprising: obtaining a skin sample from an individual; isolating bacterial DNA from said sample; amplifying 16S ribosomal DNA in said sample; sequencing said amplified DNA products; and typing the individual's DNA based on one or more of the ten major ribotypes (RTs) of *P. acnes* strains, RT1-RT10 (SEQ ID NOs 1-10), wherein said typing occurs by determining whether said individual possesses one or more of RT1-RT10 and wherein said individual is diagnosed as having acne if said individual possesses RT4, RT5, RT7, RT8, RT9, or RT10. For example, said individual may be diagnosed as having acne if said individual possesses RT4 (SEQ ID NO:4), RT5 (SEQ ID NO:5), or RT8 (SEQ ID NO:8).

In another embodiment, the invention provides a method for diagnosing different types of acne comprising: obtaining a skin sample from a subject; isolating bacterial DNA from said sample; amplifying 16S ribosomal DNA in said sample; sequencing said amplified DNA products; and typing the subject's DNA based on one or more of the five major microbiome types of *P. acnes* strains, wherein said subject is diagnosed as having acne if said subject is typed to microbiome IV or V.

In yet another embodiment, the invention provides a method for rapidly diagnosing acne comprising: obtaining a skin sample from a subject; isolating bacterial DNA from said sample; using one or more primer sets to amplify said DNA; and analyzing said amplified DNA for the presence of a sequence having at least 95% homology with at least one of SEQ ID NOs 29-32 and 82-434, wherein said subject is diagnosed as having acne if the presence of a sequence having at least 95% homology with at least one of SEQ ID NOs 29-32 and 82-434 exists. For example, said amplified DNA may be analyzed for the presence of a sequence having at least 99% homology with at least one of SEQ ID NOs 29-32 and 82-434 and wherein said subject is diagnosed as having acne if the presence of a sequence having at least 99% homology with at least one of SEQ ID NOs 29-32 and 82-434 exists. As another example, said amplified DNA may be analyzed for the presence of at least one of SEQ ID NOs 29-32 and 82-434 and wherein said subject is diagnosed as having acne if the presence of at least one of SEQ ID NOs 29-32 and 82-434 exists.

In another embodiment, the invention provides a method for rapidly diagnosing acne comprising: obtaining a skin sample from a subject; isolating bacterial DNA from said sample; using one or more primer sets to amplify said DNA; using one or more probes to detect said amplified DNA; and analyzing said probe signals for the presence of Locus 1 (at least one sequence having at least 95% homology to at least one of SEQ ID NOs 29 and 82-97), Locus 2 (at least one sequence having at least 95% homology to at least one of SEQ ID NOs 30 and 98-186), Locus 3 (at least one sequence having at least 95% homology to at least one of SEQ ID NOs 31 and 187-423), and/or Locus 4 (at least one sequence having at least 95% homology to at least one of SEQ ID NOs 32 and 424-434), wherein said subject is diagnosed as having acne if one or more of Loci 1-4 are present. For example, the signals may be analyzed for the presence of Locus 1, Locus 2, Locus 3, and/or Locus 4 based upon at least 99% homology or 100% homology.

In the foregoing methods, a primer of said primer sets may be selected from the group consisting of SEQ ID NOs 11, 12, 17, and 18 (for Locus 1), SEQ ID NOs 13, 14, 20, and 21 (for Locus 2), SEQ ID NOs 15, 16, 23, and 24 (for Locus 3), and SEQ ID NOs 26 and 27 (for Locus 4). In the foregoing methods, said probes may be SEQ ID NO:19 (for Locus 1), SEQ ID NO:22 (for Locus 2), SEQ ID NO:25 (for Locus 3), and SEQ ID NO:28 (for Locus 4).

In yet another embodiment, the invention provides a vaccine for the prevention and/or treatment of acne caused by *P. acnes* comprising a heat inactivated *P. acnes* strain, an attenuated protein of said strain, or combination thereof, wherein said strain is an RT4 strain, an RT5 strain, an RT7 strain, an RT8 strain, an RT9 strain, or an RT10 strain.

In yet another embodiment, the invention provides a vaccine for the prevention and/or treatment of acne caused by *P. acnes* comprising a heat inactivated *P. acnes* strain, an attenuated protein of said strain, or combination thereof identified to be specific to a subject based on 16S rDNA sequence analysis of the strains of *P. acnes* affecting said subject.

With regard to the vaccines, said heat inactivated *P. acnes* strain, attenuated protein, or combination thereof may be specific for at least one of unique genomic loci, regions, or sequences identified for the strains of *P. acnes*. Said heat inactivated *P. acnes* strain, attenuated protein, or combination thereof may be specific for at least one of Locus 1 (SEQ ID NOs 29 and 82-97), Locus 2 (SEQ ID NOs 30 and 98-186), Locus 3 (31 and 187-423), and Locus 4 (32 and 424-434).

In yet another embodiment, the invention provides a method for the personalized treatment of acne comprising determining the strains of *P. acnes* affecting a subject and treating said subject with an active ingredient directed to at least one detected strain of *P. acnes*, wherein the active ingredient comprises a drug targeting specific strains of *P. acnes*, wherein the targeting drug comprises small molecules, antisense molecules, siRNA, biologics, antibodies, and combinations thereof targeting genomic elements specific for strains of *P. acnes* associated with acne.

In yet another embodiment, the invention provides a method for treating acne comprising: administering an effective amount of a probiotic that comprises at least one strain of *P. acnes* that is associated with healthy or normal skin based on its 16S rDNA. Said strain may be an RT6 strain. Said strain may have at least 95% homology to SEQ ID NO:51, SEQ ID NO:52, SEQ ID NO:53, or SEQ ID NO:54, such as at least 99% homology or 100% homology.

In yet another embodiment, the invention provides a method for treating acne comprising: administering an effective amount of a metabolite produced by a strain of *P. acnes* that is associated with healthy or normal skin, wherein said metabolite is selected from the group comprising bacterial culture supernatant, cell lysate, proteins, nucleic acids, lipids, and other bacterial molecules. Said strain may be an RT6 strain. Said strain may have at least 95% homology to SEQ ID NO:51, SEQ ID NO:52, SEQ ID NO:53, or SEQ ID NO:54, such as at least 99% homology or 100% homology.

In yet another embodiment, the invention provides a method for treating acne in a subject comprising: administering an effective amount of a drug specifically targeting RT4, RT5, RT7, RT8, RT9, or RT10, when said subject is determined to possess RT4, RT5, RT7, RT8, RT9, or RT10, respectively. The earlier-described methods may be performed prior to administration of said drug. Said drug may be a small molecule, antisense molecule, siRNA, biologic, antibody, or combination thereof.

In yet another embodiment, the invention provides a composition comprising at least one strain of *P. acnes* that is associated with healthy or normal skin. Said strain may be an RT6 strain. Said strain may have at least 95% homology to SEQ ID NO:51, SEQ ID NO:52, SEQ ID NO:53, or SEQ ID NO:54, such as at least 99% homology or 100% homology.

In yet another embodiment, the invention provides a method for diagnosing IB-3-based acne comprising: obtaining a skin sample from a subject; isolating bacterial DNA from said sample; using one or more primer sets to amplify said DNA; and analyzing said amplified DNA for the presence of a sequence having at least 95% homology with at least one of SEQ ID NOs 55-81, wherein said subject is diagnosed as having IB-3-based acne if the presence of a sequence having at least 95% homology with at least one of SEQ ID NOs 55-81 exists.

In yet another embodiment, the invention provides a method for the personalized treatment of acne comprising determining the strain(s) of acne affecting a subject and administering to said subject an effective amount of at least one phage specifically directed to said strain(s). For example, the subject may be treated with phage directed against an RT4 strain, an RT5 strain, an RT7 strain, and RT8 strain, an RT9 strain, and/or an RT10 strain.

In yet another embodiment, the invention provides a method for treating an individual suffering from acne of microbiome type I comprising administering to said individual an effective amount of a phage, wherein said phage is selected from the group consisting of: PHL113M01 (SEQ ID NO:36), PHL111M01 (SEQ ID NO:33), PHL082M00 (SEQ ID NO:47), PHL060L00 (SEQ ID NO:34), PHL067M10 (SEQ ID NO:42), PHL071N05 (SEQ ID NO:41), PHL112N00 (SEQ ID NO:35), PHL037M02 (SEQ ID NO:40), PHL085N00 (SEQ ID NO:46), PHL115M02 (SEQ ID NO:43), PHL085M01 (SEQ ID NO:44), PHL114L00 (SEQ ID NO:37), PHL010M04 (SEQ ID NO:38), and PHL066M04 (SEQ ID NO:39).

In yet another embodiment, the invention provides a method for treating an individual suffering from acne of microbiome type I with IB-3 strain comprising administering to said individual an effective amount of a phage, wherein said phage is selected from the group consisting of: PHL082M00 (SEQ ID NO:47) and PHL071N05 (SEQ ID NO:41).

In yet another embodiment, the invention provides a method for treating an individual suffering from acne of microbiome type II comprising administering to said individual an effective amount of a phage, wherein said phage is selected from the group consisting of: PHL113M01 (SEQ ID NO:36), PHL060L00 (SEQ ID NO:34), PHL112N00 (SEQ ID NO:35), and PHL085M01 (SEQ ID NO:44).

In yet another embodiment, the invention provides a method for treating an individual suffering from acne of microbiome type III or dominant RT8 comprising administering to said individual an effective amount of a phage, wherein said phage is selected from the group consisting of: PHL113M01 (SEQ ID NO:36), PHL111M01 (SEQ ID NO:33), PHL082M00 (SEQ ID NO:47), PHL060L00 (SEQ ID NO:34), PHL067M10 (SEQ ID NO:42), PHL071N05 (SEQ ID NO:41), PHL112N00 (SEQ ID NO:35), PHL037M02 (SEQ ID NO:45), PHL085N00 (SEQ ID NO:46), PHL115M02 (SEQ ID NO:43), PHL085M01 (SEQ ID NO:44), PHL114L00 (SEQ ID NO:37), PHL073M02 (SEQ ID NO:40), PHL010M04 (SEQ ID NO:38), and PHL066M04 (SEQ ID NO:39).

In yet another embodiment, the invention provides a method for treating an individual suffering from acne of microbiome type IV comprising administering to said individual an effective amount of a phage, wherein said phage is selected from the group consisting of: PHL113M01 (SEQ ID NO:36), PHL111M01 (SEQ ID NO:33), PHL082M00 (SEQ ID NO:47), PHL060L00 (SEQ ID NO:34), PHL067M10 (SEQ ID NO:42), PHL071N05 (SEQ ID NO:41), PHL112N00 (SEQ ID NO:35), PHL037M02 (SEQ ID NO:45), PHL085N00 (SEQ ID NO:46), PHL115M02 (SEQ ID NO:43), PHL085M01 (SEQ ID NO:44), PHL114L00 (SEQ ID NO:37), PHL073M02 (SEQ ID NO:40), PHL010M04 (SEQ ID NO:38), and PHL066M04 (SEQ ID NO:39).

In yet another embodiment, the invention provides a method for treating an individual suffering from acne of microbiome type V comprising administering to said individual an effective amount of a phage, wherein said phage is selected from the group consisting of: PHL113M01 (SEQ ID NO:36), PHL111M01 (SEQ ID NO:33), PHL082M00 (SEQ ID NO:47), PHL060L00 (SEQ ID NO:34), PHL067M10 (SEQ ID NO:42), PHL071N05 (SEQ ID NO:41), PHL112N00 (SEQ ID NO:35), PHL037M02 (SEQ ID NO:45), PHL085N00 (SEQ ID NO:46), PHL115M02 (SEQ ID NO:43), PHL085M01 (SEQ ID NO:44), PHL114L00 (SEQ ID NO:37), PHL073M02 (SEQ ID NO:40), PHL010M04 (SEQ ID NO:38), and PHL066M04 (SEQ ID NO:39).

In yet another embodiment, the invention provides a method for treating a *Propionibacterium* humerusii-associated malady comprising administering to said individual an effective amount of a phage, wherein said phage is selected from the group consisting of: PHL113M01 (SEQ ID NO:36), PHL111M01 (SEQ ID NO:33), PHL082M00 (SEQ ID NO:47), PHL067M10 (SEQ ID NO:42), PHL071N05 (SEQ ID NO:41), PHL085N00 (SEQ ID NO:46), PHL085M01 (SEQ ID NO:44), PHL114L00 (SEQ ID NO:37), PHL073M02 (SEQ ID NO:40), and PHL010M04 (SEQ ID NO:38).

In yet another embodiment, the invention provides a kit for diagnosing acne in a subject, wherein said kit comprises: at least one primer selected from the group comprising SEQ ID NOs 11-18, 20, 21, 23, 24, 26, and 27; and instructions for use.

In yet another embodiment, the invention provides a kit for diagnosing acne in a subject, wherein said kit comprises: at least one primer selected from the group comprising SEQ ID NOs 11-18, 20, 21, 23, 24, 26, and 27; at least one probe selected from the group comprising SEQ ID NOs 19, 22, 25, and 28; and instructions for use.

Nucleotide, polynucleotide, or nucleic acid sequence will be understood to mean both a double-stranded or single-stranded DNA in the monomeric and dimeric forms and the transcription products of said DNAs.

Homologous nucleotide sequence means a nucleotide sequence having at least a percentage identity with the bases of a nucleotide sequence according to the invention of at least 80%, preferably 90%, 95%, 96%, 97%, 98%, 99% or 100%. This percentage is statistical and the differences between two nucleotide sequences may be determined at random or over the whole of their length.

The invention comprises the polypeptides encoded by a nucleotide sequence according to the invention, including a polypeptide whose sequence is represented by a fragment. Herein, the terms polypeptide, peptide, and protein are interchangeable.

Polypeptides allow monoclonal or polyclonal antibodies to be prepared which are characterized in that they specifically recognize the polypeptides. The invention relates to mono- or polyclonal antibodies or their fragments, or chimeric antibodies, characterized in that they are capable of specifically recognizing a polypeptide.

Polypeptides used in vaccine compositions according to the invention may be selected by techniques known to the person skilled in the art such as, for example, depending on the capacity of said polypeptides to stimulate the T cells, which is translated, for example, by their proliferation or the secretion of interleukins, and which leads to the production of antibodies directed against said polypeptides. Vaccine combinations will preferably be combined with a pharmaceutically acceptable vehicle and, if need be, with one or more adjuvants of the appropriate immunity. Pharmaceutically acceptable vehicle means a compound or a combination of compounds that does not provoke secondary reactions and which allows, for example, the facilitation of the administration of the active compound, an increase in its duration of life and/or its efficacy in the body, an increase in its solubility in solution, or an improvement in its conservation.

Applicants identified ten major lineages of *Propionibacterium acnes* and five major microbiome types in the human pilosebaceous unit ("pore"), where acne arises. Some of the P. acnes lineages and microbiome types are highly enriched in acne patients and some are associated with healthy skin. The unique genomic components of each major lineage, including a linear plasmid that is unique to acne-associated lineages, have been identified. This information is used to, for example: (1) for a method/kit to isolate bacterial DNA/RNA from pilosebaceous units for downstream analysis: (2) rapidly and accurately detect/diagnose/identify the microbiome type of the affected subject and the major strains of P. acnes present in the pores of the affected subject; (3) develop vaccines against acne-associated P. acnes strains; (4) develop probiotics using the strains associated with healthy skin in topical creams, solutions, and the like; (5) develop drugs, including small molecules, biologics, and antibodies targeting the genetic elements and biological pathways unique to the P. acnes strains associated with acne, and (6) to develop bacteriophage-based strain specific therapy to treat acne.

Once the microbiome type of a subject affected with acne is diagnosed, several approaches described below may be used formulate an effective treatment plan. For example, if the subjects have microbiome types IV or V, or are dominated by P. acnes RT10 strains, it is less likely that antibiotic treatment will succeed because these strains are antibiotic resistant. However, other method treatments remain available, such as retinoids.

According to one embodiment of the invention, in a case where the subject has the virulent ribotypes, including RT4, RT5, and RT8, target specific drugs including small molecules, biologics, and antibodies may be more effective treatments. In a preferred embodiment of the invention, such a patient may be treated with antibodies targeting the genetic elements and biological pathways that are unique to P. acnes strains associated with acne.

According to another embodiment of the invention, in a case where the dominant P. acnes strains affecting the subject do not harbor a set of CRISPR/Cas, the additional treatment of phage therapy may be more effective.

The present invention also pertains to alternative treatment strategies for acne treatment to balance the relative abundance of P. acnes strains by promoting the growth of health-associated strains.

The present invention pertains to methods and kits to isolate bacterial DNA/RNA from pores of affected subjects for downstream genetic analysis. More specifically, the present invention pertains to protocols for the extraction of bacterial genomic DNA and RNA from microcomedone spamples. In one particular embodiment of the invention, Biore® Deep Cleansing Pore Strips may be used to sample the bacteria from a subject. Genomic DNA may be extracted according to methods known in the art. For example, the QIAamp DNA Micro Kit (Qiagen) is a commercially available kit that may be used to extract genomic DNA from the supernatant obtained by lysing cells/microcomedones using a beadbeater.

The present invention also pertains to fast and accurate methods and kits for the detection and/or diagnosis of microbiome types in affected subjects. The microbiome typing/microbiome-specific treatment is based on ten major lineages of P. acnes strains and five major microbiome types in the human pilosebaceous unit found through a comprehensive metagenomic analysis using full length 16S rDNA sequencing.

Indeed, samples were PCR-amplified using 16S rDNA specific primers with the following sequences: 27f-MP 5'AGRGTTTGATCMTGGCTCAG-3' and 1492r-MP 5'-TACGGYTACCTTGTTAYGACTT-3'. Optionally, following gel purification, the 1.4 Kb product is excised and further purified using, for example, a Quigen QlAquick Gel Extraction Kit. The purified product is cloned into OneShot E coli. cells using, for example, a TOPO TA cloning kit from Invitrogen. Sequencing is done with a universal forward, universal reverse, and for a subset, internal 16S rDNA primer 907R with sequences of TGTAAAACGACGGCCAGT (forward), CAG-GAAACAGCTATGACC (reverse), and CCGTCAAT-TCCTTTRAGTTT (907R). Sequence reactions were loaded on ABI 3730 machines from ABI on 50 cm arrays with a long read run module.

Each lineage of P. acnes has unique genomic loci, regions, and sequences. Accordingly, specific primers may be generated to target the lineage-specific genomic regions to detect the presence or absence of each lineage, as well as the relative amount of each lineage using methods known in the art, such as PCR/qPCR. This occurs within several hours of obtaining the samples. Prior to Applicants' invention, this required much more time—often weeks using culture-based methods. According to one embodiment of the invention, affected subjects are grouped for microbiome specific treatments based on these diagnoses.

According to the methods of the present invention, unique genomic loci 1, 2, and 3 for strains of ribotypes 4 and 5 have been shown to be associated with acne. Using specific primers targeting for loci 1, 2 and 3, lineages that contain these loci can be distinguished from lineages that lack these loci. In addition, using PCR/qPCR techniques, the relative abundance of each strain may also be detected. Analysis of a mock community has shown that isolates with loci 1, 2 and 3 in an abundance of 7.5% or higher in the microbiome may be detected using these techniques. Given the sensitivity of qPCR, lower abundance levels to a few DNA copies may also be detectable.

It has previously been reported that heat inactivation of P. acnes may be an effective means of developing P. acnes-based vaccines. See T. Nakatsuji et al., 128(10) J. Invest. Dermatol. 2451-2457 (October 2008). In one aspect of the present invention, vaccines are developed against acne-associated P. acnes strains. In another aspect of the present invention, personalized vaccines are developed against acne-associated P. acnes strains. In yet another aspect of the present invention, vaccines are developed against acne-associated P. acnes strains using inactive P. acnes strains or heat attenuated proteins. Strains suitable for use as vaccines may be identified based on 16S rDNA sequencing, identifying lineages of P. acnes strains associated with acne, and the unique genomic loci, regions, and sequences for each lineage to specifically target strains of P. acnes associated with acne and not those strains associated with healthy skin.

According to methods described above, it has been discovered that P. acnes strains with ribotypes 4, 5, 7, 8, 9, and 10 are highly associated with acne. In one embodiment of the present invention, a vaccine is raised against these individual strains separately or in combination. Similarly, the genes in loci 1, 2, and 3 may be targets for vaccination because these loci are unique to ribotypes 4 and 5, and are not found in commensal strains. Locus 4, which is unique to ribotype 8 may also serve as a potential target for vaccine therapy. The list of genes encoded in loci 1, 2, 3, and 4 are shown in Table 3.

The present invention also pertains to probiotics developed using P. acnes strains associated with healthy skin in medicines, compositions, topical creams, solutions, or other cosmetic products. Probiotics have, in the past, been used in topical creams. PROBIOTIC LAB™ announced that mixture of 14 specific strains of bacteria was used for treatment of cystic acne (found on the World Wide Web at probioticlab.com/aboutusprobioticlab.html). Probiotic skin care/DERMBIOTIX has a product line—Probiotic Collagen Complex (PC3), which is claimed to have targeted anti-aging benefits to the skin. However, this is not targeted to acne treatment. Probiotic Collagen Complex (PC3) infuses the skin with the positive bacteria required to effectively combat and eradicate excess negative bacteria caused by external factors (found on the World Wide Web at dermbiotix.com). However, prior to the present invention there existed no skin probiotic product reported for acne treatment using *P. acnes* strains associated with healthy/normal skin. In one aspect of the present invention, skin probiotics are developed for acne treatment using *P. acnes* strains associated with healthy/normal skin. In another aspect of the present invention, skin probiotics are developed for acne treatment using *P. acnes* strains associated with healthy/normal skin based on the 16S rDNA sequencing.

In one particular embodiment of the present invention the RT6 lineage of *P. acnes* and associated with healthy skin is used as a topical product. In yet another embodiment of the present invention the RT6 lineage of *P. acnes* is used by inoculating this isolate on the human skin in order to compete off the acne associated strains. In another embodiment, molecules, including proteins, nucleic acids, lipids, and other metabolites, supernatant of cultures, and/or cell lysate of these strains may be used at probiotics.

The present invention also pertains to drugs targeting acne associated *P. acnes* strains. This is based upon multiple genome comparison of *P. acnes* in combination with 16S rDNA metagenomic analysis, thereby identifying certain strains and genomic variations associated with acne. Drugs intended to target acne associated *P. acnes* include custom designed small molecules, antisense molecules, siRNA molecules, biologics, and antibodies targeting genomic elements specific for strains which are associated with acne. Antisense RNA, antibodies, or small molecules can be designed targeting loci 1, 2, 3, and 4. Strains with ribotypes 4, 5, and 10 are antibiotic resistant. Thus, there is a need in the art for new antibiotics targeting ribotypes 4, 5, and 10.

The present invention also pertains to personalized phage therapy for subjects affected with acne comprising phages specific to certain strains of *P. acnes*. Certain companies provide phage therapy for acne patients, such as the Phage Therapy Center™ found on the World Wide Web at phagetherapycenter.com/pii/PatientServlet?command=static_home). However, such companies provide no information on the bacterial host specificity of the phages used for the therapy. *P. acnes* is commensal and some strains play a protective role for hosts. In one embodiment of the invention, personalized phage therapies include a selections of phages targeting *P. acnes* strains that have been shown to lack a protective role for subjects affected by acne. In yet another embodiment of the invention, personalized phage therapy may be developed according to their bacterial host specificity of the phages to target specific strains of *P. acnes*, leaving health associated strains intact. In addition, it is possible to identify the structure of *P. acnes* lineages of the affected subjects and use that structure to predict resistance to phage infection or plasmid conjugation to better target specific phage therapies. For example, *P. acnes* lineages RT2 and RT6 have a CRISPR/Cas structure, indicating they have resistance against certain phage infection and plasmid conjugation. Table 13 shows the sensitivity and resistance of specific *P. acnes* strains to specific *P. acnes* phages.

The invention is described in more detail in the following illustrative examples. Although the examples may represent only selected embodiments of the invention, the following examples are illustrative only and in no way limiting.

EXAMPLES

Example 1—Analysis of *Propionibacterium Acnes* Strain Populations in the Human Skin Microbiome Associated with Acne The human skin microbiome plays important roles in skin health and disease. However, prior to Applicants' invention the bacterial population structure and diversity at the strain level was poorly understood. The inventors compared the skin microbiome at the strain level and genome level of *Propionibacterium acnes*, a dominant skin commensal, between 49 acne patients and 52 healthy individuals by sampling the pilosebaceous units on their noses. Metagenomic analysis demonstrated that while the relative abundances of *P. acnes* were similar, the strain population structures were significantly different in the two cohorts. Certain strains were highly associated with acne and other strains were enriched in healthy skin. By sequencing 66 novel *P. acnes* strains and comparing 71 *P. acnes* genomes, the inventors identified potential genetic determinants of various *P. acnes* strains in association with acne or health. The analysis indicates that acquired DNA sequences and bacterial immune elements may play roles in determining virulence properties of *P. acnes* strains and some may be targets for therapeutic interventions. This study demonstrates a previously-unreported paradigm of commensal strain populations that explains the pathogenesis of human diseases. It underscores the importance of strain level analysis of the human microbiome to define the role of commensals in health and disease.

Background

The diversity of the human microbiota at the strain level and its association with human health and disease are largely unknown. However, many studies had shown that microbe-related human diseases are often caused by certain strains of a species, rather than the entire species being pathogenic. Examples include methicillin-resistant *Staphylococcus aureus* (MRSA) (Chambers and Deleo, 2009; Chen et al., 2010; Hansra and Shinkai) and *Escherichia coli* O157 (Chase-Topping et al., 2008; Tarr et al., 2005). Acne vulgaris (commonly called acne) is one of the most common skin diseases with a prevalence of up to 85% of teenagers and 11 of adults (White, 1998). Although the etiology and pathogenesis of acne are still unclear, microbial involvement is considered one of the main mechanisms contributing to the development of acne (Bojar and Holland, 2004; Cunliffe, 2002). In particular, *Propionibacterium acnes* has been hypothesized to be an important pathogenic factor (Webster, 1995). Antibiotic therapy targeting *P. acnes* has been a mainstay treatment for more than 30 years (Leyden, 2001). However, despite decades of study, it remained unclear as to how *P. acnes* contributes to acne pathogenesis while being a major commensal of the normal skin flora (Bek-Thomsen et al., 2008; Cogen et al., 2008; Costello et al., 2009; Dominguez-Bello et al., 2010; Fierer et al., 2008; Gao et al., 2007; Grice et al., 2009). Whether *P. acnes* protects the human skin as a commensal bacterium or functions as a pathogenic factor in acne, or both, remained to be elucidated.

Thus, Applicants compared the skin microbiome at the strain level and genome level in 49 acne patients and 52 normal individuals using a combination of metagenomics and genome sequencing. First, for each sample, 16S ribosomal DNA (rDNA) was amplified, approximately 400 clones were sequenced, and an average of 311 nearly full length 16S rDNA sequences were analyzed. The population structure of *P. acnes* strains was determined in each sample. Second, each *P. acnes* strain was assigned an "acne index" by calculating its prevalence in acne patients based on the 16S rDNA metagenomic data. The *P. acnes* strains associated with the acne patient group were identified, as well as the strains enriched in the individuals with normal skin. This metagenomic approach is fundamentally different than prior approaches in determining disease associations; it is more powerful and less biased than traditional methods by bypassing the biases and selection in strain isolation and culturing. Lastly, 66 novel *P. acnes* strains were sequenced and 71 *P. acnes* genomes compared covering the major lineages of *P. acnes* found in the skin microbiota. By combining a metagenomic study of the skin microbiome and genome sequencing of this major skin commensal, Applicants' study provided insight into bacterial genetic determinants in acne pathogenesis and emphasizes the importance of strain level analysis of the human microbiome to understand the role of commensals in health and disease.

Results

*P. acnes* Dominates the Pilosebaceous Unit

Applicants characterized the microbiome in pilosebaceous units ("pores") on the nose collected from 49 acne patients and 52 individuals with normal skin. Nearly full length 16S rDNA sequences were obtained using Sanger method, which permitted analyzing the *P. acnes* at the strain level. After quality filtering, the final dataset contained 31,461 16S rDNA sequences ranging from position 29 to position 1483. 27,358 of the sequences matched to *P. acnes* with greater than 99% identity. The data demonstrated that *P. acnes* dominates the microbiota of pilosebaceous units, accounting for 87% of the clones (FIG. 1). Other commonly found species in pilosebaceous units included *Staphylococcus epidermidis*, *Propionibacterium humerusii*, and *Propionibacterium granulosum*, each representing 1%-2.3% of the total clones. A total of 536 species level operational taxonomic units (SLOTUs) belonging to 42 genera and six phyla were identified in the samples (Table 1).

TABLE 1

Six phyla and 42 genera found in pilosebaceous units.

| Phylum | Genus | Phylum | Genus |
|---|---|---|---|
| Actinobacteria | Actinobaculum | Bacteroidetes | Chryseobacterium |
| | Corynebacterium | | Niastella |
| | Gordonia | | Parabacteroides |
| | Kocuria | | Prevotella |
| | Microbacterium | Proteobacteria | Caulobacteraceae |
| | Propionibacterium | | Citrobacter |
| Firmicutes | Anaerococcus | | Cupriavidus |
| | Anoxybacillus | | Delftia |
| | Bacillus | | Diaphorobacter |
| | Enterococcus | | Haemophilus |
| | Erysipelotlarix | | Klebsiella |
| | Finegoldia | | Massilia |
| | Gemella | | Neisseriaceae |
| | Lactobacillus | | Novosphingobium |
| | Paenibacillus | | Pelomonas |

TABLE 1-continued

Six phyla and 42 genera found in pilosebaceous units.

| Phylum | Genus | Phylum | Genus |
|---|---|---|---|
| | Peptoniphilus | | Phyllobacterium |
| | Peptostreptococcaceae | | Ralstonia |
| | | | Shigella |
| | Ruminococcaceae | | Sphingomonas |
| | Ruminococcaceae | | Stenotrophomonas |
| | Staphylococcus | | |
| | Streptococcus | Cyanobacteria | Streptophyta |
| Fusobacteria | Fusobacterium | | |

To bypass the potential biases due to PCR amplification and due to uneven numbers of 16S rDNA gene copies among different species, a metagenomic shotgun sequencing of the total DNA pooled from the pilosebaceous unit samples of 22 additional normal individuals was performed. Microbial species were identified by mapping metagenomic sequences to reference genomes. The results confirmed that *P. acnes* was the most abundant species (89%) (FIG. 1). This is consistent with the results obtained from 16S rDNA sequencing (87%).

For the 16S rRNA sequence, positions 27 to 1492 were PCR amplified. Yet, when analyzing the sequence only positions 29-1483 are studied. The numbering of positions is based on the *E. coli* system of nomenclature. Thus, the sequences between 29-1483 are important for determining the ribotype (there are many ribotypes, not just 10). As for the top 10 ribotypes, sequences between positions 529-1336 of the 16A rRNA are sufficient.

Different *P. acnes* Strain Populations in Acne

Figure 2:
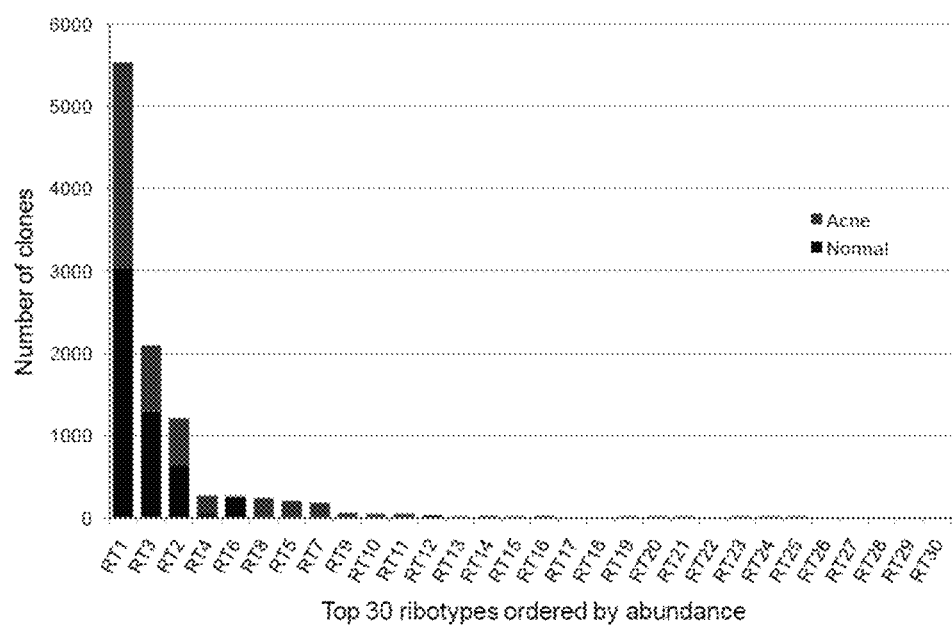
FIG. 2 shows that the rank abundance of *P. acnes* ribotypes shows a distribution similar to that seen at the higher taxonomic levels. A few highly-abundant ribotypes and a large number of rare ribotypes were observed in the samples. Some ribotypes were highly enriched in acne patients. Only the top 30 most abundant ribotypes are reflected in FIG. 2.

There was no statistically significant difference in the relative abundance of *P. acnes* when comparing acne patients and normal individuals. It was then examined whether there were differences at the strain level of *P. acnes* by extensively analyzing the *P. acnes* 16S rDNA sequences. Herein, each unique 16S rDNA sequence as a 16S rDNA allele type is called a ribotype (RT). The most abundant *P. acnes* sequence was defined as ribotype 1 (RT1) (SEQ ID NO:1). All other defined ribotypes have 99% or greater sequence identity to RT1. Similar to the distributions seen at higher taxonomical levels (Bik et al.), at the strain level a few ribotypes were highly abundant in the samples with a significant number of rare ribotypes (FIG. 2). After careful examination of the sequence chromatograms and manual correction of the sequences, a total of 11,009 ribotypes were assigned to the *P. acnes* 16S rDNA sequences. Most of the minor ribotypes were singletons. On average, each individual harbored 3±2 *P. acnes* ribotypes with three or more clones. Based on the genome sequences described below, all the sequenced *P. acnes* strains have three identical copies of 16S rDNA genes (see note below). This allowed the *P. acnes* strain populations in individuals based on the 16S rDNA sequences to be compared. The top ten major ribotypes with more than 60 clones and found in multiple subjects are shown in Table 2:

TABLE 2

Top ten most abundant ribotypes found in pilosebaceous units

| Ribotype | Nucleotide changes from RT1 | Number of subjects | Number of clones | Percentage of clones from acne patients[a] | Percentage of clones from normal individuals[b] | p-value[c] |
|---|---|---|---|---|---|---|
| RT1 | — | 90 | 5536 | 48% | 52% | 0.84 |
| RT2 | T854C | 48 | 1213 | 51% | 49% | 0.36 |
| RT3 | T1007C | 60 | 2104 | 40% | 60% | 0.092 |
| RT4 | G1058C, A1201C | 23 | 275 | 84% | 16% | 0.049 |
| RT5 | G1058C | 15 | 205 | 99% | 1% | 0.00050 |
| RT6 | T854C, C1336T | 11 | 262 | 1% | 99% | 0.025 |
| RT7 | G529A | 10 | 188 | 99% | 1% | 0.12 |
| RT8 | G1004A, T1007C | 5 | 239 | 100% | 0% | 0.024 |
| RT9 | G1268A | 4 | 68 | 99% | 1% | 0.29 |
| RT10 | T554C, G1058C | 5 | 61 | 100% | 0% | 0.024 |

[a] The percentage was calculated after the number of clones of each ribotype was normalized by the total number of clones in acne patients (acne index).
[b] The percentage was calculated after the number of clones of each ribotype was normalized by the total number of clones in normal individuals.
[c] Mann-Whitney-Wilcoxon rank sum test.

Analysis of the top ten ribotypes showed both disease-specific and health-specific associations. The three most abundant ribotypes (RT1, RT2 and RT3) were fairly evenly distributed among acne and normal individuals. However, the next seven major ribotypes were significantly skewed in their distributions (Table 2). Ribotypes 4, 5, 7, 8, 9, and 10 were found predominantly in acne patients, with four of these six statistically significantly enriched in acne ($p<0.05$, Wilcoxon test). Ribotypes 4, 5, and 10 contain a nucleotide substitution G1058C in the 16S rDNA sequences, which has previously been shown to confer increased resistance to tetracycline (Ross et al., 1998; Ross et al., 2001). However, only a small percentage of the subjects in our study harboring these ribotypes had been treated with antibiotics (FIG. 3), therefore enrichment of these three ribotypes in the acne group was not correlated with antibiotic treatment. This is consistent with previous studies, which showed that previous use of antibiotics was not always associated with the presence of antibiotic resistant strains and that some patients who were not previously treated with antibiotics harbored strains already resistant to antibiotics (Coates et al., 2002; Dreno et al., 2001). One ribotype, RT6, although detected in only 11 subjects, was strongly associated with normal skin ($p=0.025$, Wilcoxon test) (Table 2). Its relative abundance in the normal group was similar to that found in the healthy cohort data from the Human Microbiome Project (HMP) (see FIG. 3). The percentage of positive subjects (11/52) was similar as well. Three of the 14 HMP subjects had RT6 found in the anterior nares, and one additional subject had RT6 in the left retroauricular crease.

Figure 4:
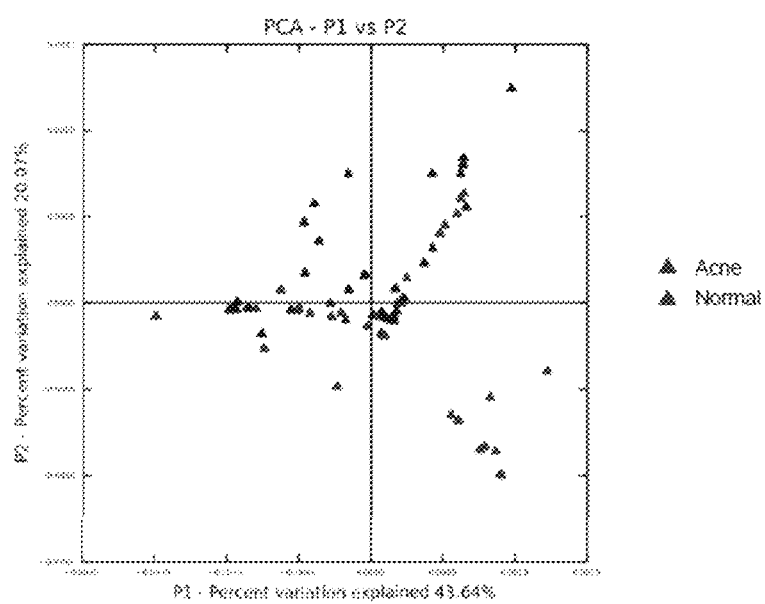
FIG. 4 shows that *P. acnes* population structures differ in acne and normal skin. *P. acnes* populations from samples were clustered using principal coordinates analysis of the weighted UniFrac distance matrix for the top ten most abundant ribotypes. The principal coordinate 1 (P1) explains 43.64% of the variation and P2 explains 20.07% of the variation. The analysis was performed using QIIME (Caporaso et al. 2010).

Based on the distributions of the top ten ribotypes, statistical analysis using several different tests showed significant differences in *P. acnes* population structure between acne and normal skin (FIG. 4). This is consistent with a principal coordinate analysis, where acne samples and normal skin samples were separated by mostly principal coordinates 1 and 2 (FIG. 4), explaining 44% and 20% of the variation, respectively.

Figure 5:
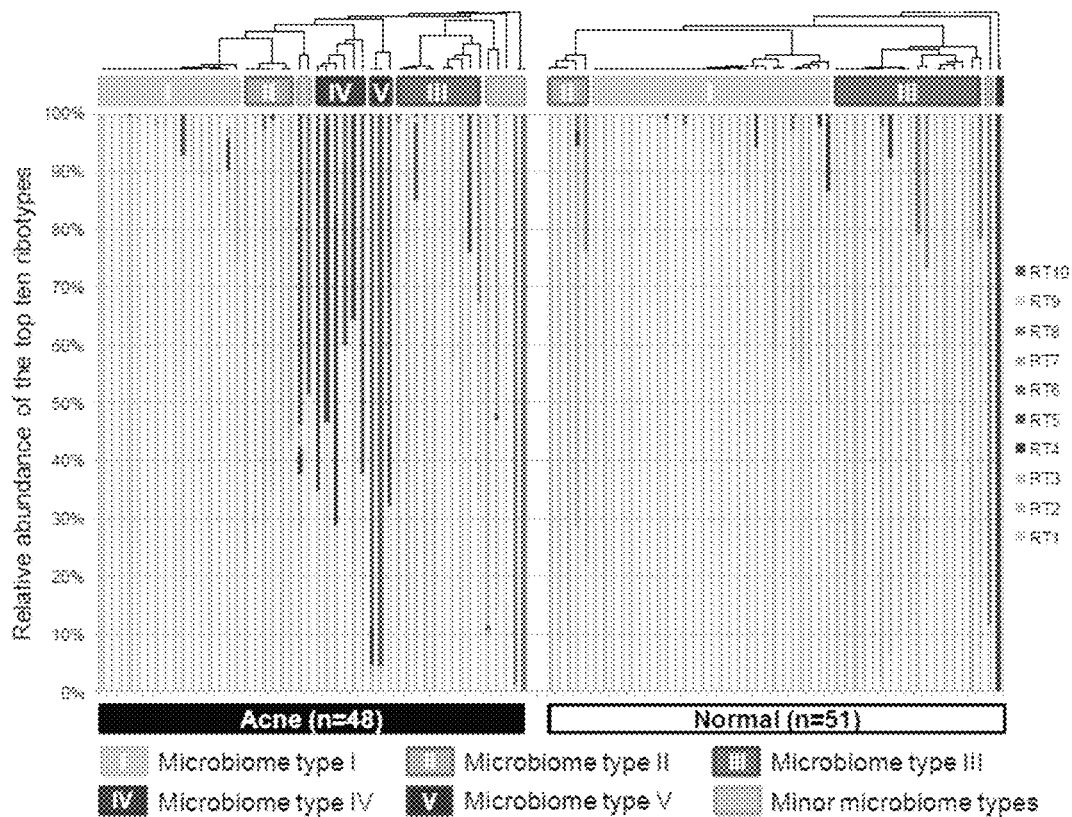
FIG. 5 shows the distribution of the top ten most abundant *P. acnes* ribotypes in acne patients and individuals with normal skin. Each column represents the percentage of the top ten ribotypes identified in each subject. The average *P. acnes* clone number per subject was 262 and the average clone number of top ten ribotypes was 100. Five major microbiome types at the *P. acnes* strain level were observed in the data. Types IV and V were mostly found in acne patients. Two samples (one from acne, one from normal skin) with fewer than 50 *P. acnes* 16S rDNA sequences are not displayed.
Figure 6:
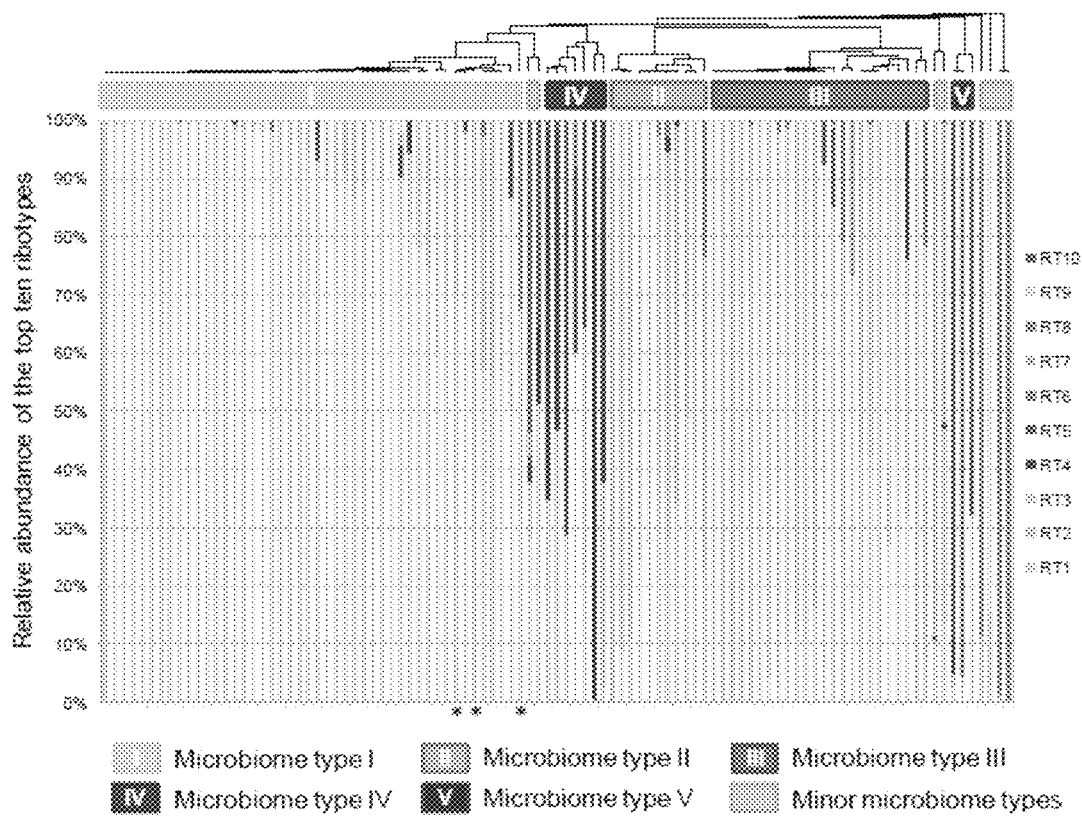
FIG. 6 shows the distribution of the top ten most abundant *P. acnes* ribotypes in all samples without separating the two groups of acne and normal skin. Each column represents the percentage of the top ten ribotypes identified in each sample. When all samples were clustered, the same five major microbiome types at the *P. acnes* strain level were observed, indicating that microbiome classification does not depend on the states of the disease. Only three out of 99 samples were clustered differently compared to the one shown in FIG. 5 (marked with asterisks). Two samples, one from acne and one from normal skin, with fewer than 50 *P. acnes* 16S rDNA sequences are not shown.

To examine whether different individuals share similar *P. acnes* population structures, the samples were clustered based on the relative abundances of the top ten ribotypes. Five main microbiome types were observed at the *P. acnes* strain level (microbiome types I to V). Types IV and V, which are dominated by *P. acnes* RT4 and RT5, respectively, were mainly found in acne patients (FIGS. 5 and 6). The same five main microbiome types were observed in the HMP data and the data from Grice et al. (Grice et al., 2009) (see FIG. 7).

Genome Sequence Analysis of 71 *P. acnes* Strains

Figure 8:
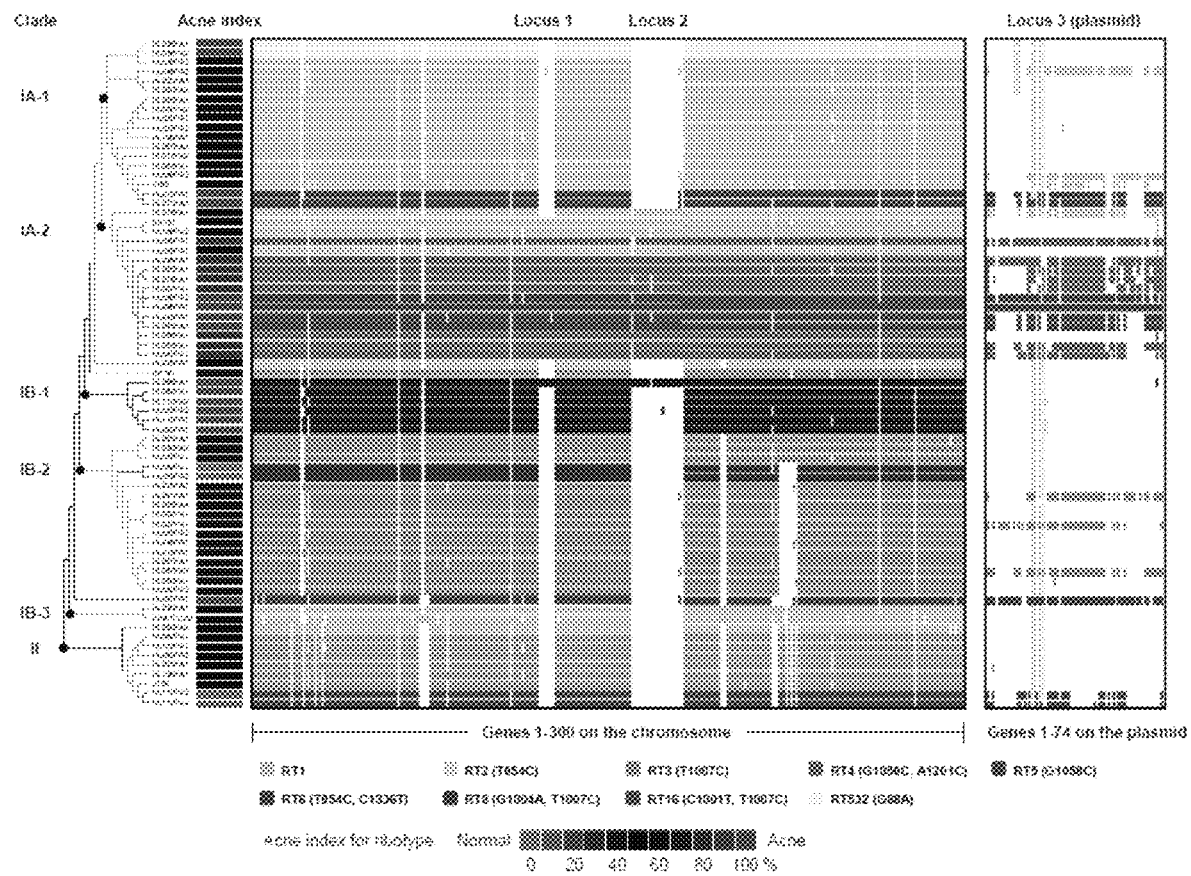
FIG. 8 indicates that the genome comparison of 71 *P. acnes* strains showed that the genomes of RT4 and RT5 are distinct from others. Two chromosomal regions, loci 1 and 2, are unique to clade IA-2 and one other genome HL086PA1. Clade IA-2 consists of mainly RT4 and RT5 that were highly enriched in acne. The presence of a plasmid (locus 3) is also characteristic of RT4 and RT5. Each row represents a *P. acnes* genome colored according to the ribotypes. Rows are ordered by the phylogeny calculated based on the SNPs in the *P. acnes* core genome. Only the topology is shown. The clades were named based on their recA types (IA, IB and II). Columns represent predicted open reading frames (ORFs) in the genomes and are ordered by ORF positions along the finished genome HL096PA1, which encodes a 55 Kb plasmid. Only the first 300 ORFs on the chromosome (on the left) and all the ORFs on the plasmid (on the right) are shown. The colored plasmid regions represent genes on contigs that match exclusively to the HL096PA1 plasmid region. The genes that fall on contigs that clearly extend beyond the plasmid region are likely to be chromosomally located and are colored in grey. Acne index for the ribotypes was calculated based on the percentage of clones of each ribotype found in acne as shown in column 5 in Table 2.
Figure 9:
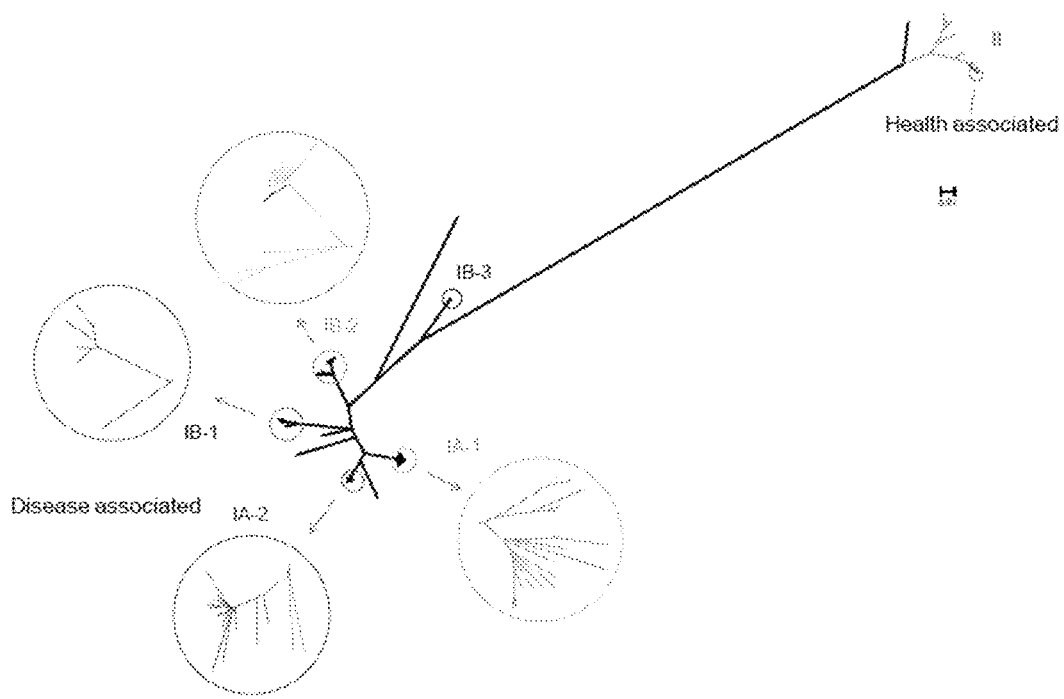
FIG. 9 shows the phylogentic tree constructed based on the 96,887 SNPs in *P. acnes* core genome, which shows that the 71 genomes cluster into distinct clades, consistent with recA types that have been used to classify *P. acnes* strains. The 16S ribotypes of the genomes represent the relationship of the lineages to a large extent. At one end of the tree, clades IA-2 and IB-1 mainly consist of the ribotypes enriched in acne, and at the other end of the tree, RT6 in clade II was mainly found in healthy subjects. Bootstrap test with 1,000 replicates were performed. The distances between the branches were calculated based on the SNPs in the core genome and do not represent the non-core regions of each genome. The enlarged branches were colored according to the 16S ribotypes as shown in FIG. 8.

All of the top ten most abundant ribotypes differ from RT1 by only one or two nucleotide changes in the 16S rDNA sequence (Table 2). To determine whether such small changes in the 16S rDNA sequence reflect the lineages and evolutionary history at the genome level, 66 *P. acnes* isolates representing major ribotypes 1, 2, 3, 4, 5, 6, and 8 as well as two minor ribotypes, 16 and 532, were selected for genome sequencing. The genomes of these 66 isolates were fully sequenced and assembled to high quality drafts or complete genomes with 50×coverage or more. Five other *P. acnes* genomes, KPA171202 (Bruggemann et al., 2004), J165, J139, SK137, and SK187, were publicly-available and were included in the analysis. A phylogenetic tree based on 96,887 unique single nucleotide polymorphism (SNP) positions in the core genome obtained from these 71 *P. acnes* genomes was constructed. Most of the genomes with the same ribotypes clustered together. The tree indicates that the 16S rDNA ribotypes do represent the relationship of the lineages to a large extent and that 16S rDNA sequence is a useful molecular marker to distinguish major *P. acnes* lineages (FIGS. 8 and 9).

Genetic Elements Detected in *P. acnes*

Figure 10:
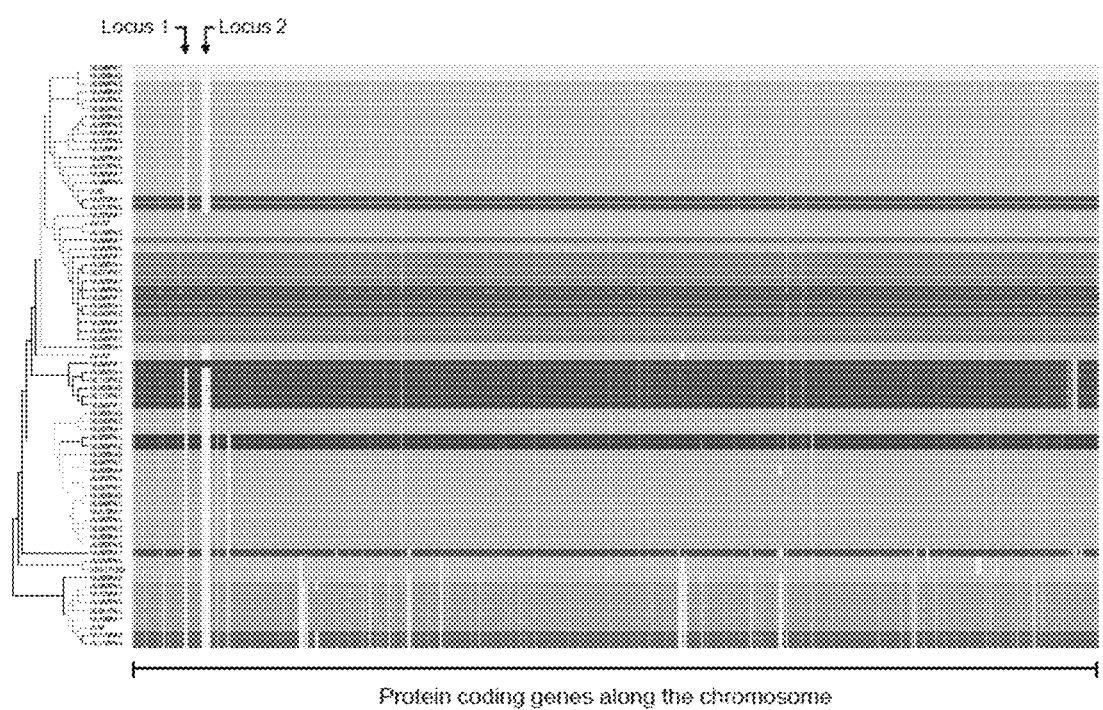
FIG. 10 provides a genome comparison of 71 *P. acnes* strains and shows that the genomes of RT4 and RT5 are distinct from others. All of the predicted open reading frames (ORFs) encoded on the chromosome are shown. Each row represents a *P. acnes* genome colored according to the ribotypes. Rows are ordered by the phylogeny calculated based on the SNPs in *P. acnes* core genome. Only the topology is shown. Columns represent ORFs in the genomes and are ordered by their positions along the finished genome HL096PA1. Loci 1 and 2, which are unique to mainly RT4 and RT5 strains, and locus 4, which is unique to mainly RT8 strains, can be seen in the figure.
Figure 11:
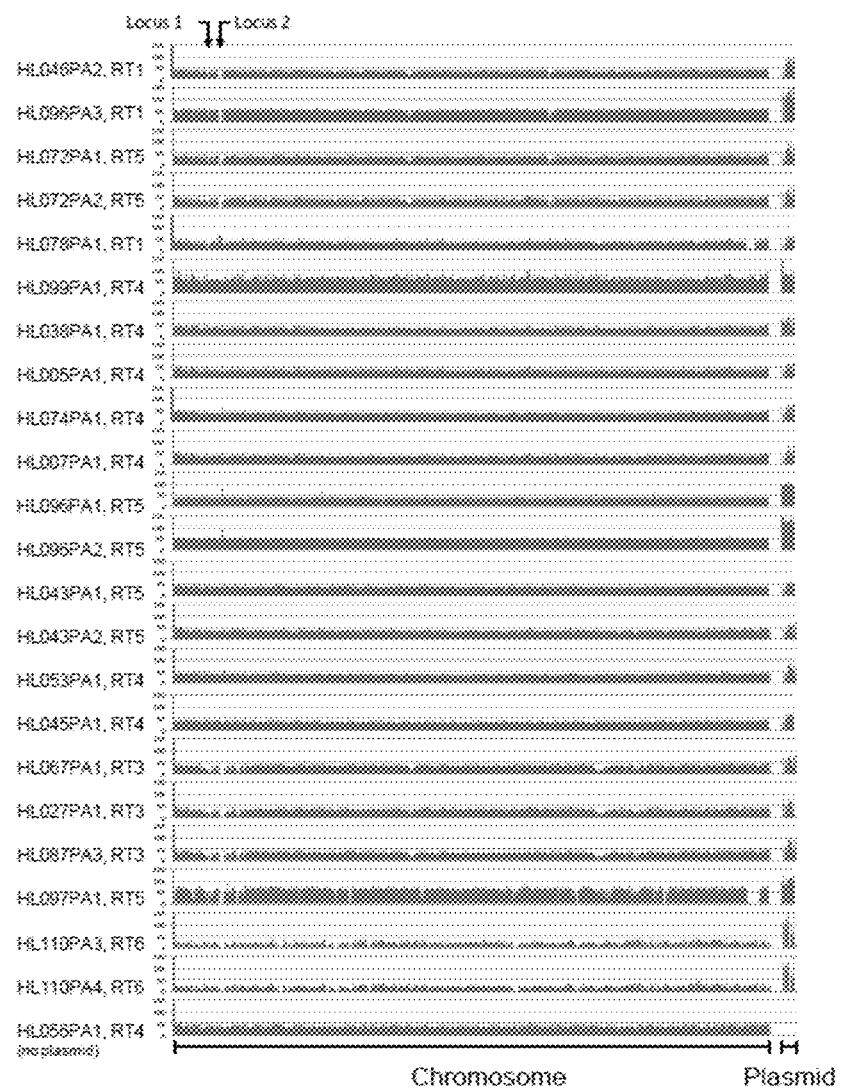
FIG. 11 provides a sequence coverage comparison between the chromosome and the plasmid region in all genomes harboring a putative plasmid, which shows that the copy number of plasmid ranges from 1 to 3 per genome. The X-axis represents the DNA sequences along the chromosome based on the coordinates of the finished genome HL096PA1, followed by plasmid sequences. The Y-axis represents the sequence coverage. The genomes were in the same order as in FIG. 8, except HL056PA1 (as a negative control).
Figure 12:
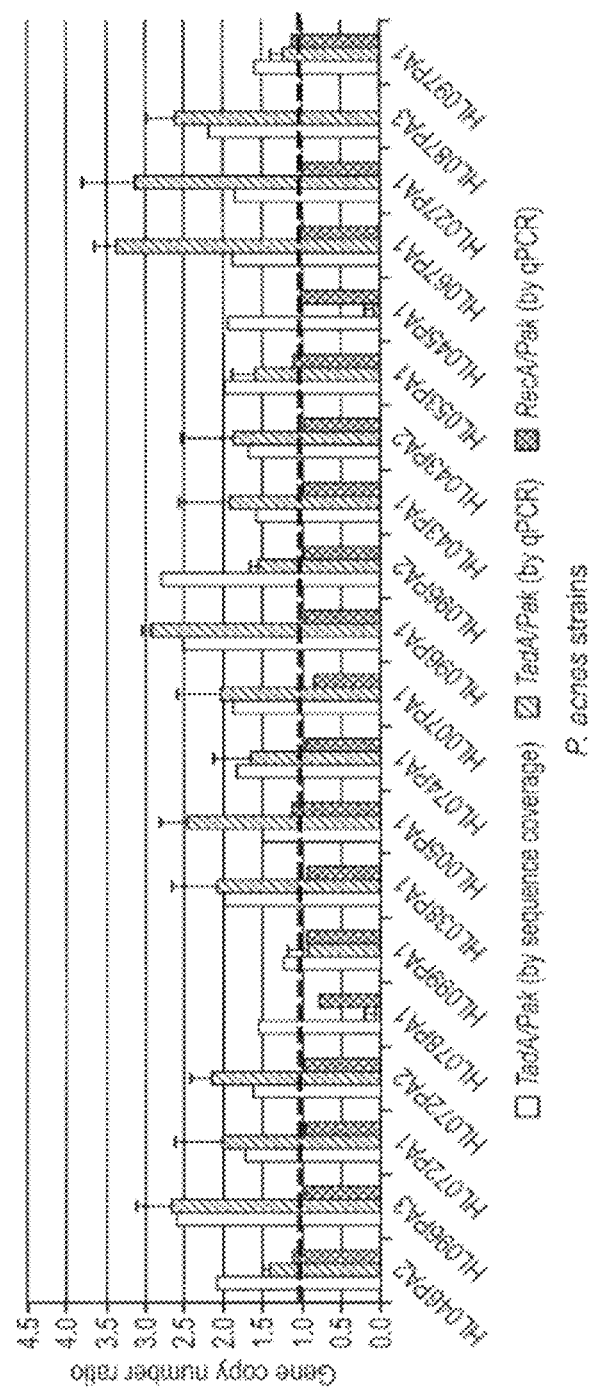
FIG. 12 reflects that quantitative PCR (qPCR) confirmed that the copy number of plasmid in each genome is 1-3 as predicted from sequence coverage comparison. Pak and RecA are housekeeping genes located on the chromosome and TadA is a conserved gene in the Tad locus located on the plasmid. The copy number ratio between TadA and Pak ranges from 1 to 3 in genomes, while the ratio between RecA and Pak is 1 in all the genomes. The TadA gene in HL078PA1 and HL045PA1 had amplification in late cycles in qPCR. Conventional PCR confirmed the amplification of TadA in these two strains, while other strains without the plasmid showed no amplification (data not shown).

A comparative genome analysis among all 71 genomes grouped by ribotypes was performed. The analysis revealed genetic elements by which acne-associated strains could contribute to acne pathogenesis and the elements by which health-associated strains could contribute to maintaining skin health. Specifically, now known are the unique genome regions of RT4 and RT5, which had a strong association with acne, and RT6, which was found enriched in normal skin. Three distinct regions, loci 1, 2, and 3, were found almost exclusively in strains that belong to clade IA-2 in the phylogenetic tree. Clade IA-2 consists of mainly RT4 and RT5 (FIGS. 8 and 10). Loci 1 and 2 are located on the chromosome. Locus 1 contains prophage-related genes and appears to be a genomic island. Locus 2 has plasmid integration sites and may be derived from a plasmid sequence. Locus 3 appears to be on a large mobile genetic element, likely a plasmid. The plasmid is approximately 55 Kb long and has inverted terminal repeats according to the finished genome HL096PA1. The sequence data suggest that the plasmid is linear and possibly originated from a phage (Hinnebusch and Tilly (1993)). All but one of the fifteen genomes of RT4 and RT5 have at least 60% of the genes of the plasmid represented, and all of them have regions homologous to the inverted terminal repeats in the plasmid, suggesting that they harbor the same or a similar linear plasmid (FIG. 8). The copy number of the plasmid in the genomes ranges from 1 to 3 based on genome sequencing coverage, which was confirmed by quantitative PCR (FIGS. 11 and 12).

The fact that acne-enriched RT4 and RT5 strains carry a linear plasmid and two unique loci of genomic islands indicates that these plasmid and chromosomal regions play a role in acne pathogenesis. In fact, the linear plasmid encodes a tight adhesion (Tad) locus, which has been suggested to play a role in virulence in other organisms (Kachlany et al., 2000; Schreiner et al., 2003). The complete Tad locus is found in all but one of the fifteen genomes of RT4 and RT5, and is only occasionally found in other ribotypes. Additionally, in locus 2, a Sag gene cluster is encoded, which has been shown to contribute to hemolytic activity in pathogens (Fuller et al., 2002; Humar et al., 2002; Nizet et al., 2000). FIG. 6 summarizes the genes that are mostly unique to RT4 and RT5, several of which play essential roles in virulence in other organisms. Some of these genes encoded in RT4 and RT5 increase virulence, promote stronger adherence to the human host, or induce a pathogenic host immune response.

In the genome comparison analysis, it was found that all the genomes of RT2 and RT6 encode Clustered Regularly Interspaced Short Palindromic Repeats (CRISPR). Among the sequenced genomes, RT2 and RT6 are the only ribotypes encoding CRISPR. CRISPR have been shown to confer protective "immunity" against viruses, phages, and plasmids (Horvath and Barrangou, 2010; Makarova et al., 2011). The CRISPR locus encoded in *P. acnes* consists of a series of cas genes—cas3, cse1, cse2, cse4, cas5e, cse3, cas1, and cas2, which are homologous to the CRISPR locus reported in *E. coli* (Figure S10) and the CRISPR4 locus in *Streptococcus thermophilus* (Horvath and Barrangou, 2010).

CRISPR arrays are composed of a cluster of identical repetitive sequences separated by spacer sequences of similar length but with different nucleotide sequences. It has been found that spacer sequences are identical or with one or two mismatches to phage or plasmid DNA sequences. A total of 39 spacer sequences were found in eight *P. acnes* strains, 25 of which were unique as shown in Table 3.

TABLE 3

CRISPR spacer sequences found in the genomes of RT2 and RT6

| Ribo-type | Strain | Spacer number | Spacer sequence | BLAST result | Match found |
|---|---|---|---|---|---|
| RT2 | HL001PA1 | 1 | CATGGCCTGCACACCAGGCGCTTTTAGCACCT | No hits | |
| | | 2 | CATGGCCTGCACACCAGGCGCTTTTAGCACCT | No hits | |
| | | 3 | CATGGCCTGCACACCAGGCGCTTTTAGCACCT | No hits | |
| | | 4 | GGCGTATGACGAGTTGTGGTCGGCGTTTCCTC | P. acnes phage PA6 gp15 (minor tail protein) | |
| | | 5 | CGGTGTTAACGGCTTGCCTGGCTTGGATGGAG | No hits | |
| RT2 | HL060PA1 | 1 | CGCCTACCGTCAGCTGACTCACGCCTCCGCGTT | No hits | |
| | | 2 | TCACACCAGTCATCAGCGTCATAGTCCTCTCCG | No hits | |
| RT2 | HL082PA2 | 1 | GGCTCAGCCTCCCCGATGCCTACGCCAAATGG | C. leptum DSM 753 CLOLEP_00129 (cell wall-associated hydrolases (invasion-associated proteins)) | Locus 3 |
| | | 2 | TCACACCAGTCATCAGCGTCATAGTCCTCTCGG | No hits | |
| RT2 | HL103PA1 | 1 | CACCGGGCCCATCCCGCTCGGCCTCCTGAAAGG | C. leptum DSM 753 CLOLEP_00135 | Locus 3 |
| RT2 | HL106PA1 | 1 | GATCGAGTTGGCTGAGTCGAGGTGTTGCGGTT | P. acnes phage PA6 gp16 (conserved protein) | |
| | | | | P. acnes phage PAD20 gp16 | |
| | | 2 | CTGCTCATCGCTCAGCTCCTGCGCCTCATCACA | No hits | |
| | | 3 | CTGCGCCAACAGCCCGCCATTCGATCCGAATACGG | P. acnes phage PA6 gp3 (phage portal protein) | |
| | | | | P. acnes phage PAD20 gp3 | |
| | | 4 | CGCAGCAATCTCAGAAGGCCACACAAGTTCGT | P. acnes phage PA6 gp7 (conserved protein) | |
| | | | | P. acnes phage PAD20 gp7 | |
| | | | | P. acnes phage PAS50 gp7 | |
| | | 5 | CAAATCACCCAAGCCCAACACGCCGCCACCAC | No hits | |
| | | 6 | TGTCACCGATTCAATGTATCTATGAGTGGTGTA | No hits | |
| | | 7 | TTGGGTGGGTGAGGTCGGGTCGTCAGTCATGAG | No hits | |
| | | 8 | GTCGATGTCGAGATTGCCTGGGGGTCCATGTC | Clostridium leptum DSM 753 CLOLEP_00142 | Locus 3 |
| | | 9 | ACGTCGTGAACGTACCCCTTGACGGAGACGGCA | No hits | |
| RT2 | J139 | 1 | CGAGGGCTACCACGTGGTCGATTTGGACTGTCG | C. leptum DSM 753 CLOLEP_00167 | Locus 2 |
| | | | | P. acnes 5K137 HMPREF0675_3193 (domain of unknown function) | |
| | | 2 | CAGGCGCTCCACTCCCTCGCCCTGGCCACCAAC | No hits | |
| RT6 | HL110PA3 | 1 | CTATGTGGACAGTGTTGGTTACTGTGGGGGAA | P. acnes phage PA6 intergenic region between gp45 and gp46 | |
| | HL110PA4 | 2 | GCACTGCACCGATATCGTCGTCGTCGTCACTTG | No hits | |
| | | 3 | CCCAGACAACTTCGACAACCTGTTCAGGGGATG | P. acnes phage PAS50 gp25 | |
| | | 4 | CATGGCTAGCCCGGATTTTTGCTGCCTGAGCG | P. acnes phage PA6 gp34 (mutidrug resistance protein-like transporters) | |
| | | | | P. acnes phage PAD20 gp34 (DNA helicase) | |
| | | 5 | CGGCCTGCGGCAGATTTTGTTGCGTTGAATCC | P. acnes phage PA6 gp14 (tape measure protein) | |
| | | | | P. acnes phage PAD20 gp14 (tape measure protein) | |
| | | | | P. acnes phage PAS50 gp14 (tape measure protein) | |
| | | 6 | CGGGCAGAGGATGTGTTGCTCGTTCCTGGATGG | P. acnes phage PA6 gp32 (CHC2 zinc finger) | |
| | | | | P. acnes phage PAD20 gp32 (DNA primase) | |
| | | | | P. acnes phage PAS50 gp32 (DNA primase) | |

TABLE 3-continued

| Ribotype | Strain | Spacer number | Spacer sequence | BLAST result | Match found |
|---|---|---|---|---|---|
| | | 7 | GTTACGCTGGAACCCCCAATGAACACGCGAGAA | P. acnes phage PAD42 major head protein gene<br>P. acnes phage PAD20 major head protein gene<br>P. acnes phage PAD9 major head protein gene<br>P. acnes phage PA540 major head protein gene<br>P. acnes phage PAS12 major head protein (gene<br>P. acnes phage PAS 10 major head protein gene<br>P. acnes phage PAD21 major head protein gene<br>P. acnes phage PAS2 major head protein gene<br>P. acnes phage PA6 gp6 (Phage capsid family)<br>P. acnes phage PA550 gp6 major head protein gene | |
| | | 8 | CGAGGGCTACCACGTGGTCGATTTGGACTGTCG | C. leptum DSM 753 CLOLEP_00167<br>P. acnes SK137 HMPREF0675_3193 (Domain of unknown function) | Locus 2 |
| | | 9 | CAGGCGCTCCACTCCCTCGCCCTGGCCACCAAC | No hits | |

Abbreviations: BLAST, Basic Local Alignment Search Tool; CRISPR, Clustered Regularly Interspaced Short Palindromic Repeat; C. leptum, Clostridium leptum; P. acnes, Propionibacterium acnes; RT, ribotype.

As expected, most of the identifiable spacers target to known *P. acnes* phage sequences. However, among the unique CRISPR spacer sequences, one matched locus 2 on the chromosome and three matched the plasmid region (locus 3) in *P. acnes* genomes of mainly RT4 and RT5. This suggests that these loci may have been acquired by RT4 and RT5 strains, while the genomes of RT2 and RT6 may be capable of protecting against the invasion of the plasmids or other foreign DNA through the CRISPR mechanism.

Discussion

The foregoing study of the human skin microbiome associated with acne provides the first portrait of the microbiota of pilosebaceous units at the bacterial strain level. Since *P. acnes* is the major skin commensal bacterium found in both acne and healthy skin, this strain-level analysis is important to help understand the role of *P. acnes* in acne pathogenesis and in skin health. A strong association between strains of RT4 and RT5 with acne and a strong association between strains of RT6 and healthy skin, each with unique genetic elements, has been shown. Other *P. acnes* strains, including ribotypes 7, 8, 9, and 10, or interactions among different strains, may also contribute to the development of the disease. In addition, host factors, such as hormone level, sebum production, and physical changes in the pilosebaceous unit, may also play a role in acne pathogenesis.

The foregoing metagenomic approach in revealing the association of *P. acnes* strains with the disease or health is more powerful than previous studies using traditional methods (Lomholt and Kilian, 2010; McDowell et al., 2011). Because the skin microbiota of each individual and each skin site may harbor "good," "neutral," and "bad" strains at the same time, which may have different growth rates under in vitro culturing conditions, culturing a few isolates from a disease lesion or healthy skin site may not provide an accurate and unbiased measurement of the association of the strains with the disease or health. The sampling technique and disease associations in the foregoing study did not depend on sampling locations, on the presence of lesions in the sampling field, or on inherently biased culture techniques. While sampling lesional skin intentionally may yield interesting results, these results would not be capable of defining the disease associations that unbiased sampling can. The metagenomic approach employed in the foregoing study to identify underlying strain differences in acne may also be applied to the study of other disease/health associations with commensal or pathogenic bacteria.

Materials and Methods

Subjects

Figure 3:
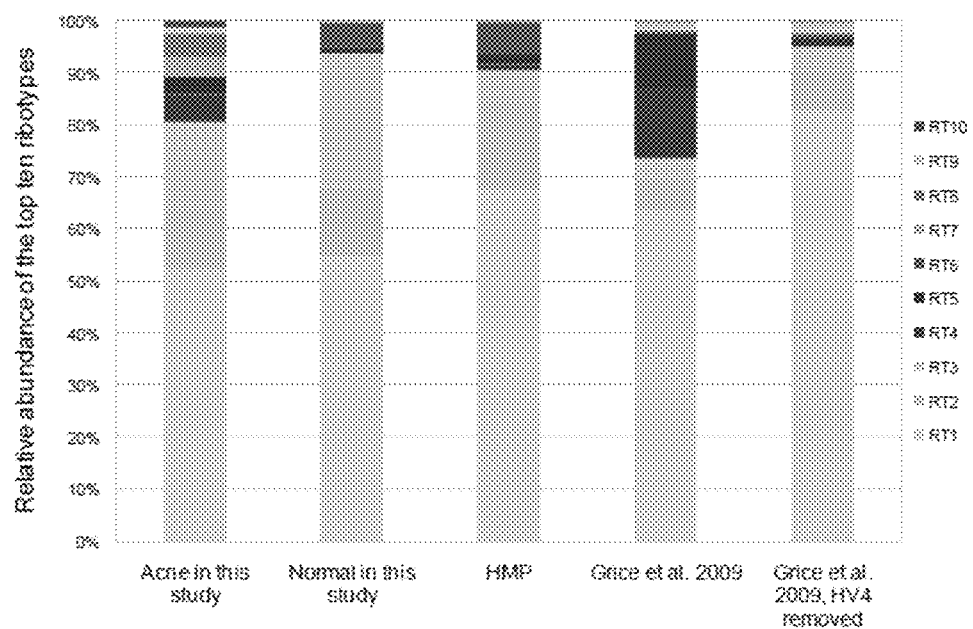
FIG. 3 shows that the most abundant *P. acnes* ribotypes in pilosebaceous units were also abundant at other body sites. The major ribotypes found in acne patients and normal individuals were compared to the datasets from the HMP and Grice et al. (2009). The top three ribotypes are the most abundant ones in different datasets. The excess RT4 and RT5 seen in the dataset by Grice et al. (2009) was due to one subject, HV4, whose *P. acnes* strain population was dominated by these two ribotypes at every skin site sampled. After removal of this subject, the ribotype distribution is similar to the HMP samples and the normal skin samples studied. RT6 is also found abundant in the HMP dataset, which were collected from healthy individuals.

Subjects with acne and subjects with normal skin were recruited from various clinics in Southern California including private practice, managed care, and public hospital settings, as well as outside of dermatology clinics, to best represent the diversity of populations and history of medical care. The subject data are available at dbGaP (found on the World Wide Web at ncbi.nlm.nih.gov/projects/gap/cgi-bin/study.cgi?study_id=phs000263.v1.p1). The diagnosis of acne was made by board-certified dermatologists. The presence of acne was graded on a scale of 0 to 5 relating closely to the Global Acne Severity Scale (Dreno et al., 2011). Grades were recorded for both the face and the nose separately where zero represents normal skin and 5 represents the most severe inflammatory cystic acne. In acne patients, the grades of the face ranged from 1 to 5 with an average of 2.1, and the grades of the nose ranged from 0 to 2 with an average of 0.3. The presence of scarring was also noted. Subjects with normal skin were determined by board-certified dermatologists and were defined as people who had no acneiform lesions on the face, chest, or back. They were also excluded if they had other skin problems that the investigators felt would affect sampling or the microbial population on the skin. Among the 101 subjects, 59 were female (31 acne patients and 28 normal subjects) and 42 were male (18 acne patients and 24 normal subjects). The average age of the acne cohort was 22.2 and the average age of the normal cohort was 29.6. There was no significant difference in ethnicity between the acne and normal populations. The subjects responded to a written questionnaire, administered by a physician or a well-trained study coordinator who went over each question with the subjects. Most of the subjects had not been treated for acne in the past or were not being treated when samples were collected (FIG. 3). Only nine out of 78 subjects, who provided treatment information, were being treated for acne when samples were taken. Among the nine subjects, two were being treated with antibiotics, five were being treated with topical retinoids, one was being treated with both antibiotics and retinoids, and one did not list the treatment. Subjects were asked for acne treatment history in the past (anytime in their life). Eighteen out of 73 subjects, who provided treatment history, had been treated for acne in the past. Among them, seven had been treated with antibiotics, eight had been treated with retinoids, two had been treated with both antibiotics and retinoids, and one did not list the treatment. All subjects provided written informed consent. All protocols and consent forms were approved by both the UCLA and Los Angeles Biomedical Research Institute IRBs. The study was conducted in adherence to the Helsinki Guidelines.

Samples

Skin microcomedone (white head or black head) samples were taken from the nose of the subjects using Bioré Deep Cleansing Pore Strips (Kao Brands Company, Cincinnati, Ohio) following the instruction of the manufacturer. Clean gloves were used for each sampling. After being removed from the nose, the strip was immediately placed into a 50 mL sterile tube and kept on ice or at 4° C. The cells were lysed within four hours in most of the cases.

Metagenomic DNA Extraction, 16S rDNA Amplification, Cloning, and Sequencing

Individual microcomedones were isolated from the adhesive nose strip using sterile forceps. Genomic DNA was extracted using QIAamp DNA Micro Kit (Qiagen, Valencia, Calif.). 16S rDNA was amplified and cloned according to the protocol by HMP, which is described in detail in Supplementary Information. Nearly full length sequences were obtained by Sanger method.

16S rDNA Sequence Analysis

Base calling and quality was determined with Phred (Ewing and Green, 1998; Ewing et al., 1998). Bidirectional reads were assembled and aligned to a core set of NAST-formatted sequences (rRNA16S.gold) using AmosCmp16Spipeline and NAST-ier (Haas et al., 2011). Suspected chimeras were identified using ChimeraSlayer and WigeoN (Haas et al., 2011). 16S rDNA sequences were extensively manually examined. Chromatograms were visually inspected at all bases with a Phred quality score <30. Appropriate corrections were applied. QIIME (Caporaso et al., 2010) was used to cluster the sequences into OTUs.

*P. acnes* Isolation and Genotyping

Colonies with the macroscopic characteristics of *P. acnes* were picked from each sample plate and were passed twice. The ribotype of each isolate was determined by PCR amplification and sequencing of the full length of the 16S rDNA gene by Sanger method.

Whole Genome Shotgun Sequencing, Assembly, and Annotation

Genome HL096PA1 was sequenced using Roche/454 FLX and was assembled using a combination of PHRAP/CONSED (Gordon et al., 1998) and GSMAPPER (Roche, Branford, Conn.) with extensive manual editing in CONSED. The remaining 65 genomes were sequenced using Illumina/Solexa GAIIx (Illumina, San Diego, Calif.). Sequence datasets were processed by quality trimming and were assembled using Velvet (Zerbino and Birney, 2008). Coding sequences were predicted using GeneMark (Borodovsky and Mclninch, 1993) and GLIMMER (Salzberg et al., 1998). The final gene set was processed through a suite of protein categorization tools consisting of Interpro, psort-b and KEGG. A more detailed protocol can be found at hmpdacc.org/doc/sops/reference_genomes/annotation/WUGC_SOP_DACC.pdf. Comparative Genome Analysis Seventy-one P. acnes genome sequences were compared using Nucmer (Kurtz et al., 2004). Phylogenetic analysis was performed using MEGA5 (Tamura et al., 2007). CRISPRFinder (Grissa et al., 2007) was used to identify the CRISPR repeat-spacer sequences.

Supplementary Information
16S rDNA Sequence of KPA171202

All sequenced P. acnes genomes encode three copies of 16S rRNA genes, which are identical within each isolate, except KPA171202. Based on the KPA171202 genome (Bruggemann et al., 2004), one copy of the 16S rRNA gene has one nucleotide difference from the other two identical copies of RT1. However, this mutation was never observed in the 16S rDNA dataset. Multiple clones of 16S rDNA gene from KPA171202 were amplified, cloned, and sequenced and a sequence harboring this mutation was not found. Thus, KPA171202 also has three identical copies of 16S rDNA.

Comparison of P. acnes Strain Distribution to Other Human Microbiome Datasets

Figure 7:
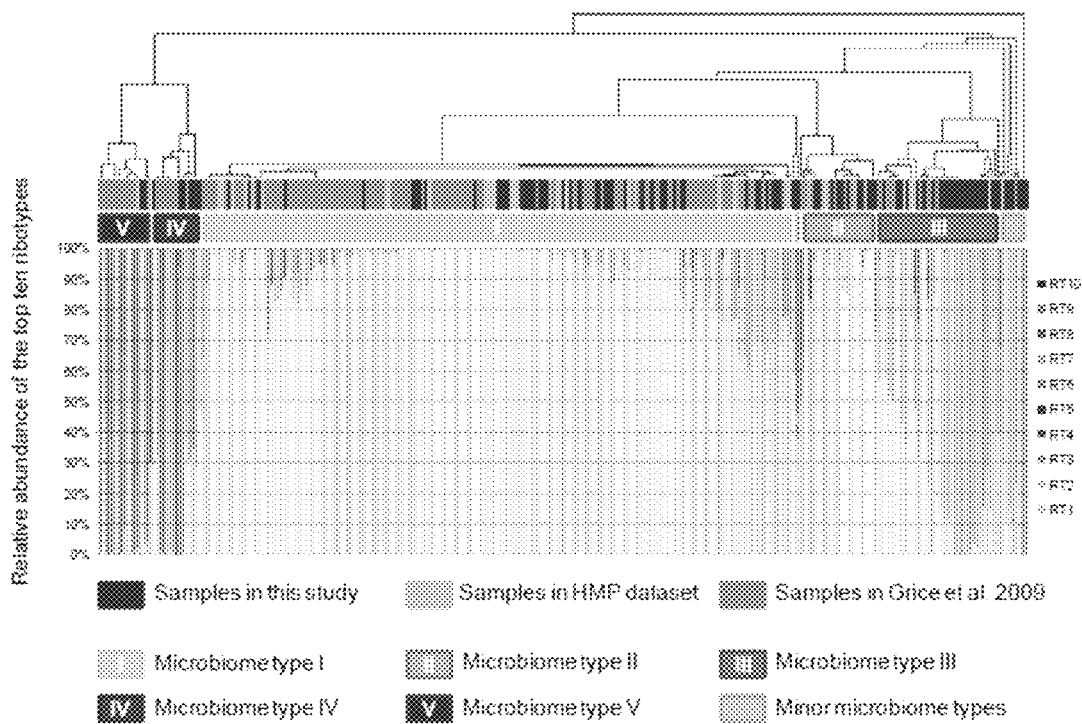
FIG. 7 shows that the same five major microbiome types were observed in multiple datasets. Samples from the study, HMP, and Grice et al. (2009) were clustered together based on the top ten most abundant *P. acnes* ribotypes. In total, 284 samples were included. Each column represents the percentage of the top ten ribotypes identified in each sample. Both HMP samples and samples from Grice et al. (2009) were collected from healthy individuals, therefore the percentage of microbiome types IV and V are under-represented in the analysis. Samples with fewer than ten sequences of the top ten ribotypes were not included.

To determine whether the P. acnes ribotypes and their relative abundances measured in this study are unique to pilosebaceous units, a similar analysis to the microbiome 16S rDNA data from the Human Microbiome Project (HMP) and the data from Grice et al. (2009) were applied. Both datasets were obtained from healthy subjects. The relative abundance of the major ribotypes in healthy subjects from the study was largely similar to that found in these two datasets despite the fact that they were sampled from different anatomical sites (FIG. 3). RT6 (6.3%) was found to be more abundant than RT4 and RT5 combined (2.8%) in the HMP data, similar to those found in the normal cohort where RT6 represents 4.8% and RT4 and RT5 combined represent 1.2% of the clones. The same five main microbiome types were observed in the two datasets (FIG. 7).

Genome Clustering and Phylogenetic Tree

The recA gene has been widely used to classify P. acnes strains into four known types: IA, IB, II, and III (McDowell et al., 2008; McDowell et al., 2005). The phylogenetic tree of the 71 genomes based on the SNPs in the core genome matched the recA types perfectly except one isolate, HL097PA1. Most of the genomes with ribotypes 1, 4, 5, and 532 were grouped to recA Type IA clade, which can be further divided into subclades IA-1 and IA-2. Clade IA-2 is composed of mostly RT4 and RT5. RT4 and most of RT5 genomes seem to belong to the same lineage with very similar genome sequences. All the isolates with ribotypes 3, 8, and 16, who share the mutation of T1007C in the 16S rDNA gene, were grouped to recA Type IB clade. Most of the RT3 genomes form a subclade IB-2 and RT8 genomes form a subclade by themselves, IB-1, which was highly associated with acne. Notably, RT2 and RT6, who share T854C mutation, have a more distant phylogenetic relationship to other ribotypes, and were grouped to the recA Type II clade. This is consistent with previous studies (Lomholt and Kilian, 2010; McDowell et al., 2005). P. acnes isolates with recA type III were not found in the samples.

The associations of P. acnes lineages with health and disease states were further analyzed. There was a clear shift of the association strength of the clades with acne along the phylogenetic tree (FIG. 9). The three sequenced ribotypes identified as being strongly associated with acne (RT4, RT5, and RT8) were found at one end of the tree in clades IA-2 and IB-1, while the RT6 identified as being associated with normal skin was at the other end of the tree at the tip of clade II (FIG. 9).

Antibiotic Resistance

P. acnes ribotypes 4, 5, and 10 have a single nucleotide substitution G1058C in the 16S rDNA sequences, which has previously been shown to confer increased resistance to tetracycline (Ross et al., 1998a; Ross et al., 2001). In addition to the substitution in the 16S rDNA sequences, it was determined that all the strains of RT4 and RT5 that were sequenced have a nucleotide substitution in the 23S rDNA sequences, which confers increased resistance to a different class of antibiotics, erythromycin and clindamycin (Ross et al., 1997; Ross et al., 1998b). It was experimentally confirmed that these isolates, except two that were unculturable, were resistant to tetracycline, erythromycin, and clindamycin.

It was also examined whether the enrichment of these ribotypes in the acne group could be due to antibiotic treatment. However, in the study only a small percentage of the subjects harboring ribotypes 4, 5, or 10 were treated with antibiotics (Table 4).

TABLE 4

Past and current treatments of the subjects

| | Group | | | |
|---|---|---|---|---|
| | Acne | | Normal | |
| | Number of subjects | | | |
| | 49 | | 52 | |
| | with RT4, RT5, or RT10 | without RT4, RT5, and RT10 | with RT4, RT5, or RT10 | without RT4, RT5, and RT10 |
| Number of subjects in each subgroup | 20 | 29 | 9 | 43 |
| Subjects reported on current treatment | 14 | 25 | 8 | 31 |
| no treatment | 10 | 21 | 8 | 30 |
| antibiotics | 0 | 2 | 0 | 0 |
| retinoids | 3 | 2 | 0 | 0 |
| antibiotics and retinoids | 0 | 0 | 0 | 1 |
| unknown | 1 | 0 | 0 | 0 |
| Subjects reported on past treatment | 12 | 22 | 8 | 31 |
| no treatment | 5 | 16 | 6 | 28 |
| antibiotics | 2 | 4 | 0 | 1 |
| retinoids | 4 | 1 | 1 | 2 |
| antibiotics and retinoids | 1 | 0 | 1 | 0 |
| unknown | 0 | 1 | 0 | 0 |

Eighteen of the 29 subjects who harbored any of these three ribotypes gave reports on both past and current treatments. Among them, 50% (9/18) of the subjects were never treated; 33% (6/18) were treated with retinoids; 11% (2/18)

were treated with antibiotics in the past, and 5.6% (1/18) were treated with both antibiotics and retinoids in the past. The theory of selection by antibiotic treatment is not favored by this study. Previous surveys of antibiotic resistant strains in acne patients demonstrated that previous use of antibiotics did not always result in the presence of resistant strains and that some patients without previous use of antibiotics harbored resistant strains (Coates et al., 2002; Dreno et al., 2001). Observations in this study are consistent with previous studies.

CRISPR Spacer Sequences

Although more similar to the GC content of *P. acnes* genomes, four unique spacer sequences found in strains of RT2 and RT6 have the best matches to the genome of *Clostridium leptum*, a commensal bacterium in the gut microbiota (Table 3). On the 55Kb plasmid harbored in HL096PA1 and other RT4 and RT5 genomes, there is also a large cluster of 35 genes that are identical to the genes found in *C. leptum*, including the Tad locus.

Materials and Methods

Metagenomic DNA Extraction, PCR Amplification, Cloning and 16S rDNA Sequencing

Metagenomic DNA extraction

Individual microcomedones were isolated from the adhesive nose strip using sterile forceps and placed in a 2 mL sterile microcentrifuge tube filled with ATL buffer (Qiagen) and 0.1 mm diameter glass beads (BioSpec Products, Inc., Bartlesville, Okla.). Cells were lysed using a beadbeater for 3 minutes at 4,800 rpm at room temperature. After centrifugation at 14,000 rpm for 5 minutes, the supernatant was retrieved and used for genomic DNA extraction using QIAamp DNA Micro Kit (Qiagen). The manufacturer protocol for extracting DNA from chewing gum was used. Concentration of the genomic DNA was determined by NanoDrop 1000 Spectrophotometer.

16S rDNA PCR Amplification, Cloning and Sequencing

Most of the metagenomic samples were amplified in triplicate using 16S rDNA specific primers with the following sequences: 27f-MP 5'-AGRGTTTGATCMTGGCTCAG-3' and 1492r-MP 5'-TACGGYTACCTTGTTAYGACTT-3'. PCR reactions contained 0.5 U/µL Platinum Taq DNA Polymerase High Fidelity (Invitrogen), 1× Pre-mix E PCR buffer from Epicentre Fail-Safe PCR system, 0.12 µM concentration of each primer 27f-MP and 1492r-MP, and Sigma PCR grade water. One microliter of DNA (ranging from 0.2-10 ng total) was added to each reaction. The G-Storm GS4 thermocycler conditions were as following: initial denaturation of 96° C. for 5 minutes, and 30 cycles of denaturation at 94° C. for 30 seconds, annealing at 57° C. for 1 minute, and extension at 72° C. for 2 minutes, with a final extension at 72° C. for 7 minutes. Following amplification, an A-tailing reaction was performed by the addition of 1 U of GOTaq® DNA Polymerase directly to the amplification reaction and incubation in the thermocycler at 72° C. for 10 minutes.

The three PCR amplification reactions from each source DNA were pooled and gel purified (1.2% agarose gel stained with SYBR Green fluorescent dye). The 1.4 Kb product was excised and further purified using the Qiagen QIAquick Gel Extraction Kit®. The purified product was cloned into OneShot® *E. coli* cells using TOPO TA® cloning kit from Invitrogen.

White colonies were picked into a 384-well tray containing terrific broth, glycerol, and kanamycin using a Qpix picking robot. Each tray was prepared for sequencing using a magnetic bead prep from Agilent and sequenced with 1/16th Big Dye Terminator from ABI. Sequencing was done with a universal forward, universal reverse, and for a subset, internal 16S rDNA primer 907R with sequences of TGTAAAACGACGGCCAGT (forward), CAG-GAAACAGCTATGACC (reverse), and CCGTCAAT-TCCTTTRAGTTT (907R). Sequence reactions were loaded on ABI 3730 machines from ABI on 50 cm arrays with a long read run module.

A slightly different PCR and cloning protocol without automation was used for several initial samples as described below. 16S rDNA was amplified using universal primers 8F (5'-AGAGTTTGATYMTGGCTCAG-3') and 1510R (5'-TACGGYTACCTTGTTACGACTT-3') (Gao et al., 2007). Thermocycling conditions were as following: initial denaturation step of 5 minutes at 94° C., 30 cycles of denaturation at 94° C. for 45 seconds, annealing at 52° C. for 30 seconds and elongation at 72° C. for 90 seconds, and a final elongation step at 72° C. for 20 minutes.

PCR products were purified using DNA Clean and Concentrator Kit (Zymo Research). Subsequently, the 16S rDNA amplicons were cloned into pCR 2.1-TOPO vector (Invitrogen). One-Shot TOP-10 Chemically Competent *E. coli* cells (Invitrogen) were transformed with the vectors and plated on selective media. Individual positive colonies were picked and inoculated into selective LB liquid medium. After 14 hours of incubation, the plasmids were extracted and purified using PrepEase® MiniSpin Plasmid Kit (USB Corporation) or Zyppy® Plasmid Miniprep Kit (Zymo Research). The clones were sequenced bidirectionally using Sanger sequencing method with 1/8th chemistry using ABI 3730 sequencer (Applied Biosystems Inc.).

*P. acnes* Isolation and Culturing

Sample Culture Plate

Microcomedones on the inner surface of the nose strip were mashed and scraped using a sterile loop (Fisherbrand, Pittsburgh, Pa.), and plated onto a blood agar plate (Teknova Brucella Agar Plate with Hemin and Vitamin K, Teknova, Hollister, Calif.). The plates were incubated at 37° C. for 5-7 days anaerobically using the AnaeroPack System (Mitsubishi Gas Chemical Company, Tokyo, Japan).

Isolation and Culturing of Individual Strains

Colonies with the macroscopic characteristics of *P. acnes* were picked from each sample plate and were streaked onto A-media plates (Pancreatic Digase of Casine, Difco yeast extract, glucose, KH2PO4, MgSO4, Difco Agar, and water). These first-pass plates were then incubated anaerobically at 37° C. for 5-7 days. As the second pass, single isolated colonies were picked from the first-pass plates and streaked onto new A-Media plates. These plates were then incubated anaerobically at 37° C. for 5-7 days. The colonies on these plates were picked for culturing, genotyping, and genome sequencing in the subsequence steps.

Genotyping of the *P. acnes* Isolates

Each isolate was analyzed by PCR amplification of the 16S rDNA gene. The ribotypes were determined based on the full length sequences. Isolates with desired ribotypes were selected for future culturing and genome sequencing.

Genomic DNA Extraction of *P. acnes* Isolates

Isolates were grown in 5 mL of Clostridial medium under anaerobic conditions at 37° C. for 5-7 days. Cultures were pelleted by centrifugation and washed with 3 mL phosphate buffer saline (PBS). The same protocol used for the metagenomic DNA extraction was used for extracting the genomic DNA of the isolates.

Metagenomic Shotgun Sequencing and Analysis

Metagenomic DNA samples from microcomedone samples from 22 individuals with normal skin were pooled and sequenced using Roche/454 FLX. The average read length was 236 bp. The sequencing was limited with 13,291 sequence reads. Sequence reads were aligned against the NCBI's non-redundant database using BLAST. Species assignment was based on 97% identity and 100% of the read length aligned.

Assembly, Alignment and Editing of 16S rDNA Sequences
Assembly and Alignment

Base calling and quality were determined with Phred (Ewing and Green, 1998; Ewing et al., 1998) using default parameters. Bidirectional reads were assembled and aligned to a core set of NAST-formatted sequences (rRNA16S.gold) using AmosCmp16Spipeline and NAST-ier, which are from the Microbiome Utilities Portal of the Broad Institute (microbiomeutil.sourceforge.net/). These tools in turn use Amoscmp (Pop et al., 2004), Mummer (Kurtz et al., 2004), Lucy (Chou and Holmes, 2001), BLAST (Altschul et al., 1990) and CdbTools (compbio.dfci.harvard.edu/tgi/software/). Suspected chimeras were identified using ChimeraSlayer and WigeoN (Haas et al., 2011). Sequences with at least 90% bootstrap support for a chimeric breakpoint (ChimeraSlayer) or containing a region that varies at more than the 99% quantile of expected variation (WigeoN) were removed from further analysis.

Quality Screening

For diversity analysis of the *P. acnes* population, sequences with at least 99% identity over 1,400 nucleotides to *P. acnes* KPA171202 (Bruggemann et al., 2004) 16S rDNA were trimmed to positions 29-1483 (numbering based on the *E. coli* system of nomenclature (Brosius et al., 1978)). Sequences without full coverage over this region were excluded from further strain level analysis. Chimera screening, as described above, resulted in removal of less than 0.35% of the sequences. This may be an under-estimation of the chimeras, since the majority of sequences differ by only 1 or 2 nucleotides. Low quality sequences were excluded, defined as more than 50 nucleotides between positions 79 and 1433 with Phred quality scores of less than 15. To allow detailed strain-level analysis, the data were extensively manually edited. Chromatograms were visually inspected at all bases with a Phred quality score <30, and appropriate corrections were applied. For analysis at the species level, the 16S rDNA sequences were not manually edited. Chimera screening of assembled sequences resulted in removal of less than 0.65% of the sequences. Aligned sequences were trimmed to *E. coli* equivalent positions 29-1483 (Brosius et al., 1978). Sequences without full coverage over this region were excluded from further analysis.

Sequence Editing

Nearly 62,000 Sanger sequence reads representing the 26,446 assembled *P. acnes* sequences were mapped to the RT1 sequence in CONSED (Gordon, 2003; Gordon et al., 1998). Comprehensive semi-manual editing of the large number of sequences was made feasible by their very high pairwise similarities: a median of only one nucleotide change from RT1 per sequence (three nucleotide changes prior to editing). Editing was facilitated by the use of scripts and the custom navigation feature of CONSED allowing single click jumps to sites requiring inspection. Chromatograms were inspected for all low quality (Phred <30) bases that differed from RT1, and corrected as needed, including many commonly occurring sequence errors. In order to minimize the effect of base mis-incorporation and chimera, specific base differences from RT1 occurring in less than 4 sequences (frequency <0.00015) were considered unreliable and reverted to the corresponding RT1 base. Ribotypes were assigned for the resulting sequences based on 100% identity.

16S rDNA Sequence Analysis
OTUs and Taxonomy Assignments

QIIME (Caporaso et al., 2010b) was used to cluster the sequences into OTUs using 99% identity cutoff, furthest neighbor, and UCLUST (Edgar, 2010). Representative sequences (most abundant) were selected and aligned using PYNAST (Caporaso et al., 2010a) to the greengenes database. Taxonomy was assigned using RDP method (Cole et al., 2009). The alignment was filtered with the lanemask provided by greengenes, and a phylogenetic tree was built using FastTree (Price et al., 2009).

Wilcoxon Test on the Top Ten Ribotypes

For each sample, the number of clones of each of the top ten ribotypes was normalized by the total number of *P. acnes* clones of the sample. The normalized counts were used to test the significance in enrichment between the acne group and the normal group. The function wilcox_test in the R program (found on the World Wide Web at R-project.org) was used to calculate the p-values.

Microbiome Type Assignments

Microbiome types were assigned based on the largest clades seen when samples were clustered using thetayc similarity in MOTHUR (Schloss et al., 2009) (FIGS. 5 and 6) or hierarchical clustering (Eisen et al., 1998) (FIG. 7).

Assigning Ribotypes to Datasets of HMP and Grice et al. 2009

Sequences were assigned to a ribotype if they met the following criteria. First, there was a single best match. Second, it covered the range required to discriminate between the top 45 ribotypes (58-1388). Third, there were no Ns at discriminatory positions. Lastly, there were no more than ten non-discriminatory differences.

The HMP 16S rDNA Sanger sequence dataset was downloaded with permission from the HMP Data Analysis and Coordination Center. It has 8,492 *P. acnes* sequences from 14 subjects and nine body sites (retroauricular crease, anterior nares, hard palate, buccal mucosa, throat, palatine tonsils, antecubital fossa, saliva, and subgingival plaque). More details on the dataset can be found on the World Wide Web at ncbi.nlm.nih.gov/projects/gap/cgi-bin/study.cgi?study_id=phs000228.v2.p1. In this dataset, low quality bases (Phred quality <20) were converted to Ns, and 26% of the sequences were not assigned due to excessive Ns or Ns at ribotype discriminatory sites. Less than 1% was unresolved due to equal best matches or greater than ten mismatches to RT1.

The dataset from Grice et al. (2009) is available at NCBI (GenBank accession numbers GQ000001 to GQ116391). It has 22,378 *P. acnes* sequences from ten subjects and 21 skin sites (buttock, elbow, hypothenar palm, volar forearm, antecubital fossa, axillary vault, gluteal crease, inguinal crease, interdigital web space, nare, plantar heel, popliteal fossa, toe web space, umbilicus, alar crease, back, external auditory canal, *glabella*, manubrium, occiput, and retroauricular crease). Three percent of the sequences were unassigned due to greater than ten mismatches to RT1, and 1.6% was unassigned due to equal best matches.

For comparison purpose, the unedited 16S rDNA sequences were assigned to ribotypes by the same method described above and the result is shown in FIG. 3. Less than 0.6% of the sequences were unassigned due to greater than ten mismatches to RT1, and 1.7% was unassigned due to equal best matches.

Whole Genome Shotgun Sequencing, Assembly and Annotation of 66 *P. acnes* Isolates
Genome HL096PA1

The genome was sequenced using Roche/454 FLX at the UCLA Genotyping and Sequencing Core. A total of 590,054 sequence reads were generated with an average read length of 230 bp. Of these, 433,896 were assembled into two contigs, a circular main chromosome of 2,494,190 bp and a linear plasmid of 55,585 bp. Assembly was accomplished by a combination of PHRAP/CONSED (Gordon et al., 1998) and GSMAPPER (Roche) with extensive manual editing in CONSED. GeneMark v2.6r (Borodovsky and Mclninch, 1993) and GLIMMER v2.0 (Salzberg et al., 1998) were used to performed ab initio protein coding gene prediction. tRNAScan-SE 1.23 was used for tRNA identification and RNAmmer was used for predicting ribosomal RNA genes (5S, 16S, and 23S). Genome annotation results were based on automated searches in public databases, including Pfam (pfam.jouy.inra.fr/), KEGG (found on the World Wide Web at genome.jp/kegg), and COG (found on the World Wide Web at ncbi.nlm.nih.gov/COG/). Manual inspection of the annotation was also performed.

Genomes of the Other 65 Isolates

The genomes were sequenced using Illumina/Solexa Genome Analyzer IIx and annotated by the Genome Center of Washington University at St. Louis.

Assembly

Each genomic DNA sample was randomly sheared and an indexed library was constructed using standard Illumina protocols. Twelve uniquely tagged libraries were pooled and run on one lane of a GAIIx flowcell and paired end sequences were generated. Following deconvolution of the tagged reads into the separate samples, datasets were processed using BWA (Li and Durbin, 2009) quality trimming at a q10 threshold. Reads trimmed to less than 35 bp in length were discarded and the remaining reads were assembled using oneButtonVelvet, an optimizer program that runs the Velvet assembler (Zerbino and Birney, 2008) numerous times over a user supplied k-mer range while varying several of the assembler parameters and optimizing for the assembly parameter set which yields the longest N50 contig length.

Annotation

Coding sequences were predicted using GeneMark v3.3 (Borodovsky and Mclninch, 1993) and GLIMMER v2.13 (Salzberg et al., 1998). Intergenic regions not spanned by GeneMark and GLIMMER were aligned using BLAST against NCBI's non-redundant database and predictions were generated based on protein alignments. tRNA genes were determined using tRNAscan-SE 1.23 and non-coding RNA genes were determined by RNAmmer-1.2 and Rfam v8.0. The final gene set was processed through a suite of protein categorization tools consisting of Interpro, psort-b and KEGG. The gene product naming comes from the BER pipeline (JCVI). A more detailed standard operating protocol (SOP) can be found at hmpdacc.org/doc/sops/reference_genomes/annotation/WUGC_SOP_DACC.pdf.

71 P. acnes Genome Analysis and Comparison

Identification of the Core Regions of P. acnes Genomes

The "core" regions were defined as genome sequences that are present in all 71 genomes. P. acnes KPA171202 was used as the reference genome. Each of the other 70 genome sequences (a series of contigs in most of the genomes and two complete genomes) was mapped to the reference genome using Nucmer (Kurtz et al., 2004). All the 70 ".coords" output files of Nucmer program were analyzed to identify overlap regions based on the KPA171202 coordinates using a Perl script. Finally, "core" sequences were extracted based on the genome sequence of KPA171202 with the coordinates calculated above. On average, 90% (ranging from 88% to 92%) of the genomes were included in the core regions.

Identification of SNPs in the Core Regions

Single nucleotide polymorphisms (SNPs) were identified by using "show-snps" utility option of the Nucmer program (Kurtz et al., 2004) with the default settings. Genome sequence of P. acnes KPA171202 was used as the reference genome. All the 70 ".snps" output files of Nucmer program were analyzed to identify unique SNP positions based on the KPA171202 coordinates using a Perl script. The SNPs in the core regions were further analyzed to construct a phylogenetic tree.

Phylogenetic Tree Construction

The 71 concatenated sequences of the 96,887 SNP nucleotides in the core regions were used to construct a phylogenetic tree of the P. acnes genomes. The evolutionary distance of the core regions among the genomes was inferred using the Neighbor-Joining method (Saitou and Nei, 1987). The bootstrap tree inferred from 1,000 replicates was taken. Branches corresponding to partitions reproduced in less than 80% bootstrap replicates were collapsed. FIG. 8 shows only the topology. In FIG. 9, the tree was drawn to scale, with branch lengths in the same units as those of the evolutionary distances used to infer the phylogenetic tree. The evolutionary distances were computed using the p-distance method and are in the units of the number of nucleotide differences per site. This tree shows the comparison based on only the core regions. The distance does not represent the true evolutionary distance between different genomes, since the non-core regions of each genome were not considered here. All positions containing gaps and missing data were eliminated. Evolutionary analysis was conducted using MEGA5 (Tamura et al., 2007).

Gene Content Comparison

In order to assess the conservation of gene content across the 71 genomes, protein coding genes in all the genomes were clustered using UCLUST (Edgar, 2010) by first sorting by decreasing length then clustering each sequence to an existing seed sequence if it had at least 90% nucleotide identity over its entire length, otherwise it became a new seed. For visualization, the data were reformatted to columns and rows representing genes and genomes, respectively. One or more copies of the genes in a genome were treated as present. Gene columns were sorted by their position based on the coordinates of the HL096PA1 genome, a fully finished genome with a 55Kb plasmid. Genome rows were sorted by their positions in the SNP-based Neighbor Joining tree described above.

Identification of CRISPR/Cas

CRISPRFinder (Grissa et al., 2007) was used to identify the CRISPR repeat-spacer sequences. The annotation of HL110PA3 was used for BLAST alignment in order to identify the presence of CRISPR/Cas structure and CRISPR repeat-spacer sequences in strains of HL001PA1, HL060PA1, HL082PA2, HL103PA1, HL106PA1, HL110PA4 and J139. Each spacer sequence was annotated by BLAST alignment against NCBI's non-redundant nucleotide database and the reference genomic sequences database (refseq_genomic).

Sequence Coverage Analysis

MAQ (Li et al., 2008) was used to map the raw sequence reads from Illumina/Roche platform to the reference genomes. Briefly, "map" command was used for mapping, and "assemble" command was used for calling the consensus sequences from read mapping, then "cnd2win" command was used to extract information averaged in a tilling window. A window size of 1,000 bp was used. Randomly selected 1 million reads were used for mapping. This accounted for approximately 40× coverage for all the genomes except HL096PA2, HL096PA3, HL097PA1 and HL099PA1, which had approximately 55× to 75× coverage. BWA (Li and Durbin, 2010) was used to map the raw sequence reads from Roche/454 platform to the reference genome HL096PA1. The average coverage was calculated in 1,000 bp window.

Quantitative PCR

Quantitative PCR (qPCR) targeting TadA on the plasmid (Locus 3) and housekeeping genes Pak and RecA on the chromosome was performed using the genomic DNA extracted from the *P. acnes* isolates. LightCyler 480 High Resolution Melting Master kit was used (Roche Diagnostics GmbH, Mannheim, Germany). Each 10 µl reaction solution was consisted of 5 µL master mix (2× concentrate), 1 µL 25 mM MgCl2, 0.5 µL 4 µM forward and reverse primers, and DNA template. Four qPCR runs were performed on Roche LightCycler 480. Primer sequences for TadA are 5'-GATAATCCGTTCGACAAGCTG-3' (forward) and 5'-ACC-CACCACGATGATGTTT-3' (reverse). Primer sequences for pak are 5'-CGACGCCTCCAATAACTTCC-3' (forward) and 5'-GTCGGCCTCCTCAGCATC-3' (reverse). Primer sequences for recA are 5'-CCGGAGACAACGACAGGT-3' (forward) and 5'-GCTTCCTCATACCACTGGTCATC-3' (reverse). All samples were run in duplicates in each qPCR run, except the second run, which was not duplicated. Thermocycling conditions were as following: initial activation step of 10 minutes at 95° C.; 50 amplification cycles with each consisting of 10 seconds at 95° C., 15 seconds at 65° C. in the first cycle with a stepwise 0.5° C. decrease for each succeeding cycle, and 30 seconds at 72° C.; and final melting curve step starting at 65° C. and ending at 99° C. with a ramp rate of 0.02° C./s and acquisition rate of 25/° C.. DNA concentration standards were run in duplicates. Copy number ratios of genes were calculated based on the concentrations of the genes on the plasmid and chromosome.

Data Availability 16S rDNA sequences have been deposited at GenBank under the project ID 46327. Whole genome shotgun sequences and annotations of the *P. acnes* strains have been deposited at GenBank under the accession numbers ADWB00000000, ADWC00000000, ADWF00000000, ADWH00000000, ADWI00000000, ADXP00000000, ADXQ00000000, ADXR00000000, ADXS00000000, ADXT00000000, ADXU00000000, ADXW00000000, ADXX00000000, ADXY00000000, ADXZ00000000, ADYA00000000, ADYB00000000, ADYC00000000, ADYD00000000, ADYE00000000, ADYF00000000, ADYG00000000, ADYI00000000, ADYJ00000000, ADYK00000000, ADYL00000000, ADYM00000000, ADYN00000000, ADYO00000000, ADYP00000000, ADYQ00000000, ADYR00000000, ADYS00000000, ADYT00000000, ADY000000000, ADYV00000000, ADYW00000000, ADYX00000000, ADYY00000000, ADYZ00000000, ADZA00000000, ADZB00000000, ADZC00000000, ADZD00000000, ADZE00000000, ADZF00000000, ADZG00000000, ADZH00000000, ADZI00000000, ADZJ00000000, ADZK00000000, ADZL00000000, ADZM00000000, ADZN00000000, ADZO00000000, ADZP00000000, ADZQ00000000, ADZR00000000, ADZS00000000, ADZT00000000, ADZV00000000, ADZW00000000, CP003293, and CP003294.

Example 2—Pan-Genome and Comparative Genome Analysis of *Propionibacterium Acnes*

*Propionibacterium acnes* is a major human skin bacterium. To understand whether different strains have different virulent properties and thus play different roles in health and diseases, the genomes of 82 *P. acnes* strains, most of which were isolated from acne or healthy skin, were compared. Lineage-specific genetic elements were identified that may explain the phenotypic and functional differences of *P. acnes* as a commensal in health and as a pathogen in diseases. By analyzing a large number of sequenced strains, an improved understanding of the genetic landscape and diversity of the organism at the strain level and at the molecular level is provided.

Introduction

*Propionibacterium acnes* is a major commensal of the human skin. It contributes to maintaining the skin health by inhibiting the invasion of common pathogens, such as *Staphylococcus aureus* and *Streptococcus pyogenes*. It does so by hydrolyzing triglycerides and releasing free fatty acid that contributes to the acidic pH of the skin surface (1). On the other hand, *P. acnes* has been historically linked to acne vulgaris, a chronic inflammatory disease of the pilosebaceous unit affecting more than 85% of adolescents and young adults (2). A metagenomic study previously demonstrated that *P. acnes* was a dominant bacterium in the pilosebaceous unit in both healthy individuals and acne patients (3, 4). At the strain level, however, the population structures of *P. acnes* were different between the two groups. These findings suggested that microbe-related human diseases are often caused by certain strains of a species rather than the entire species, in line with the studies of other diseases (5, 6).

*P. acnes* has been classified into three distinct types. Studies by Johnson and Cummins (7) first revealed two distinct phenotypes of *P. acnes*, known as types I and II, that could be distinguished based on serological agglutination tests and cell wall sugar analysis. McDowell et al. (8) differentiated types I and II *P. acnes* by monoclonal antibody typing. Furthermore, their phylogenetic analysis of *P. acnes* strains based on the nucleotide sequences of the recA gene and a more variable hemolysin/cytotoxin gene (tly) demonstrated that types I and II represent distinct lineages. Their investigations also revealed that strains within the type I lineage could be further split into two clades, known as types IA and IB (8, 9). An additional phylogenetic group of *P. acnes*, known as type III was described later (10). Recent studies based on multilocus sequence typing (MLST) further sub-divided *P. acnes* into closely related clusters, some of which were associated with various diseases including acne (11-13).

The first complete genome sequence of *P. acnes*, KPA171202, a type IB strain, provided insights on the pathogenic potential of this Gram-positive bacterium (14). The genome is 2.56 M bp with 60% of GC content. It encodes 2,333 open reading frames (ORFs) including multiple gene products involved in degrading host molecules, such as sialidases, neuraminidases, endoglycoceramidases, lipases, and pore-forming factors. However, the sequence of a single genome does not reflect the genetic landscape of the organism and how genetic variations among strains determine their various phenotypes and pathogenic properties.

To better understand the human microbiome variations at the strain level, as part of the Human Microbiome project (HMP) (15, 16), previously generated were the reference genome sequences of 66 *P. acnes* strains selected from a collection of over 1,000 strains isolated from a cohort of healthy subjects and acne patients (4). These 66 strains represent the major lineages of *P. acnes* found on the human skin, including types IA, IB, and II. To cover all the main *P. acnes* lineages in the analysis, three additional *P. acnes* strains were sequenced, including the first available type III *P. acnes* genome. Thirteen *P. acnes* genomes sequenced by other research groups (14, 17-22) were also available at the time of analysis. With a total of 82 genomes, performed was a comparative genome analysis to characterize the pan-genome of *P. acnes*, the phylogenetic relationships among different lineages, the microevolution of the strains in the same individual microbiome, and the genetic elements specific to each lineage and their associations with health and disease.

Results

*P. acnes* Strains and General Genome Features

To understand the genomic diversity of this important skin commensal at the strain level, the genomes of 69 sequenced *P. acnes* strains were analyzed. Among them, 67 *P. acnes* strains were isolated from the skin of healthy individuals and acne patients (3, 4), and two *P. acnes* strains, HL201 PA1 and HL202PA1, were isolated from refractory endodontic lesions (23) (Table 5).

TABLE 5

General features of the 82 *P. acnes* genomes

| Genome | Strain name | Origin | Ribotype | recA type | Sequencing method | Genome size (Mb) | GC % | Number of ORFs |
|---|---|---|---|---|---|---|---|---|
| 1 | HL001PA1 | Skin | 2 | II | Illumina | 2.49 | 60.0 | 2,661 |
| 2 | HL002PA1 | Skin | 3 | IB | Illumina | 2.48 | 60.1 | 2,549 |
| 3 | HL002PA2 | Skin | 1 | IA | Illumina | 2.48 | 60.1 | 2,594 |
| 4 | HL002PA3 | Skin | 1 | IA | Illumina | 2.48 | 60.1 | 2,565 |
| 5 | HL005PA1 | Skin | 4 | IA | Illumina | 2.53 | 60.2 | 2,724 |
| 6 | HL005PA2 | Skin | 1 | IA | Illumina | 2.48 | 60.0 | 2,645 |
| 7 | HL005PA3 | Skin | 1 | IA | Illumina | 2.48 | 60.1 | 2,579 |
| 8 | HL005PA4 | Skin | 3 | IB | Illumina | 2.47 | 60.0 | 2,607 |
| 9 | HL007PA1 | Skin | 4 | IA | Illumina | 2.53 | 60.2 | 2,691 |
| 10 | HL013PA1 | Skin | 3 | IB | Illumina | 2.48 | 60.0 | 2,618 |
| 11 | HL013PA2 | Skin | 1 | IA | Illumina | 2.48 | 60.1 | 2,588 |
| 12 | HL020PA1 | Skin | 1 | IA | Illumina | 2.48 | 60.1 | 2,554 |
| 13 | HL025PA1 | Skin | 1 | IB | Illumina | 2.54 | 60.1 | 2,581 |
| 14 | HL025PA2 | Skin | 3 | IB | Illumina | 2.48 | 60.0 | 2,616 |
| 15 | HL027PA1 | Skin | 3 | IB | Illumina | 2.53 | 60.1 | 2,711 |
| 16 | HL027PA2 | Skin | 1 | IA | Illumina | 2.48 | 60.1 | 2,629 |
| 17 | HL030PA1 | Skin | 1 | IB | Illumina | 2.54 | 60.0 | 2,662 |
| 18 | HL030PA2 | Skin | 3 | IB | Illumina | 2.51 | 60.1 | 2,647 |
| 19 | HL036PA1 | Skin | 532 | IA | Illumina | 2.48 | 60.1 | 2,575 |
| 20 | HL036PA2 | Skin | 532 | IA | Illumina | 2.48 | 60.1 | 2,565 |
| 21 | HL036PA3 | Skin | 1 | IA | Illumina | 2.48 | 60.1 | 2,601 |
| 22 | HL037PA1 | Skin | 3 | IB | Illumina | 2.48 | 60.1 | 2,617 |
| 23 | HL038PA1 | Skin | 4 | IA | Illumina | 2.54 | 60.2 | 2,663 |
| 24 | HL042PA3 | Skin | 6 | II | Roche/454 | 2.53 | 60.1 | 2,610 |
| 25 | HL043PA1 | Skin | 5 | IA | Illumina | 2.53 | 60.2 | 2,698 |
| 26 | HL043PA2 | Skin | 5 | IA | Illumina | 2.53 | 60.2 | 2,688 |
| 27 | HL045PA1 | Skin | 4 | IA | Illumina | 2.53 | 60.2 | 2,692 |
| 28 | HL046PA1 | Skin | 3 | IB | Illumina | 2.48 | 60.0 | 2,599 |
| 29 | HL046PA2 | Skin | 1 | IA | Illumina | 2.53 | 60.1 | 2,692 |
| 30 | HL050PA1 | Skin | 3 | IB | Illumina | 2.48 | 60.0 | 2,652 |
| 31 | HL050PA2 | Skin | 1 | II | Illumina | 2.46 | 60.1 | 2,581 |
| 32 | HL050PA3 | Skin | 3 | IB | Illumina | 2.48 | 60.0 | 2,558 |
| 33 | HL053PA1 | Skin | 4 | IA | Illumina | 2.53 | 60.2 | 2,632 |
| 34 | HL053PA2 | Skin | 8 | IB | Illumina | 2.51 | 60.1 | 2,664 |
| 35 | HL056PA1 | Skin | 4 | IA | Illumina | 2.48 | 60.1 | 2,581 |
| 36 | HL059PA1 | Skin | 16 | IB | Illumina | 2.48 | 60.1 | 2,570 |
| 37 | HL059PA2 | Skin | 16 | IB | Illumina | 2.48 | 60.0 | 2,535 |
| 38 | HL060PA1 | Skin | 2 | II | Illumina | 2.48 | 60.1 | 2,601 |
| 39 | HL063PA1 | Skin | 1 | IA | Illumina | 2.48 | 60.1 | 2,520 |
| 40 | HL063PA2 | Skin | 3 | IB | Illumina | 2.53 | 60.0 | 2,669 |
| 41 | HL067PA1 | Skin | 3 | IB | Illumina | 2.53 | 60.1 | 2,633 |
| 42 | HL072PA1 | Skin | 5 | IA | Illumina | 2.53 | 60.1 | 2,594 |
| 43 | HL072PA2 | Skin | 5 | IA | Illumina | 2.53 | 60.1 | 2,672 |
| 44 | HL074PA1 | Skin | 4 | IA | Illumina | 2.53 | 60.2 | 2,723 |
| 45 | HL078PA1 | Skin | 1 | IA | Illumina | 2.58 | 60.1 | 2,785 |
| 46 | HL082PA1 | Skin | 8 | IB | Illumina | 2.50 | 60.1 | 2,648 |
| 47 | HL082PA2 | Skin | 2 | II | Illumina | 2.51 | 60.0 | 2,644 |
| 48 | HL083PA1 | Skin | 1 | IA | Illumina | 2.48 | 60.1 | 2,575 |
| 49 | HL083PA2 | Skin | 3 | IB | Illumina | 2.48 | 60.0 | 2,633 |
| 50 | HL086PA1 | Skin | 8 | IB | Illumina | 2.53 | 60.1 | 2,610 |
| 51 | HL087PA1 | Skin | 3 | IB | Illumina | 2.48 | 60.1 | 2,584 |
| 52 | HL087PA2 | Skin | 1 | IA | Illumina | 2.48 | 60.1 | 2,572 |
| 53 | HL087PA3 | Skin | 3 | IB | Illumina | 2.52 | 60.1 | 2,619 |
| 54 | HL092PA1 | Skin | 8 | IB | Illumina | 2.50 | 60.1 | 2,590 |
| 55 | HL096PA1 | Skin | 5 | IA | Roche/454 | 2.49 | 60.0 | 2,393 |
| 56 | HL096PA2 | Skin | 5 | IA | Illumina | 2.56 | 60.1 | 2,638 |
| 57 | HL096PA3 | Skin | 1 | IA | Illumina | 2.56 | 60.0 | 2.651 |
| 58 | HL097PA1 | Skin | 5 | IC | Illumina | 2.52 | 60.2 | 2,617 |
| 59 | HL099PA1 | Skin | 4 | IA | Illumina | 2.58 | 60.1 | 2,735 |
| 60 | HL100PA1 | Skin | 1 | IA | Illumina | 2.48 | 60.1 | 2,562 |
| 61 | HL103PA1 | Skin | 2 | II | Illumina | 2.48 | 60.1 | 2,546 |
| 62 | HL106PA1 | Skin | 2 | II | Illumina | 2.48 | 60.1 | 2,533 |
| 63 | HL106PA2 | Skin | 1 | IA | Illumina | 2.48 | 60.1 | 2,567 |

TABLE 5-continued

General features of the 82 P. acnes genomes

| Genome | Strain name | Origin | Ribotype | recA type | Sequencing method | Genome size (Mb) | GC % | Number of ORFs |
|---|---|---|---|---|---|---|---|---|
| 64 | HL110PA1 | Skin | 8 | IB | Illumina | 2.51 | 60.1 | 2,667 |
| 65 | HL110PA2 | Skin | 8 | IB | Illumina | 2.50 | 60.1 | 2,614 |
| 66 | HL110PA3 | Skin | 6 | II | Illumina | 2.54 | 60.1 | 2,806 |
| 67 | HL110PA4 | Skin | 6 | II | Illumina | 2.54 | 60.1 | 2,724 |
| 68 | HL201PA1 | Refractory endodontic lesion | 6 | III | Illumina | 2.48 | 60.1 | 2,629 |
| 69 | HL202PA1 | Refractory endodontic lesion | Not assigned | II | Illumina | 2.56 | 60.0 | 2,821 |
| 70 | KPA171202 | Plate | 1 | IB | Sanger | 2.56 | 60.0 | 2,297 |
| 71 | J139 | Skin | 2 | II | Roche/454 | 2.48 | 60.0 | 2,364 |
| 72 | J165 | Skin | 1 | IA | Roche/454 | 2.50 | 60.0 | 2,403 |
| 73 | SK137 | Skin | 1 | IA | Roche/454 | 2.50 | 60.0 | 2,352 |
| 74 | SK187 | Skin | 3 | IB | Roche/454 | 2.51 | 59.0 | 2,381 |
| 75 | SK182 | Skin | 1 | IA | Roche/454 | 2.48 | 60.0 | 2,338 |
| 76 | 266 | Pleuropulmonary infection | 1 | IA | Roche/454 | 2.50 | 60.0 | 2,412 |
| 77 | 6609 | Skin | 1 | IB | Solid | 2.56 | 60.0 | 2,358 |
| 78 | ATCC11828 | Abscess | 2 | II | Solid | 2.49 | 60.0 | 2,260 |
| 79 | P.acn17 | Corneal scrape | 3 | IB | Solid | 2.52 | 60.0 | 2,266 |
| 80 | P.acn31 | Aqueous humour | 3 | IB | Solid | 2.50 | 60.0 | 2,247 |
| 81 | P.acn33 | Aqueous humour | 3 | IB | Solid | 2.49 | 60.0 | 2,236 |
| 82 | PRP-38 | Skin | 5 | IC | Solid | 2.51 | 60.0 | 2,233 |

These 69 strains cover all the known P. acnes lineages isolated to date. The strains were classified based on their 16S ribosomal RNA (rRNA) sequences. Each unique 16S rRNA sequence was defined as a ribotype (RT). All the sequenced P. acnes genomes had three identical copies of 16S rRNA. Based on the metagenomic study of the skin microbiome associated with acne (4), among the top ten major ribotypes, RT1, RT2, and RT3 were the most abundant and found in both healthy individuals and acne patients with no significant differences. RT4, RT5, and RT8, however, were enriched in acne patients, while RT6 was mostly found in healthy individuals. The 69 strains included 19 RT1 strains, five RT2 strains, 15 RT3 strains, eight RT4 strains, seven RT5 strains, four RT6 strains, six RT8 strains, four strains of minor ribotypes, and one type Ill strain. The average genome size was 2.50 Mb (ranging from 2.46 to 2.58 Mb) and the GC content was 60%. On average, each genome encoded 2,626 ORFs (ranging from 2,393 to 2,806) (Table 5).

The analysis included 13 additional P. acnes genomes that were publicly available (14, 17-22) (Table 5). The average genome size of these 13 P. acnes strains was 2.51 Mb (ranging from 2.48 to 2.56 Mb) and the GC content was 60%, encoding 2,319 ORFs on average (ranging from 2,233 to 2,412). These 13 genomes include six RT1 strains, two RT2 strains, four RT3 strains, and one RT5 strain, however, no genomes of RT4, RT6, RT8 and type Ill strains were available. The sequencing effort significantly increased the number of genomes for each P. acnes lineage as well as the number of lineages covered.

P. acnes Pan-Genome

Figure 13:
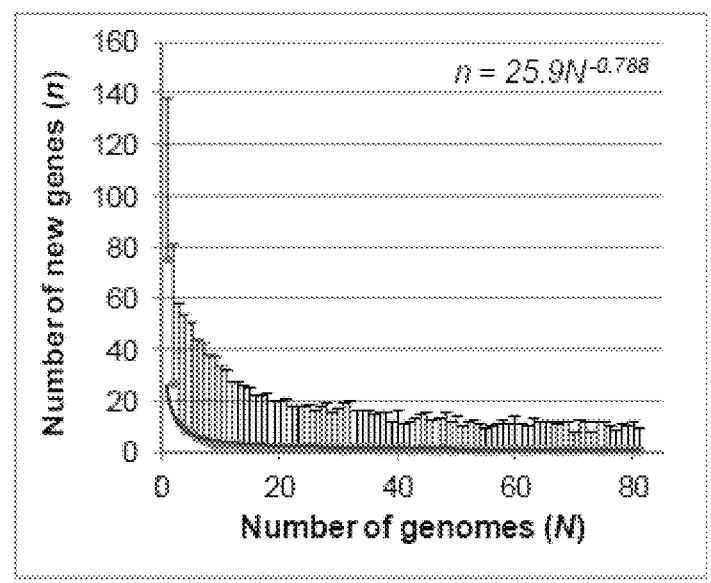
FIG. 13 shows a power law regression for new genes (n) discovered with the addition of new genome sequences (N). Circles are the medians of n for 200 simulations. Error bars indicate the standard deviations for the 200 simulations.
Figure 14:
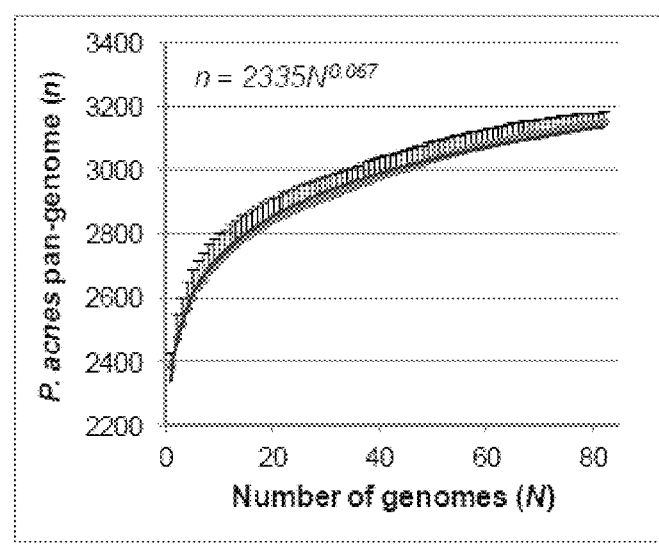
FIG. 14 shows a power law regression for total genes (n) accumulated with the addition of new genome sequences (N). Circles are the medians of n for 200 simulations. Error bars indicate the standard deviations for the 200 simulations.

To determine the genetic landscape of P. acnes, the pan-genome based on the 82 P. acnes genomes was estimated. The number of new genes that would be discovered by sequencing additional P. acnes genomes by using a power law regression analysis, $n=\kappa N^\gamma$ (24), was estimated (FIG. 13). The analysis identified that a was 0.788. The average number of new genes added by a novel genome was three when the 82nd genome was added. The number of P. acnes pan-genes that would be accumulated by sequencing additional P. acnes genomes by using a power law regression analysis, $n=\kappa N^\gamma$, was then estimated (FIG. 14). The exponent γ was 0.067, and P. acnes had 3,136 pan-genes (N=82). Based on these results, the pan-genome of P. acnes is defined as open, as the exponent a was less than one and γ was greater than zero (24). However, since a was close to one and γ was close to zero, it is believed that this organism evolved tightly without large expansions.

Phylogenetic Relationships Among the P. acnes Genomes

Figure 15:
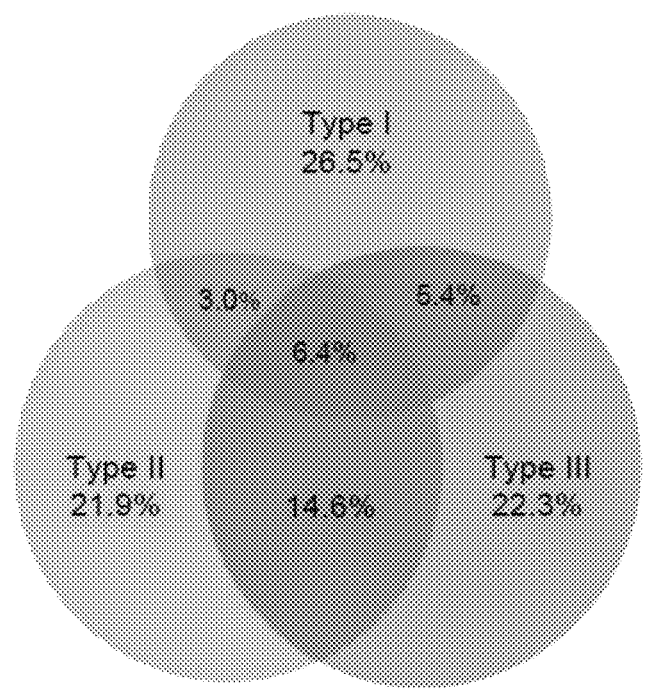
FIG. 15 shows the proportion of the 123,223 SNPs in the core regions specific to recA types I, Hand III.
Figure 16:
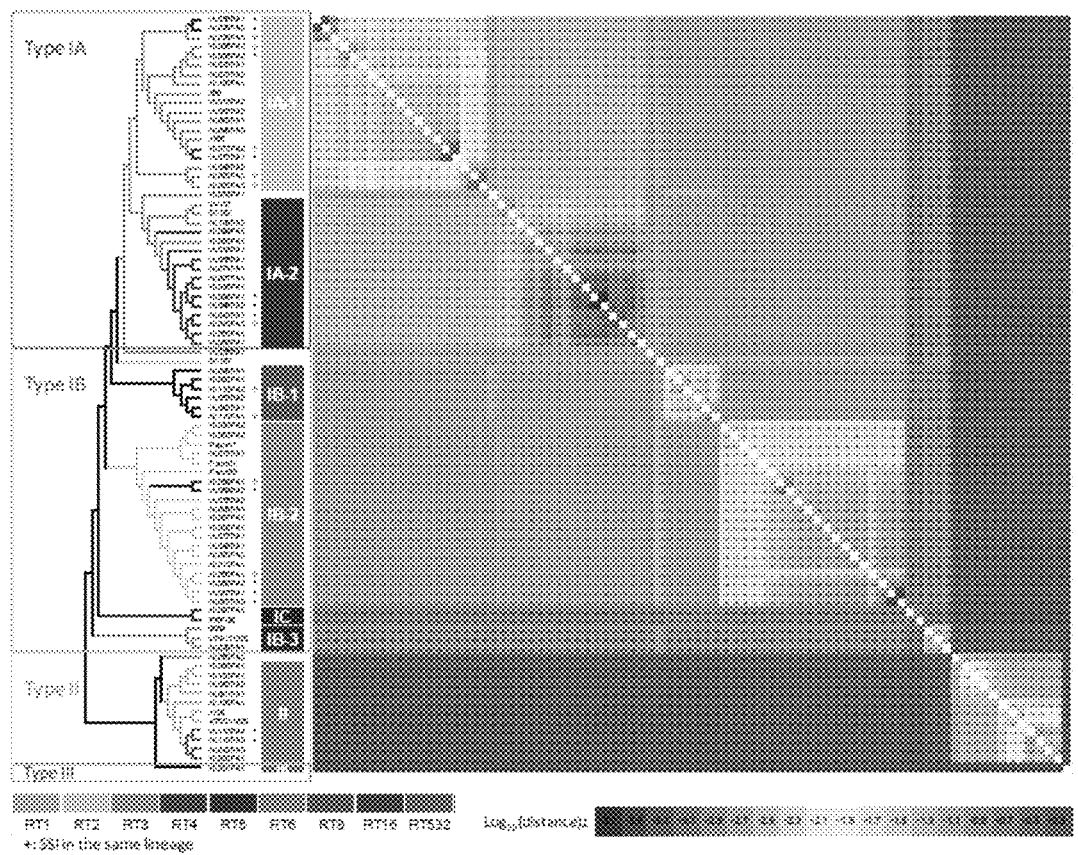
FIG. 16 shows the phylogenetic tree of 82 *P. acnes* strains constructed based on the 123,223 SNPs in the core regions (2.20 Mb). The distances between strains were calculated as nucleotide substitution rates at all SNP sites, colored according to the scale bar. The strains from the same individuals (SSIs) belonging to the same lineages were marked with "+".

A genome comparison of the 82 P. acnes strains revealed that 2.20 Mb (88% of the average genome) was shared by all the P. acnes genomes, which are referred to herein as the "core regions." Within the core regions, 123,223 unique single nucleotide polymorphisms (SNPs) were detected among the strains. Twenty seven percent of the SNPs were unique to type I, 22% were unique to type II, and 22% were unique to type III (FIG. 15). A phylogenetic tree based on the 123,223 SNPs in the core regions was constructed (FIG. 16). The tree showed that the recA type classification of the strains was consistent with the major clades based on the genomes. The recA type IA, IB, and II strains were all clustered together within each type, respectively, except HL097PA1 and PRP-38. The only recA type III strain, HL201PA1, formed a separate branch from type I and type II strains. The tree also showed that the 16S rRNA ribotypes of the strains were consistent with the phylogenetic relationships inferred from the genome sequences. Most of the RT1 strains were clustered in clade IA-1, while all the RT4 and most of the RT5 strains were clustered in clade IA-2. All six RT8 strains were clustered together in clade IB-1. All the RT3 and RT16 strains were clustered together in clade IB-2 except SK187. HL030PA1 and KPA171202 were clustered together with 6609, as a distinct IB-3 clade. HL097PA1 and PRP-38 were clustered together and were classified as a novel type IC recently named by McDowell et al. (22). All the RT2 strains were clustered in clade II, distant from clade I, together with RT6 strains. HL202PA1, which is a RT6 strain and was isolated from an oral site, was not much different from the skin RT6 isolates and was clustered together. The sequence types of all the strains were assigned based on two published MLST schemes (11,13) and are shown in Table 1. The phylogenetic tree based on the core genome regions demonstrated that 16S ribotyping can be used for P. acnes strain identification and classification. It provides a much higher resolution than recA typing, and in the meantime, it is much simpler and faster with only one gene required than MLST, which is a laborious process generally requiring 7-9 genes.

Figure 17:
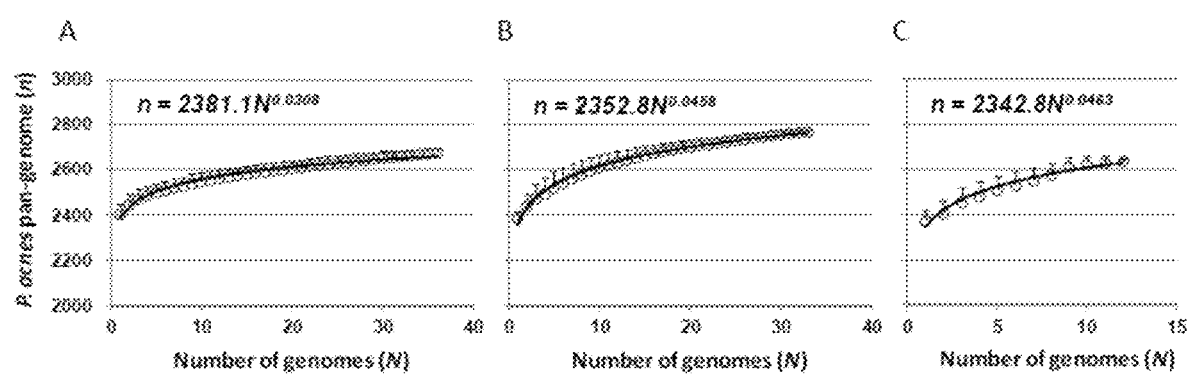
FIG. 17 shows the pan-genomes of types IA (A), IB (B) and II (C) strains. Circles are the medians of n for 200 simulations. Error bars are standard deviations for the 200 simulations.

The large number of genome sequences that were generated permitted analyzing the P. acnes pan-genome at the clade level. Clades IA, IB and II had 36, 33 and 12 genomes, respectively. Based on the power law regression analyses described above, it was determined that at the clade level P. acnes also has an open pan-genome for recA type IA clade, type IB clade and type II clade with limited expansions (FIG. 17). The expansion rates were not significantly different among the clades and were similar to the one at the species level. This suggests that all the major lineages of P. acnes had evolved at a similar rate.

SNP Distribution in the Core Genome Regions

Figure 18:
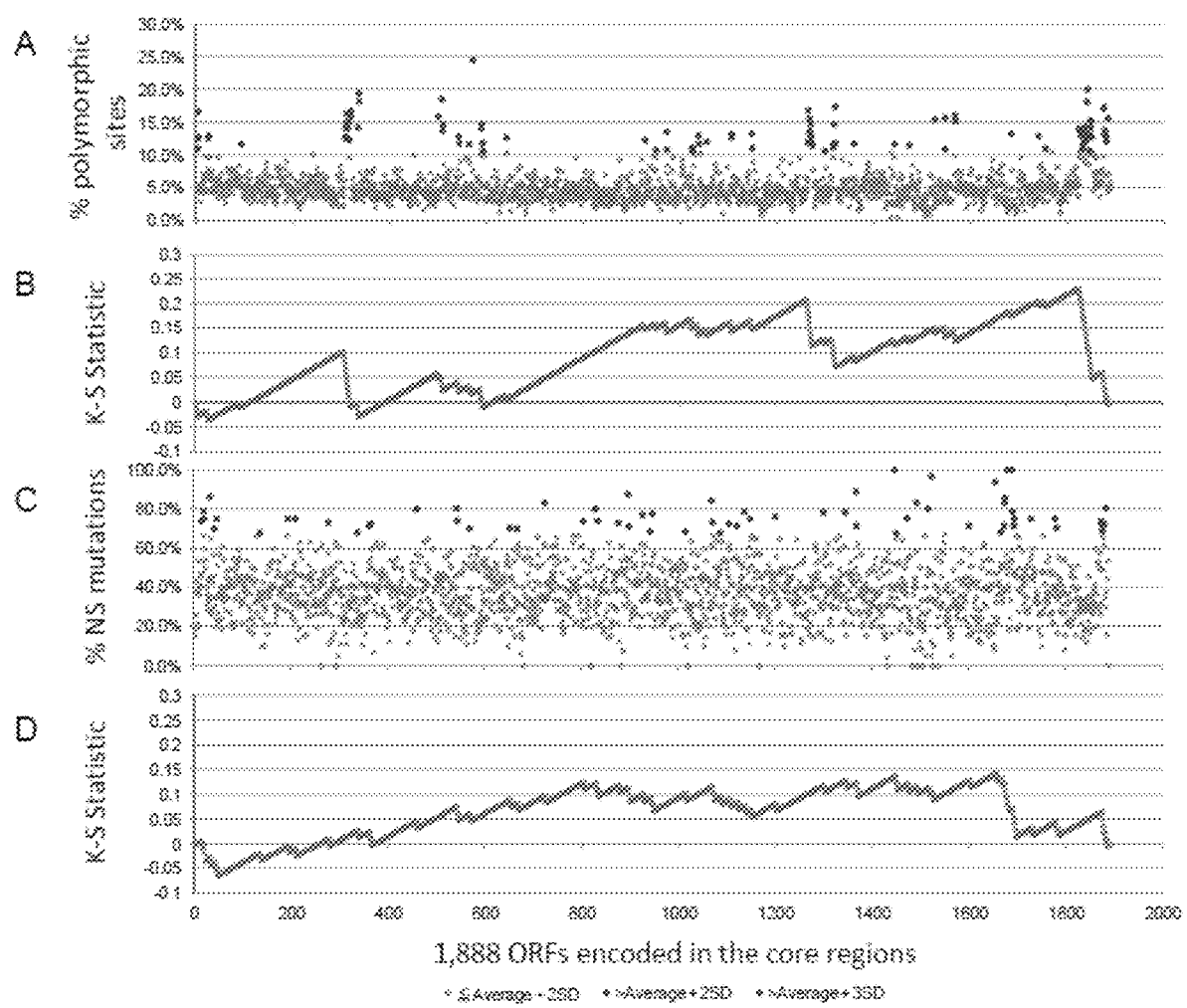
FIG. 18 shows the SNP distribution in core regions. (A) shows SNP frequencies (percentage of polymorphic sites) of the genes in the core regions. (B) provides K-S statistics for genes that had higher SNP frequencies with more than two standard deviations (SD). (C) reflects non-synonymous mutation frequencies of the genes in the core regions. (D) provides K-S statistics for genes that had higher non-synonymous mutation frequencies with more than 2 standard deviations.

To understand whether there are "hot spots" for mutation and/or recombination in the P. acnes genomes, it was determined whether the SNPs were randomly distributed throughout the genomes or were enriched in particular regions. The frequency of SNPs in each protein coding gene in the core regions was calculated. The average rate of polymorphic sites in the core regions was 5.3%, i.e., 5.3 unique SNPs in every 100 bp. This rate is comparable to the ones found in multiple gut bacterial genomes (25). Among the 1,888 genes encoded in the core regions, 55 genes had higher SNP frequencies with more than two standard deviations (SD), and 47 genes with more than three SD (FIG. 18(A). Using the Kolmogorov-Smirnov (K-S) test, it was demonstrated that these 102 highly mutated genes were not randomly distributed throughout the genome (P<0.01) (FIG. 18(B). This suggests that P. acnes has an evolutionary risk management strategy. Based on the Clusters of Orthologous Groups (COG) categories, the functions of these 102 genes showed a similar distribution as those of all 1,888 genes in the core regions. There was no enrichment of a particular functional category in these frequently mutated genes.

It was further determined whether the mutations in the core regions were under selection by calculating the ratio of non-synonymous (NS) vs. synonymous (S) SNPs for the 1,888 genes. The average rate of NS mutations was 38%. Among the 1,888 genes, 54 genes had higher NS mutation rates with more than two SD and 13 genes with more than three SD (FIG. 18(C). These 67 genes were randomly distributed in the genome and not particularly enriched in certain regions (P>0.05 with the K-S test) (FIG. 18(D). Most of the 102 genes with higher SNP frequencies did not overlap with these 67 genes, suggesting that independent evolutionary events might lead to these gene alternations. Only ten genes had both high SNP frequencies and high NS mutation rates, all annotated as hypothetical proteins.

Evolutionary Relationships of the Strains Isolated from the Same Individuals

The large number of P. acnes strains isolated from the cohort of acne patients and healthy individuals allowed the investigation of whether the P. acnes strains in hair follicles from the same individual were clonal. Based on previous metagenomic analysis, it was demonstrated that most individuals harbored multiple P. acnes strains from different lineages (4). However, it was not known whether the strains of the same lineage in the same individual were derived from the same ancestor. Genome sequences of the strains isolated from the same samples makes it possible to examine whether the Strains from the Same Individuals (SSIs) evolved from the same origin via clonal expansion. The 69 sequenced P. acnes strains included 49 SSIs: 13 duets (i.e., 13 pairs of strains isolated from 13 individuals), five trios, and two quartets. Twenty three SSIs were clustered in the same clades, nine in clade IA-1, four in clade IA-2, two in clade IB-1, six in clade IB-2 and two in clade II. The distance (substitution rate at the 123,223 SNP sites in the core regions) between each pair of SSIs was calculated (FIG. 16). The average distance of the SSIs in clade IA-1 was 0.0014, while that of strains from different individuals in clade IA-1 was 0.0064 (P<0.001). Consistent results were observed in other clades including IA-2, IB-1, IB-2, and II (FIG. 19(A)).This demonstrated that the SS's in the same lineage were significantly more similar to each other than the strains isolated from different individuals, suggesting that they were clonal in each individual. Among the RT4 and RT5 strains within clade IA-2, however, the average distance between SS's (0.0004) was not significantly different from the average distance between strains from different individuals (0.0017) (P=0.072). Moreover, the average distance between RT4/RT5 strains from different individuals (0.0017) was similar to the average distance between the SSIs in clade IA-1 (0.0014), and even shorter than the average distances between the SS's in clades IB-1 (0.0059), IB-2 (0.0019) and II (0.0022) (FIG. S3A). This suggests that although isolated from different individuals, these RT4 and RT5 strains seemed to be clonal and had evolved from the same recent ancestor. A similar relationship between the two RT5 strains in clade IC were observed, where HL097PA1 and PRP-38, isolated from different individuals, were closely related to each other with a distance of 0.0012. The metagenomic study has demonstrated a strong association of strains of RT4 and RT5 with acne (4). The clonality of these strains isolated from different individuals suggests that RT4 and RT5 strains may be transmitted among individuals. This finding is consistent with the previous clinical report that antibiotic-resistant Propionibacteria were transmissible between acne-prone individuals including dermatologists (26), as most of the antibiotic-resistant P. acnes strains belong to RT4 and RT5 (4,13). The analysis of SSIs further supports the theory that RT4 and RT5 strains may be a pathogenic factor in acne.

To determine whether the distances between strain pairs from the same individuals but belonging to different lineages were different from random strain pairs, the distances of any pair of SSIs from different clades were calculated. The average distance of the SS's between clades IA-1 and IA-2 (i.e., HL005PA3 vs. HL005PA1, HL005PA2 vs. HL005PA1, HL096PA3 vs. HL096PA1, and HL096PA3 vs. HL096PA2) was 0.039, similar to that of the isolates from different individuals (0.040). Similar results were obtained for all other clade pair comparisons (FIG. 19(B). These results demonstrated that the SSIs from different clades were similarly different from each other as to the strains from different individuals. This analysis suggests that in each individual microbiome P. acnes strains undergo clonal expansion in the same population, while multiple strain populations can often co-exist in the same community with little recombination.

Non-Core Genome Regions in Type I Strains

By comparing the genome sequences of the 82 P. acnes strains, non-core genome regions were identified that were not shared by all 82 strains. The total length of the non-core regions was approximately 0.90 Mb. The average GC content of the non-core regions was slightly lower than that of the core regions, 58%±6.9%, suggesting that part of the non-core regions might be originated from other species via horizontal gene transfer.

Figure 20:
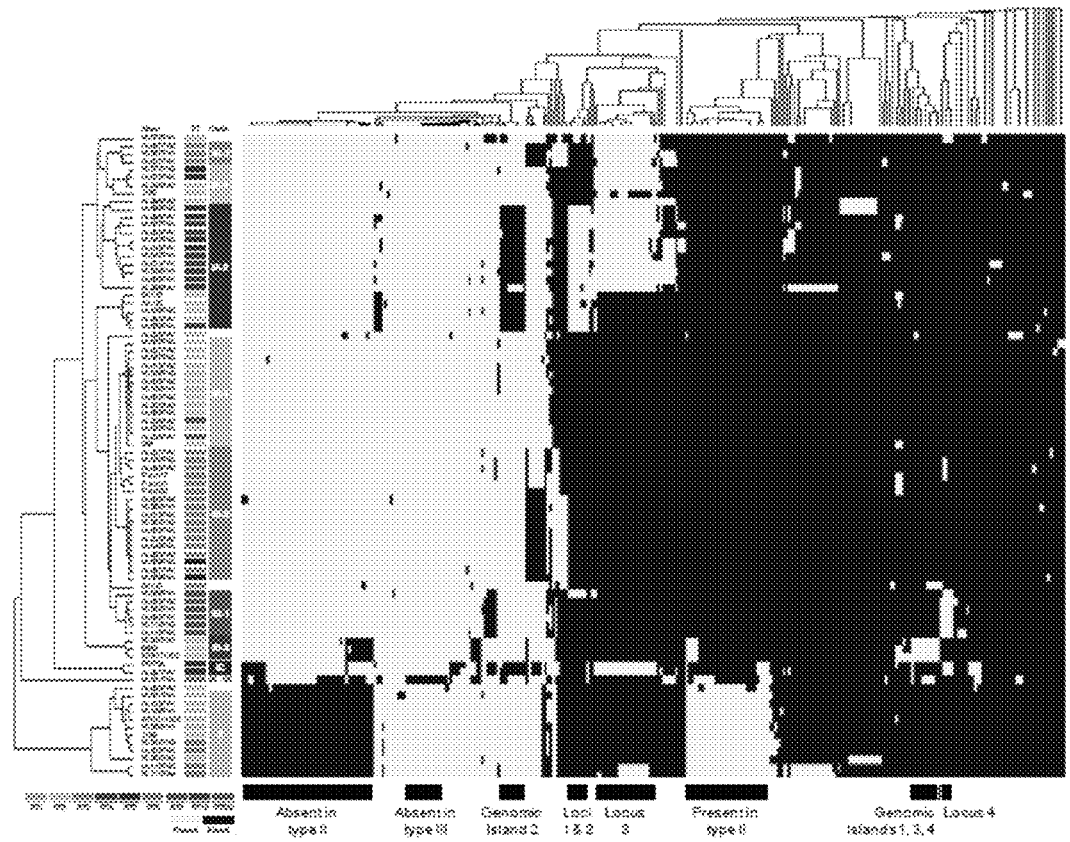
FIG. 20 reflects that *P. acnes* strains within each lineage share unique non-core genomic regions. Rows represent 82 *P. acnes* genomes and columns represent 314 non-core regions that are longer than 500 bp. The genomes and the non-core regions were clustered based on similarity, respectively. The width of each block plotted is not proportional to the genomic length of each non-core region. The presence of a non-core region is colored in yellow, and the absence is colored in blue. The color schemes used for RT and clades are the same as in FIG. 16.

Different lineages of P. acnes strains have distinct non-core regions. Using hierarchical clustering of the non-core regions, it was shown that the strains of the same ribotypes were clustered together with distinct separations among the clades (FIG. 20). Among the non-core regions, the genetic elements specific to each lineage were identified, which may explain the phenotypic and functional differences of the strains in health and disease. In clade IA-2, genomic loci 1, 2 and 3 were identified, which were unique to mainly the RT4 and RT5 strains (4). These loci appear to be originated from mobile elements, encode several virulent genes, and may contribute to the virulence of these strains. In the meantime, the genomic island-like cluster 2 (GI2) (18) was uniquely absent in most of the strains in this clade. Clade IB-1 consisted of all RT8 strains, which were also highly associated with acne based on our metagenomic study (4). They all have a unique genomic island (locus 4), which is 20 Kb long and encodes a series of nonribosomal peptide synthetases (NRPS), which may contribute to increased virulence of these strains. Most RT3 and RT16 strains belong to clade IB-2 and have fewer non-core regions than the strains in other clades. This may be explained by the lack of entire rearrangement hot spot (RHS) family proteins, which function in genomic rearrangements as previously implicated in *Escherichia coli* (27). Clade IB-3 consisted of three strains, including KPA171202. Three of the four genomic islands described previously (18), GI1, GI3 and GI4, were unique to this clade and were absent in all other strains. This analysis suggests that KPA171202, although was the first sequenced complete genome of *P. acnes*, did not seem to be a common skin *P. acnes* strain representing one of the major lineages. This result is consistent with previous studies using MLST (11-13). Strains of clade IC belong to RT5. They also contain locus 3, a linear plasmid, which is highly homologous to the locus 3 in the RT4 and RT5 strains of clade IA-2 and encodes a tight adhesion locus originated from *Clostridium leptum* (4). In general, although strains in different lineages had a similar genome size with similar gain and loss of genetic materials, they harbor distinct genetic elements which may give rise to their different virulent properties.

Non-Core Genome Regions in Type II Strains

Strains in clade II, mainly RT2 and RT6, were more distantly related to the strains in clade I. Based on the metagenomic study, strains in clade II were not associated with acne, as RT2 was evenly distributed between acne patients and healthy individuals, while RT6 was significantly enriched in healthy individuals (4). Compared to type I strains, the genomes of RT2 and RT6 strains lack several regions, which are approximately 92 Kb long in total and encode 107 ORFs. RT2 and RT6 genomes have additional genomic regions with a similar size encoding 93 ORFs (FIG. 20). Based on the COG classification, there were no significant differences in the distribution of the functional categories between the 107 type I specific ORFs and 93 type II specific ORFs.

The most unique genomic feature of RT2 and RT6 strains is represented by the clustered regularly interspaced short palindromic repeats (CRISPR)/Cas locus (4). CRISPR/Cas system provides acquired bacterial immunity against viruses and plasmids by targeting nucleic acids in a sequence-specific manner (28). All the sequenced strains of RT2 and RT6 encoded a complete set of CRISPR/Cas genes and at least one repeat and spacer sequence, while none of the other ribotype strains did. Based on its complete genome sequence (20), strain ATCC11828 appeared to be an exception, having only terminal sequence but no spacer sequence. However, using PCR and sequencing it was determined that ATCC11828 has one repeat-spacer sequence (Table 4).

TABLE 4

CRISPR spacer sequences found in the genomes of ATCC 11828, HL042PA3 and HL202PA1.

| Strain | Ribotype | Spacer | Protspacer | BLAST result | Match found in |
|---|---|---|---|---|---|
| ATCC11828 | RT2 | 1 | CATCTGCCAACGAGCGAGAGTGGCGCGGTGTTC | No hits | |
| | | 2 | CGAGGGCTACCACGTGGTCGATTTGGACTGTCG | Clostridium leptum DSM 753, CLALEP_00167, Propionibacterium acnes SK137, HMPREF0675_3193 (Domain unknown fucntion) | Locus 2 |
| | | 3 | CAGGCGCTCCACTCCCTCGCCCTGGCCACCAAC | No hits | |
| HL042PA3 | RT6 | 1 | CTGACTGGTTTGGGTCATACGTCTTCTGACACG | Propionibacterium acnes phage PA6 gp14 (tape measure protein) Propionibacterium acnes phage PAD20 gp14 (Tape measure protein) Propionibacterium acnes phage PAS50 gp14 (Tape measure protein) | |
| | | 2 | TCACAGGCCACGCAGGCACATCACCCTTATTAG | Propionibacterium acnes phage PA6 gp15 (Minor tail protein) Propionibacterium acnes phage PAD20 gp15 (Minor tail protein) Propionibacterium acnes phage PAS50 gp15 (Minor tail protein) | |
| | | 3 | CTCCCCCTCCTCCCCGGAGGAAAAGCAGACCA | Propionibacterium acnes phage PAS50 gp15 (Minor tail protein) | |
| | | 4 | CGAGGGCTACCACGTGGTCGATTTGGACTGTCG | Clostridium leptum DSM 753, CLOLEP_00167, Propionibacterium acnes SK137, HMPREF0675_3193 (Domain of unknown function) | Locus 2 |
| HL202PA1 | RT6 | 1 | CGAGGGCCTACCACGTGGTCGATTTGGACTGTCG | Clostridium leptum DSM 753, CLOLEP_00167, Propionibacterium acnes SK137, HMPREF0675_3193 (Domain of unknown function) | Locus 2 |
| | | 2 | CAGGCGCTCCACTCCCTCGCCCTGGCCACCAAC | No hits | |

Figure 21:
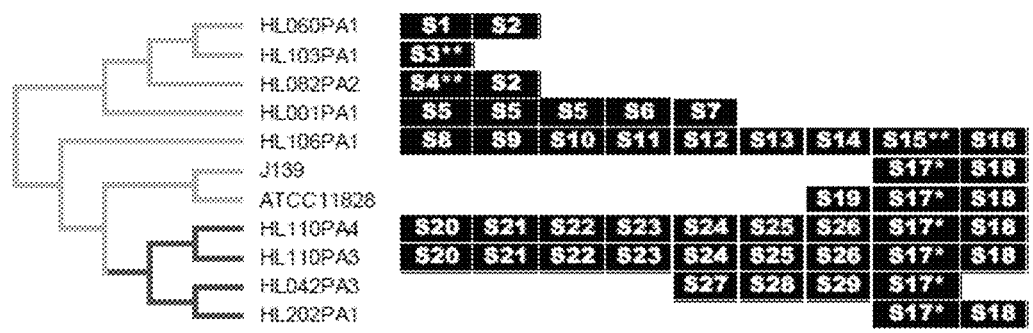
FIG. 21 provides CRISPR spacer sequences in RT2 and RT6 strains. A total of 48 CRISPR spacer sequences were found in 11 *P. acnes* genomes, 29 of which were unique. Some CRISPR spacers were found in multiple strains. For example, spacer 2 (S2) was shared by HL060PA1 and HL082PA2. Spacer 17 (S17) was shared by J139, ATCC11828, HL110PA3, HL110PA4, HL042PA3 and HL202PA1. Spacer 18 (S18) was shared by J139, ATCC11828, HL110PA3, HL110PA4, and HL202PA1. The tree was from FIG. 16 constructed based on the 123,223 SNPs in the core regions.

A total of 48 spacer sequences were found in the 11 RT2 and RT6 strains, 29 of which were unique. In other bacterial species, it has been established experimentally and computationally that the spacers at the leader-proximal end are more diversified, while the spacers at the leader-distal end are more conserved among strains. The evolutionary relationships among the RT2 and RT6 strains based on their shared spacer sequences were analyzed. HL060PA1 and HL082PA2, which were clustered tightly in clade II, shared the same spacer S2 (FIG. 21). J139, ATCC11828, HL110PA4, HL110PA3, and HL202PA1 shared the same spacers S17 and S18 (FIG. 21). These results suggest that these groups of strains probably evolved from the same ancestors before having acquired additional spacers. The relationships among the strains based on shared CRISPR spacers are consistent with the phylogenetic relationships calculated based on the SNPs in the core regions. In addition, multiple type II strains harbored spacer sequences that match to the sequences in loci 2 and 3, which were unique to mainly acne-associated RT4 and RT5 strains (4). The sequences in loci 2 and 3 appeared to be originated from *C. leptum* and encode potential virulence factors (Figure S4). These loci may have been acquired by RT4 and RT5 strains, while the genomes of RT2 and RT6 that encode these spacers may be capable of eliminating the invasion of foreign DNA through the CRISPR mechanism (4).

The large number of high quality draft genome sequences enabled detection not only large genomic variations, but also small but essential genomic alterations. It was previously reported that type II strains showed decreased lipase activity (10). Lipase functions in hydrolyzing triglycerides and releasing free fatty acids, which is thought to be essential in *P. acnes* virulence. Based on the genome annotation, 13 genes were identified with a potential function of lipase (FIG. 22(A)). Among them, detected insertions/deletions ranging from one nucleotide to 13 nucleotides may explain the decreased lipase activity in type II strains. Two triacylglycerol lipases were encoded in tandem in *P. acnes* genomes, HMPREF0675-4855 and HMPREF0675-4856 (according to the annotation of SK137). All the type II strains and IB-3 strains had a deletion of the "TATA-box" 20 bp upstream of the start codon of the second lipase gene, HMPREF0675-4856 (FIG. 22(B)). In addition, there was a one-nucleotide deletion at the position of 124G of the second lipase gene, leading to a frameshift and the introduction of a premature stop codon. These two deletions may potentially explain the decreased lipase activity and hence decreased virulence in acne observed in type II strains in previous studies (4, 10).

Non-Core Genome Regions in the Type III Strain

Type III strains are rarely found on the skin surface. A type III *P. acnes* strain isolated from refractory endodontic lesion, HL201PA1, was sequenced. This first available type III genome permitted the identification of the genetic elements specific to this lineage. Compared to type I and type II strains, the genome of HL201 PA1 lacks a few regions with a total length of 43 Kb (FIG. 20). There were 42 ORFs encoded in these regions, including anaerobic dimethyl sulfoxide reductase (PPA0516-PPA0517), iron(III) dicitrate transport system permease (PPA0792-PPA0793), 3-isopropylmalate dehydratase (PPA1361-PPA1363), and maltose transport system permease (PPA1553-PPA1554).

Discussion

High-throughput genome sequencing and comparative analysis of a large number of related strains have been used to study the spread and microevolution of several pathogens at the strain level, including methicillin-resistant *Staphylococcus aureus* (29), *Streptococcus pneumoniae* (30), and *Vibrio cholerae* in Haiti outbreak (31), demonstrating the power of comparative genome analysis of multiple strains in improving our understanding of the bacterial pathogens. However, this approach has been rarely applied to study commensal species to understand their varied virulent potentials among different strains and their roles in both health and diseases.

This study presents a comparative genome analysis of a major skin commensal, *P. acnes*, based on a large number of sequenced strains. This collection of strains not only includes strains associated with either healthy skin or acne, but also a large number of strain pairs that were isolated from the same individuals. This allowed the comparison of phylogenetic relationships and microevolution of the *P. acnes* strains associated with health vs. disease as well as of the strains in the same individual microbiome.

By comparing 82 *P. acnes* genomes, it was shown that all *P. acnes* strains had a similar genome size with a similar GC content, encoding 2,577 ORFs on average (Table 2). Although *P. acnes* has an open pan-genome, unlike many other open-genome species (24), it has limited genome expansion with only a few new genes added per genome (FIGS. 13 and 14). The rate of genome expansion is similar within the major lineages (FIG. 17). There was limited recombination among different *P. acnes* strains, and thus 16S rRNA ribotypes can be used as a proxy for *P. acnes* strain identification and classification (FIG. 16). Compared to other typing methods, 16S ribotyping has a much higher resolution than recA typing and is much easier and faster than the traditional MLST method. This method can be applied in a high-throughput manner by combining with next-generation sequencing, and thus allows one to detect the microbiome variations at the strain level (4). This is advantageous and important, as identifying and understanding the strain level variations of the human microbiome is medically important.

Figure 19:
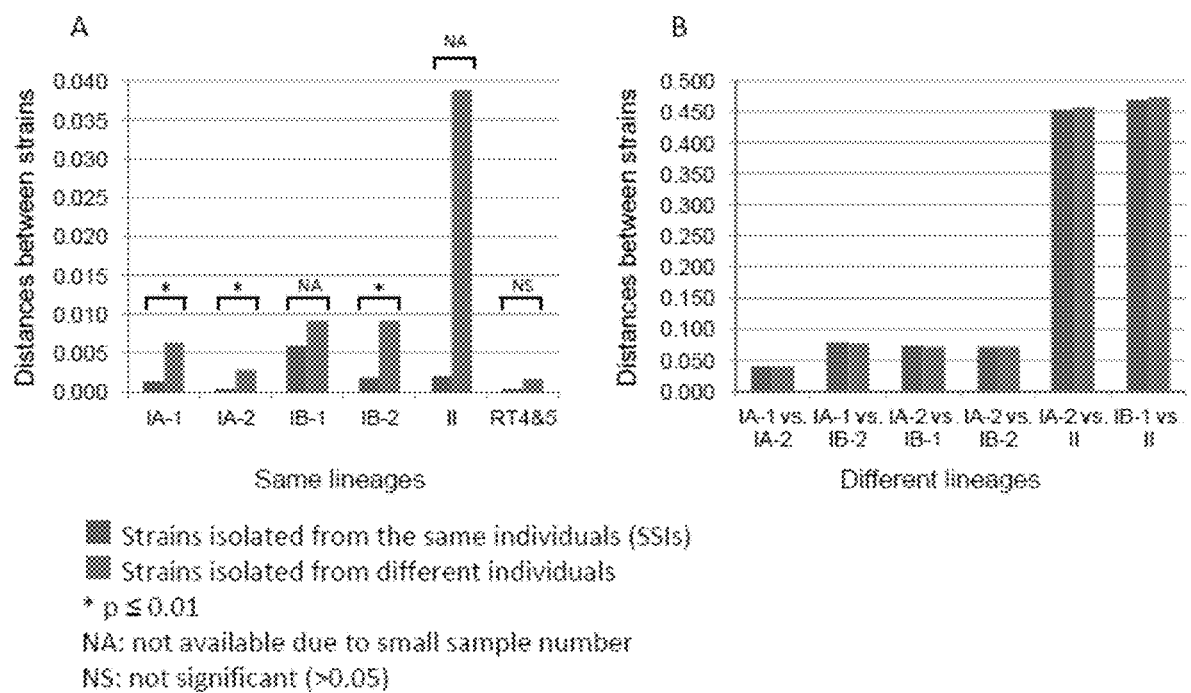
FIG. 19 provides the distances between *P. acnes* strains in the same lineage (A) and in different lineages (B).

The genomes of the sets of strains isolated from the same individual samples were compared (FIGS. 16 and 19). This collection of genome data is unique and no such kind of study has been performed to investigate the microevolution of a human commensal within an individual microbiome. It was found that while multiple *P. acnes* strain populations co-existed in the same individual microbiome, clonal expansions occurred in each population with little recombination among different populations. Within each lineage, the strains isolated from the same individuals were significantly more similar to each other than strains from different individuals except the disease associated strains, RT4 and RT5 strains (FIG. 19). Although isolated from different individuals, they appeared to be clonal and have evolved from the same virulent ancestor strain (FIG. 16). This supports the observation that these strains were transmissible (26) and that they may play a role in acne pathogenesis (4). This finding is important and will help control the spread of antibiotic resistant strains and develop new targeted therapy for acne.

Figure 22:
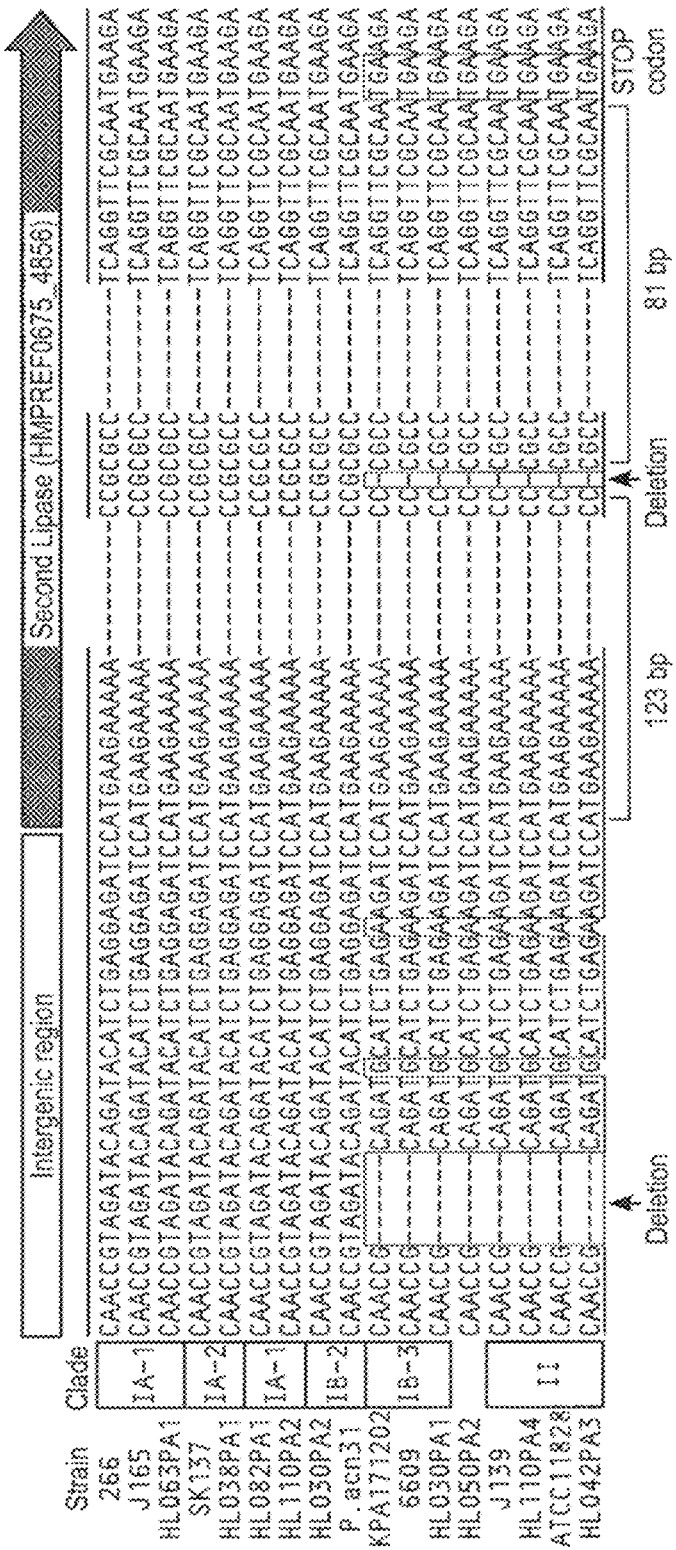
FIG. 22 reflects genes with putative lipase activity in the *P. acnes* genomes. (A) gives a summary of 13 genes with putative lipase activity based on the annotations of KPA171202 and SK137 genomes. (B) reflects Insertions/deletions and frameshift observed in ORF HMPREF0675-4856.

By analyzing the non-core regions, the genomic elements and alterations specific to each lineage were identified (FIG. 20). These lineage-specific elements may render the strains different physiological and functional properties and thus lead to their different roles as a commensal in health or as a pathogen in diseases. Among the acne associated strains, RT4 and RT5 strains encode three distinct loci originated from mobile elements, and RT8 strains encode a distinct region containing a set of NRPS. The virulent genes encoded in these strain-specific regions may explain the associations of these strains with acne and help the development of new drugs targeting against these strains. RT2 and RT6 strains, which were not associated with acne and were enriched in healthy skin, respectively, all encode CRISPR/cas elements. The CRISPR mechanism may prevent these strains from acquiring virulent genes from invading foreign mobile elements. In addition, these strains contain genomic variations in lipases that may alter lipid metabolism and reduce their virulence (FIG. 22).

In conclusion, by characterizing the genetic landscape and diversity of P. acnes with a large number of genomes, genomic evidence that may explain the diverse phenotypes of P. acnes strains and a new insight into the dual role of this commensal in human skin health and disease is provided. The findings from this comparative genome analysis provide new perspectives on the strain diversity and evolution of commensals in the human microbiome. As many current microbiome studies focus on the associations of microbial communities with health and diseases, this study underscores the importance of understanding the commensal microbiome at the strain level (25). The findings from this study also shed light on new strain-specific therapeutics for acne and other P. acnes associated diseases.

Materials and Methods

P. acnes Strains

Among the 69 P. acnes strains that were sequenced, 67 were isolated from the skin microcomedone samples from acne patients and healthy individuals (4). The other two strains, HL201PA1 and HL202PA1, were isolated from refractory endodontic lesions (23), provided by Dr. David Beighton at the King's College London.

Whole Genome Shotgun Sequencing, Assembly, and Annotation

The genome of HL042PA3 was sequenced using Roche/454 FLX and assembled using a combination of PHRAP/CONSED (32) and GSMAPPER (Roche).

HL201PA1 and HL202PA1 were sequenced using Illumina MiSeq (250 bp, paired-end) and assembled using Velvet (33). The remaining 66 genomes were sequenced previously as described (4). Coding sequences were predicted using GeneMark (34) and GLIMMER (35).

Computation of the Core Regions, Non-Core Regions and the Pan-Genome

The core regions were defined as genome sequences that were present in all 82 genomes, while the non-core regions were defined as genome sequences that were not present in all the genomes. KPA171202 was used as the reference genome. Each of the other 81 genome sequences (a series of contigs in most of the genomes and ten complete genomes) was mapped to the reference genome using Nucmer (36). All the 81 ".coords" output files of Nucmer program were analyzed to identify overlap regions based on the KPA171202 coordinates using a Perl script. Core sequences were then extracted based on the genome sequence of KPA171202 with the coordinates calculated above.

The unique regions from each genome were added to the reference genome to make a "revised" reference genome, which contained the original sequence plus the unique genome sequences. This process was repeated for all the genomes until all the unique regions from all genomes were included in the pan-genome.

Lastly, core regions were subtracted from the pan-genome. The remaining regions were defined as non-core regions, which are not shared by all the strains. Protein coding sequences were predicted by GeneMark.hmm using KPA171202 as a reference file.

Identification of SNPs in the Core Regions

Single nucleotide polymorphisms (SNPs) were identified by using "show-snps" utility option of the Nucmer program with the default settings (36). Genome sequence of KPA171202 was used as the reference genome. All the 81 ".snps" output files of Nucmer program were analyzed to identify unique SNP positions based on the KPA171202 coordinates using a Perl script.

Phylogenetic Tree Construction

The 82 concatenated sequences of the 123,223 SNP nucleotides in the core region were used to construct a phylogenetic tree of the P. acnes genomes. MEGA5 (37) was used to calculate the distance based on the SNPs in the core regions using the Neighbor-Joining method and the p-distance method. The bootstrap tree inferred from 200 replicates was taken.

Sequence Type Analysis Based on MLST Schemes

The sequence types of the 82 isolates were determined based on the MLST schemes published previously (11-13). The MLST gene sequences were aligned using BLAST against all the alleles used in the two MLST schemes.

Identification of CRISPR/Cas

CRISPRFinder (38) was used to identify the CRISPR repeat-spacer sequences. The annotation of HL110PA3 was used for BLAST alignment in order to identify the presence of CRISPR/Cas structure and CRISPR repeat-spacer sequences in strains of HL001PA1, HL060PA1, HL042PA3, HL082PA2, HL103PA1, HL106PA1, HL110PA4, HL202PA1, J139 and ATCC11828. Each spacer sequence was annotated by BLAST (39) against NCBI's non-redundant nucleotide database and the reference genomic sequences database (refseq_genomic).

Hierarchical Clustering Analysis of the Non-Core Regions

Among the 1,685 non-core fragments (895,905 bp in total), 314 non-core fragments with a length of >500 bp (747,189 bp in total, corresponding to 83% of all the non-core regions) were extracted and used in hierarchical clustering of the non-core regions. Cluster 3.0 program (40) and average linkage method was used. The clustering matrix was composed of 314 rows and 82 columns, in which 1 denotes presence of the non-core region and 0 denotes absence of the non-core region. Java TreeView program (41) was used to display the clustering result.

REFERENCES

1. Grice E A, Segre J A. 2011. The skin microbiome. Nat Rev Microbiol 9:244-253.
2. White G M. 1998. Recent findings in the epidemiologic evidence, classification, and subtypes of acne vulgaris. J Am Acad Dermatol 39:S34-37.
3. precedings.nature.com/documents/5305/version/1
4. Fitz-Gibbon S T, Tomida S, Chiu B, Nguyen L, Du C, Liu M, Elashoff D, Erfe M C, Loncaric A, Kim J, Modlin R L, Miller J F, Sodergren E, Craft N, Weinstock G M, Li H. Propionibacterium acnes strain populations in the human skin microbiome associated with acne. Journal of Investigative Dermatology (in press).
5. Chambers H F, Deleo F R. 2009. Waves of resistance: Staphylococcus aureus in the antibiotic era. Nat Rev Microbiol 7:629-641.
6. Chase-Topping M, Gaily D, Low C, Matthews L, Woolhouse M. 2008. Super-shedding and the link between human infection and livestock carriage of Escherichia coli 0157. Nat Rev Microbiol 6:904-912.
7. Johnson J L, Cummins C S. 1972. Cell wall composition and deoxyribonucleic acid similarities among the anaerobic coryneforms, classical propionibacteria, and strains of *Arachnia propionica*. J Bacteriol 109:1047-1066.
8. McDowell A, Valanne S, Ramage G, Tunney M M, Glenn J V, McLorinan G C, Bhatia A, Maisonneuve J F, Lodes M, Persing D H, Patrick S. 2005. *Propionibacterium acnes* types I and II represent phylogenetically distinct groups. J Clin Microbiol 43:326-334.
9. Valanne S, McDowell A, Ramage G, Tunney M M, Einarsson G G, O'Hagan S, Wisdom G B, Fairley D, Bhatia A, Maisonneuve J F, Lodes M, Persing D H, Patrick S. 2005. CAMP factor homologues in *Propionibacterium acnes*: a new protein family differentially expressed by types I and II. Microbiology 151:1369-1379.
10. McDowell A, Perry A L, Lambert P A, Patrick S. 2008. A new phylogenetic group of *Propionibacterium acnes*. J Med Microbiol 57:218-224.
11. Lomholt H B, Kilian M. 2010. Population genetic analysis of *Propionibacterium acnes* identifies a subpopulation and epidemic clones associated with acne. PLoS One 5:e12277.
12. McDowell A, Gao A, Barnard E, Fink C, Murray P I, Dowson C G, Nagy I, Lambert P A, Patrick S. 2011. A novel multilocus sequence typing scheme for the opportunistic pathogen *Propionibacterium acnes* and characterization of type I cell surface-associated antigens. Microbiology 157:1990-2003.
13. McDowell A, Barnard E, Nagy I, Gao A, Tomida S, Li H, Eady A, Cove J, Nord C E, Patrick S. 2012. An Expanded Multilocus Sequence Typing Scheme for *Propionibacterium acnes*: Investigation of 'Pathogenic', 'Commensal' and Antibiotic Resistant Strains. PLoS One 7:e41480.
14. Bruggemann H, Henne A, Hoster F, Liesegang H, Wiezer A, Strittmatter A, Hujer S, Durre P, Gottschalk G. 2004. The complete genome sequence of *Propionibacterium acnes*, a commensal of human skin. Science 305:671-673.
15. The Human Microbiome Project Consortium. 2012. A framework for human microbiome research. Nature 486:215-221.
16. The Human Microbiome Project Consortium. 2012. Structure, function and diversity of the healthy human microbiome. Nature 486:207-214.
17. Nelson K E, Weinstock G M, Highlander S K, Worley K C, Creasy H H, Wortman J R, Rusch D B, Mitreva M, Sodergren E, Chinwalla A T, Feldgarden M, Gevers D, Haas B J, Madupu R, Ward D V, Birren B W, Gibbs R A, Methe B, Petrosino J F, Strausberg R L, Sutton G G, White O R, Wilson R K, Durkin S, Giglio M G, Gujja S, Howarth C, Kodira C D, Kyrpides N, Mehta T, Muzny D M, Pearson M, Pepin K, Pati A, Qin X, Yandava C, Zeng Q, Zhang L, Berlin A M, Chen L, Hepburn T A, Johnson J, McCorrison J, Miller J, Minx P, Nusbaum C, Russ C, Sykes S M, Tomlinson C M, Young S, Warren W C, Badger J, Crabtree J, Markowitz V M, Orvis J, Cree A, Ferriera S, Fulton L L, Fulton R S, Gillis M, Hemphill L D, Joshi V, Kovar C, Torralba M, Wetterstrand K A, Abouellleil A, Wollam A M, Buhay C J, Ding Y, Dugan S, FitzGerald M G, Holder M, Hostetler J, Clifton S W, Allen-Vercoe E, Earl A M, Farmer C N, Liolios K, Surette M G, Xu Q, Pohl C, Wilczek-Boney K, Zhu D. 2010. A catalog of reference genomes from the human microbiome. Science 328:994-999.
18. Brzuszkiewicz E, Weiner J, Wollherr A, Thurmer A, Hupeden J, Lomholt H B, Kilian M, Gottschalk G, Daniel R, Mollenkopf H J, Meyer T F, Bruggemann H. 2011. Comparative genomics and transcriptomics of *Propionibacterium acnes*. PLoS One 6:e21581.
19. Hunyadkurti J, Feltoti Z, Horvath B, Nagymihaly M, Voros A, McDowell A, Patrick S, Urban E, Nagy I. 2011. Complete genome sequence of *Propionibacterium acnes* type I B strain 6609. J Bacteriol 193:4561-4562.
20. Horvath B, Hunyadkurti J, Voros A, Fekete C, Urban E, Kemeny L, Nagy I. 2012. Genome sequence of *Propionibacterium acnes* type I I strain ATCC 11828. J Bacteriol 194:202-203.
21. Voros A, Horvath B, Hunyadkurti J, McDowell A, Barnard E, Patrick S, Nagy I. 2012. Complete genome sequences of three *Propionibacterium acnes* isolates from the type I A(2) cluster. J Bacteriol 194:1621-1622.
22. McDowell A, Hunyadkurti J, Horvath B, Voros A, Barnard E, Patrick S, Nagy I. 2012. Draft genome sequence of an antibiotic-resistant *Propionibacterium acnes* strain, PRP-38, from the novel type I C cluster. J Bacteriol 194:3260-3261.
23. Niazi S A, Clarke D, Do T, Gilbert S C, Mannocci F, Beighton D. 2010. *Propionibacterium acnes* and *Staphylococcus epidermidis* isolated from refractory endodontic lesions are opportunistic pathogens. J Clin Microbiol 48:3859-3869.
24. Tettelin H, Riley D, Cattuto C, Medini D. 2008. Comparative genomics: the bacterial pan-genome. Curr Opin Microbiol 11:472-477.
25. Schloissnig S, Arumugam M, Sunagawa S, Mitreva M, Tap J, Zhu A, Waller A, Mende D R, Kultima J R, Martin J, Kota K, Sunyaev S R, Weinstock G M, Bork P. 2013. Genomic variation landscape of the human gut microbiome. Nature 493:45-50.
26. Ross J I, Snelling A M, Carnegie E, Coates P, Cunliffe W J, Bettoli V, Tosti G, Katsambas A, Galvan Perez Del Pulgar J I, Rollman O, Torok L, Eady E A, Cove J H. 2003. Antibiotic-resistant acne: lessons from Europe. The British journal of dermatology 148:467-478.
27. Jackson A P, Thomas G H, Parkhill J, Thomson N R. 2009. Evolutionary diversification of an ancient gene family (rhs) through C-terminal displacement. BMC Genomics 10:584.
28. Horvath P, Barrangou R. 2010. CRISPR/Cas, the immune system of bacteria and archaea. Science 327:167-170.
29. Harris S R, Feil E J, Holden M T, Quail M A, Nickerson E K, Chantratita N, Gardete S, Tavares A, Day N, Lindsay J A, Edgeworth J D, de Lencastre H, Parkhill J, Peacock S J, Bentley S D. 2010. Evolution of MRSA during hospital transmission and intercontinental spread. Science 327:469-474.
30. Croucher N J, Harris S R, Fraser C, Quail M A, Burton J, van der Linden M, McGee L, von Gottberg A, Song J H, Ko K S, Pichon B, Baker S, Parry C M, Lambertsen L M, Shahinas D, Pillai D R, Mitchell T J, Dougan G, Tomasz A, Klugman K P, Parkhill J, Hanage W P, Bentley S D. 2011. Rapid pneumococcal evolution in response to clinical interventions. Science 331:430-434.
31. Chin C S, Sorenson J, Harris J B, Robins W P, Charles R C, Jean-Charles R R, Bullard J, Webster D R, Kasarskis A, Peluso P, Paxinos E E, Yamaichi Y, Calderwood S B, Mekalanos J J, Schadt E E, Waldor M K. 2011. The origin of the Haitian cholera outbreak strain. The New England journal of medicine 364:33-42.
32. Gordon D, Abajian C, Green P. 1998. Consed: a graphical tool for sequence finishing. Genome Res 8:195-202.

33. Zerbino D R, Birney E. 2008. Velvet: algorithms for de novo short read assembly using de Bruijn graphs. Genome Res 18:821-829.
34. Borodovsky M, McIninch J. 1993. Recognition of genes in DNA sequence with ambiguities. Biosystems 30:161-171.
35. Salzberg S L, Delcher A L, Kasif S, White O. 1998. Microbial gene identification using interpolated Markov models. Nucleic Acids Res 26:544-548.
36. Kurtz S, Phillippy A, Delcher A L, Smoot M, Shumway M, Antonescu C, Salzberg S L. 2004. Versatile and open software for comparing large genomes. Genome Biol 5:R12.
37. Tamura K, Peterson D, Peterson N, Stecher G, Nei M, Kumar S. 2011. MEGA5: molecular evolutionary genetics analysis using maximum likelihood, evolutionary distance, and maximum parsimony methods. Mol Biol Evol 28:2731-2739.
38. Grissa I, Vergnaud G, Pourcel C. 2007. CRISPRFinder: a web tool to identify clustered regularly interspaced short palindromic repeats. Nucleic Acids Res 35:W52-57.
39. Altschul S F, Gish W, Miller W, Myers E W, Lipman D J. 1990. Basic local alignment search tool. J Mol Biol 215:403-410.
40. de Hoon M J, Imoto S, Nolan J, Miyano S. 2004. Open source clustering software. Bioinformatics 20:1453-1454.
41. Saldanha A J. 2004. Java Treeview—extensible visualization of microarray data. Bioinformatics 20:3246-3248.

Example 3—Microbial DNA Extraction from Skin Samples Skin Microcomedone Sampling Skin microcomedone (white head or black head) samples were taken from the skin of the subjects using a specialized adhesive tape. The skin was moistened with water before the adhesive tape was put on. The tape was left on the skin for 15-20 minutes until it became dry. Clean gloves were used for each sampling. After being taken off from the skin, the tape was placed into a 50 mL sterile tube. This can be applied to many skin sites, such as the nose, forehead, chin, and back.

Bacterial DNA Extraction

Microcomedones were individually picked or scraped off from the adhesive tape using sterile forceps and placed in a 2 mL sterile microcentrifuge tube filled with Buffer ATL (Qiagen) and 0.1 mm diameter glass beads (BioSpec Products, Inc., Bartlesville, Okla.). Cells were lysed using a beadbeater for 3 minutes at 4,800 rpm at room temperature. After centrifugation at 14,000 rpm for 5 minutes, the supernatant was retrieved and used for genomic DNA extraction using QIAamp DNA Micro Kit (Qiagen). The manufacturer protocol for extracting DNA from chewing gum was used. Concentration of the genomic DNA was determined by a spectrometer.

Example 4—Microbiome Type Detection

Detailed Protocol for Accurate Detection of the Skin Microbiome Type Based on 16S rDNA
PCR Amplification, Cloning, and Sequencing 16S rDNA was amplified using primers 8F (5'-AGAGTTTGATYMTGGCTCAG-3') and 151OR (5'-TACGGYTACCTTGTTACGACTT-3'). Thermocycling conditions were as following: initial denaturation step of 5 minutes at 94° C., 30 cycles of denaturation at 94° C. for 45 seconds, annealing at 52° C. for 30 seconds and elongation at 72° C. for 90 seconds, and a final elongation step at 72° C. for 20 minutes. PCR products were purified using column-based method. Subsequently, the 16S rDNA amplicons were cloned into pCR 2.1-TOPO vector (Invitrogen). One-Shot TOP-10 Chemically Competent E. coli cells (Invitrogen) were transformed with the vectors and plated on selective media. Individual positive colonies were picked and inoculated into selective LB liquid medium. After 14 hours of incubation, the plasmids were extracted and purified, either using column-based plasmid extraction kit or traditional methods. The clones were sequenced bidirectionally using Sanger sequencing method. The microbiome type of each individual was determined based on the 16S rDNA sequence data of the top 10 major ribotypes. See FIG. 5 and SEC) ID NOs 1-10.

Detailed Protocols for Fast Detection of the Skin Microbiome Type Based on PCR and qPCR By sequencing and annotating 69 novel P. acnes genomes and by comparing a total of 82 P. acnes genomes, several genomic loci which are unique to acne associated P. acnes strains were identified, i.e., Loci 1-4. See FIG. 8. The genomic sequences of Loci 1, 2, 3, and 4 from all sequences P. acnes strains and their sequence similarities, which range from 95% to 100%, are listed as SEQ ID NOs 15-18, respectively.

Detection Method 1

Figure 23:
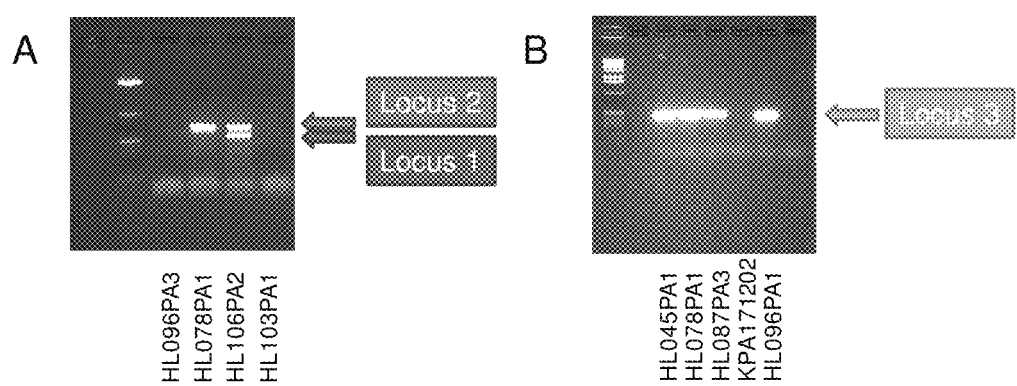
FIG. 23 reflects fast detection of acne associated *P. acnes* strains using multiplex PCR targeting loci 1, 2, and 3.

To rapidly detect the presence or absence of RT4 and RT5 strains in patients, multiplex PCR targeting Loci 1, 2, and 3 was designed and performed on genomic DNA extracted from P. acnes strains and skin samples. FIG. 23 shows that Loci 1, 2, and 3 were amplified from various P. acnes strains as predicted based on the genome data.

The PCR primer sequences are shown in Table 6:

TABLE 6

Primers specific for loci 1, 2, 3 and Pak (housekeeping gene)

| Target locus | Forward primer | Reverse primer |
|---|---|---|
| Locus 1 | GGTATCCACCGAGATGGAAG (SEQ ID NO: 11) | GTGGTCCCAGGTGACATTCT (SEQ ID NO: 12) |
| Locus 2 | CGACATCGACGTTTCATCTG (SEQ ID NO: 13) | GTGTTCTCCTCGTGCTGGTT (SEQ ID NO: 14) |
| Locus 3 | GATAATCCGTTCGACAAGCTG (SEQ ID NO: 15) | ACCCACCACGATGATGTTT (SEQ ID NO: 16) |
| Pak | CGACGCCTCCAATAACTTCC | GTCGGCCTCCTCAGCATC |

Additional primers targeting these loci can be designed based on the genome sequences of loci 1-4 (SEQ ID NOs 15-18, respectively). Each 20 µL reaction contains 12.7 µL molecular grade H2O, 2 µL 10× High Fidelity Buffer, 0.6 µL 50 mM MgSO4, 0.4 µL 10 nM dNTP, 0.8 µL of each primer (final primer concentrations is 400 nM), 0.1 µL Platinum Taq DNA Polymerase High Fidelity (All reagents from Invitrogen) and 1 µL gDNA template (approx. 40 ng gDNA). The thermocycling conditions are as following: initial denaturation step of 10 minutes at 95° C.; 35 cycles with each consisting of 45 seconds at 95° C., 30 seconds at 65° C. and 45 seconds at 72° C.; and final elongation step of 10 minutes at 72° C.

To quantitatively measure the abundance of acne associated *P. acnes* strains in skin samples, quantitative PCR (qPCR) targeting Loci 1, 2, and 3 were performed on genomic DNA extracted from *P. acnes* strains. See FIG. 12. LightCyler 480 High Resolution Melting Master kit was used (Roche Diagnostics GmbH, Mannheim, Germany). Each 10 µL reaction contains 5 µL of Master Mix (2× concentrate), 1 µL of 25 mM MgCl2, 0.5 µL of 4 µM forward and reverse primers, 1 µL to 3.5 µL of DNA template (approximately 2.5 ng DNA), and molecular grade H2O, up to the volume. The thermocycling conditions were as following: initial activation step of 10 minutes at 95° C.; 40 amplification cycles with each consisting of 10 seconds at 95° C., 15 seconds at 65° C. during first cycle, but with a stepwise 0.5° C. decrease for each succeeding cycle and 30 seconds at 72° C.; and finally, a melting curve step, starting at 65° C. and ending at 99° C., with ramp rate of 0.02° C./s and acquisition rate of 25 per ° C.

The protocol was tested using mock samples, where different strains of *P. acnes* were mixed in different proportions to mimic the strain population distributions in real samples. See Table 7.

TABLE 7

Mock samples mimicking the microbiome types observed in human skin samples

| Mock sample | Microbiome type | Dominant isolate | Percentage of dominant isolate | Abundance of Locus 1 | Abundance of Locus 2 |
|---|---|---|---|---|---|
| 1A | I | HL036PA3 | 80 | 7.5% | 7.5% |
| 1B | I | HL078PA1 | 80 | 7.5% | 87.5% |
| 1C | I | HL106PA2 | 80 | 87.5% | 87.5% |
| 2 | II | HL103PA1 | 80 | 8.0% | 10.0% |
| 3 | III | HL087PA3 | 80 | 8.0% | 10.0% |
| 4 | IV | HL038PA1 | 70 | 79.0% | 82.0% |
| 5A | V | HL072PA2 | 80 | 6.7% | 8.9% |
| 5B | V | HL096PA1 | 80 | 86.7% | 88.9% |
| 6 | minor | HL110PA4 | 70 | 12.0% | 15.0% |
| 8A | minor | HL086PA1 | 70 | 80.0% | 83.3% |
| 8B | minor | HL092PA1 | 70 | 10.0% | 13.3% |

Figure 24:
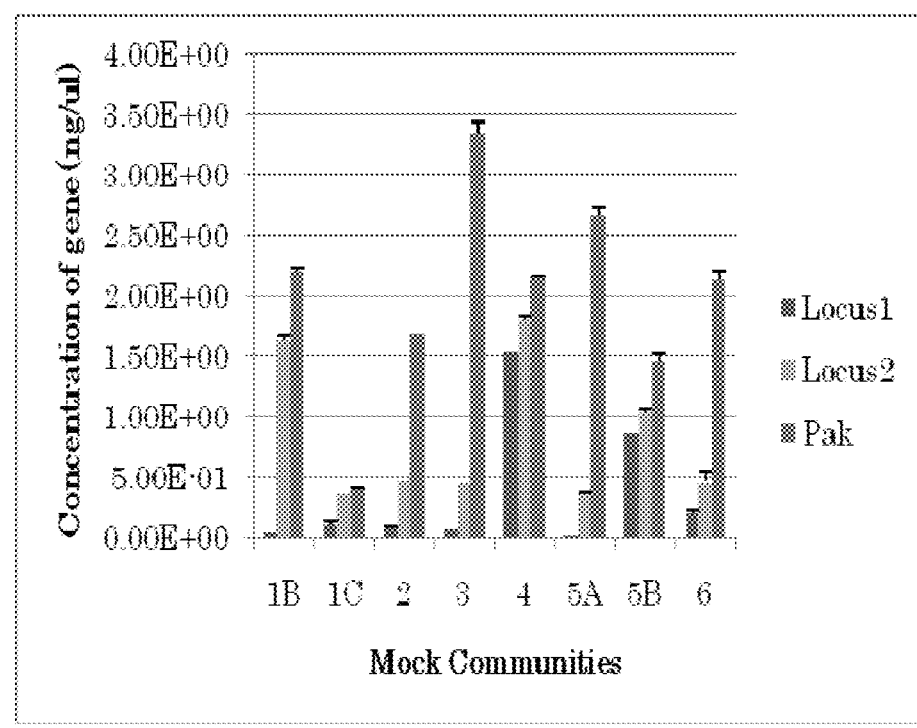
FIG. 24 shows the relative abundances of Locus 1 and Locus 2 as compared to the housekeeping gene Pak.

The concentration of each locus was quantified from standards derived from Locus 1, Locus 2, and Pak PCR amplicons. The copy number of each gene was quantified from genomic DNA standards that were derived from TadA (in Locus 3) and Pak amplicons using conventional PCR. See FIG. 24.

Detection Method 2

*P. acnes* TaqMan qPCR Assay

Primer and Probe Design

Primers and probes for detecting Loci 1, 2, 3, and 4 in *P. acnes* strains and clinical samples were designed as listed in Table 8:

TABLE 8

Primer and probe sequences used for identification of *P. acnes* loci

| Targeted region | Primer/Probe | Primer/Probe name | Sequence (5'-3') | Amplicon size (bp) |
|---|---|---|---|---|
| Locus1 | forward primer | Locus1_F | GAAGAATCCCGCTCCATTTCC (SEQ ID NO: 17) | 107 |
| | reverse primer | Locus1_R | CCTTTCTTGTAGCCGAGCAG (SEQ ID NO: 18) | |
| | probe | Locus1_Probe | 56-FAM/ATTGTCACC/ZEN/TGGGACCACCGTAAAC/3IABkFQ (SEQ ID NO: 19) | |
| Locus2 | forward primer | Locus2_F | CGTGATCCTGATCGACTGTG (SEQ ID NO: 20) | 103 |
| | reverse primer | Locus2_R | GCTCCACAACTTCGAGTGC (SEQ ID NO: 21) | |
| | probe | Locus2_Probe | CAGGCCGTTGATCGTGAGCTGA (SEQ ID NO: 22) | |
| Locus3 | forward primer | Locus3_F | TGCTGATAATCCGTTCGACA (SEQ ID NO: 23) | 104 |
| | reverse primer | Locus3_R | ACGACGTCGAAAACAACTCC (SEQ ID NO: 24) | |
| | probe | Locus3_Probe | 5TET/CTCTACCGA/ZEN/AGCTCTTGCCGCAT/3IABkFQ (SEQ ID NO: 25) | |
| Locus4 | forward primer | Locus4_F | ATCGCCGTCGACAGGTAGT (SEQ ID NO: 26) | 103 |
| | reverse primer | Locus4_R | CCGAGATTCTGCGCCTAGT (SEQ ID NO: 27) | |
| | probe | Locus4_Probe | CGGTGCCCTTGCTGAGGTACA (SEQ ID NO: 28) | |

TABLE 8-continued

Primer and probe sequences used for identification of P. acnes loci

| Targeted region | Primer/ Probe | Primer/ Probe name | Sequence (5'-3') | Amplicon size (bp) |
|---|---|---|---|---|
| Pak | forward primer | Pak_F | GCAACCCGACATCCTCATTA | 101 |
|  | reverse primer | Pak_R | AGTCGAAGAAGTCGCTCAGG |  |
|  | probe | Pak_Probe | VIC/CGTTCTACAGCCACCACGACGG/TAMRA |  |

A triplex Taqman qPCR was designed and tested using *Propionibacterium* specific primers to target Locus 1, Locus 3, and an internal control, Pak, present in all *P. acnes*.

Locus 1, Locus 3, and Pak Amplification

Benchtop amplification was carried out to assess specificity of designed primers and to determine optimum cycling conditions prior to multiplexing. Amplification was carried out using a BioRad C1000 thermal cycler. Singleplex PCR reactions contained 0.2 µM target specific primers, 10× Platinum Taq buffer (Invitrogen), 1.0 mM MgCl2, 0.2 mM each dNPT, 0.5 U/µl Platinum Taq polymerase, 1 µl DNA template and made up to a final volume of 10 µl. Cycling was as follows: initial denaturation 94° C. for 5 minutes, followed by 30 cycles of denaturation at 94° C. for 30 seconds, annealing at 60° C. for 30 seconds and extension at 72° C. for 30 seconds, and one final extension cycle at 72° C. for 5 minutes. Amplification products were analysed electrophoretically on a 1% agarose/TBE gel to check for correct amplification of target and cross-species reactivity with primer targets.

Taqman Triplex PCR

Triplex qPCR was carried out using an Applied Biosystems 7900HT instrument. 1-2 µl of sample DNA were added to mastermix containing X2 QuantiTect Multiplex PCR Master Mix (Qiagen), 0.2 µM primers; Locus1_F, Locus1_R, Pak_F, Pak_R; 0.2 µM probes; Locus1_Probe and Pak_Probe, and 0.1 µM primers Locus3_F and Locus3_R, and 0.1 µM Locus3_Probe. The reaction mix was made up to a final volume of 20 µl with sterile PCR grade water. The PCR program consisted of one cycle at 50° C. for 2 minutes, followed by one cycle at 95° C. for 15 minutes to allow for activation of the multiplex mastermix, then 45 cycles of 94° C. for 60 seconds and 57° C. for 90 seconds. Each run contained calibrators of extracted *P. acnes* DNA from culture, as well as no-template controls (NTC) and water controls. qPCR was run with a passive reference, ROX, supplied in the Quantitect Multiplex PCR mastermix. Data were analysed using the SDS v2.4 software.

Assay Calibration, Sensitivity, and Specificity

Calibrations curves for *P. acnes* targets Locus 1 and Pak were constructed by plotting mean Ct values for a series of log dilutions of quantified genomic DNA standards extracted from *P. acnes* from pure culture. Genome equivalents were estimated. Five replicates of *P. acnes* calibrators were used to calculate mean Ct values and standard deviations. These data were used to determine sensitivity of the assay and the limits of detection (LOD). Calibration plots were used to determine the number of *P. acnes* genomes in clinical samples, with one copy of Locus1 and Pak targets per genome. DNA concentration and copy number were determined and serial ten-fold dilutions of the purified product were used as standards for construction of the Locus3 calibration plot. Strains that display possible combinations of the presence and absence of Locus1 and Locus 3 were used for Locus1 and Pak calibration: HL038PA1 (Locus1+, Locus3+), HL083PA1 (Locus1+, Locus3−), HL078PA1 (Locus1−, Locus3+) and HL063PA1 (Locus1−, Locus3−). The assay was validated using sequenced *P. acnes* strains from pure culture with known loci before being applied to clinical samples. The specificity of the assay for each target was tested using other bacterial species including skin commensals and other Propionibacteria.

Assay Validation

A total of 24 sequenced *P. acnes* strains (HL063PA1, HL078PA1, HL083PA1, HL038PA1, HL037PA1, HL082PA1, HL020PA1, HL001PA1, HL046PA2, HL043PA1, HL086PA1, HL110PA3, HL110PA4, HL007PA1, HL087PA3, HL027PA1, HL056PA1, HL067PA1, HL074PA1, HL045PA1, HL053PA1, HL005PA1, HL072PA1, HL043PA2) including possible combinations with and without Locus 1 and Locus 3 were used to validate the triplex qPCR assays. The qPCR triplex assay successfully identified Locus 1 and Locus 3 in strains previously shown by whole genome sequencing to harbor these loci.

Application to Clinical Samples

Genomic DNA extracted from two clinical samples, #1 and #2, were analyzed using the Taqman qPCR triplex assay. Amplification plots revealed the presence of *P. acnes* (Pak) in both samples (FIG. 6). Locus1 and Locus 3 targets were also detected in both samples with a much larger percentage of *P. acnes* Locus1 positive and Locus3 positive strains present in 1 µl of sample #1 compared to sample #2.

Example 5—Acne Vaccine

Strains with 16S rDNA ribotypes (RTs) 4, 5, 7, 8, 9, and 10 were identified as highly associated with acne. Vaccines can be raised against these strains. See T. Nakatsuji et al., 128(10) J. Invest. Dermatol. 2451-2457 (October 2008).

Example 6—Probiotic Development Utilizing the Strains Associated with Healthy Skin in Topical Creams, Solutions, and the Like for Cosmetic and Other Products RT6 is mostly found in healthy skin. These strains can be used as probiotics in topical products for acne prevention and treatment. Four RT6 strains, including HL110PA3, HL110PA4, HL042PA3, and HL202PA1, were isolated and sequenced.

In addition, bacterial culture supernatant and/or cell lysate, including bacterial metabolites, can be used in creams, solutions, and other cosmetic products to prevent the growth of strains associated with acne. Sequences sharing at least 95% homology with SEQ ID NOs 51-54 may be used for the development of probiotics and the like.

Example 7—Drug Development Targeting Specific Strains that are Associated with Acne Identification of the Core and Non-Core Regions of *P. acnes*

The "core" genome regions of *P. acnes* were defined as genome sequences that are present in all of the 82 genomes, while the "non-core" regions were defined as genome sequences that are NOT present in all the genomes. See S. Tomida et Pan-genome and Comparative Genome Analyses of *Propionibacterium acnes* Reveal Its Genomic Diversity in the Healthy and Diseased Human Skin Microbiome (in press); see also Example 2. Non-core regions specific to strains of RTs 4 and 5, e.g., loci 1, 2, and 3, were identified, as mentioned previously. Non-core regions specific to strains of RT8 (noted as Locus 4) were also identified as well as several other strains such as HL078PA1, HL030PA2, HL063PA2, P.acn17, HL097PA1, and PRP38. See FIG. 20. The genomic sequence of Locus 4 is set forth as SEQ ID NO:18. The genes in loci 1-4 below (Tables 9, 10, and 11) that are mostly unique to acne associated strains RT4, RT5, and RT8 are listed below. Non-core sequences are also set forth. The genes encoded in these loci are drug targets.

TABLE 9

List of genes encoded in loci 1 and 2, specific to RT4 and 5

| Locus in FIG. 3a | ID | Description |
| --- | --- | --- |
| Locus 1 | GM131 | ABC transporter ATP-binding protein |
| Locus 1 | GM132/GM133*[2] | Site-specific recombinase |
| Locus 1 | GM134 | Site-specific recombinase |
| Locus 1 | GM135 | Hypothetical protein |
| Locus 1 | GM136 | Hypothetical protein |
| Locus 1 | GM137 | N-acetylmuramoyl-L-alanine amidase |
| Locus 2 | GM171 | Hypothetical protein |
| Locus 2 | GM172 | Hypothetical protein |
| Locus 2 | GM173 | Single-strand binding family protein |
| Locus 2 | GM174 | CobQ/CobB/MinD/ParA nucleotide binding domain protein |
| Locus 2 | GM175 | Hypothetical protein |
| Locus 2 | GM176 | Hypothetical protein |
| Locus 2 | GM177 | Hypothetical protein |
| Locus 2 | GM178 | Hypothetical protein |
| Locus 2 | GM179 | Hypothetical protein |
| Locus 2 | GM180 | Hypothetical protein |
| Locus 2 | GM181 | CAAX amino protease family protein |
| Locus 2 | GM182 | Hypothetical protein |
| Locus 2 | GM183 | YcaO-like protein |
| Locus 2 | GM184 | Hypothetical protein |
| Locus 2 | GM185 | SagB-type dehydrogenase domain protein |
| Locus 2 | GM186 | Hypothetical protein |
| Locus 2 | GM187 | ABC transporter, ATP-binding protein |
| Locus 2 | GM188 | ABC-2 type transporter |
| Locus 2 | GM189 | Hypothetical protein |
| Locus 2 | GM196 | Hypothetical protein |

TABLE 10

List of genes encoded in Locus 3, a linear plasmid and specific to RT4 and 5

| Locus | ID | Description |
| --- | --- | --- |
| Locus 3 | PAGK_2319 | hypothetical protein |
| Locus 3 | PAGK_2320 | hypothetical protein |
| Locus 3 | PAGK_2321 | hypothetical protein |
| Locus 3 | PAGK_2322 | plasmid stabilization system protein |

TABLE 10-continued

List of genes encoded in Locus 3, a linear plasmid and specific to RT4 and 5

| Locus | ID | Description |
| --- | --- | --- |
| Locus 3 | PAGK_2323 | hypothetical protein |
| Locus 3 | PAGK_2324 | hypothetical protein |
| Locus 3 | PAGK_2325 | hypothetical protein |
| Locus 3 | PAGK_2326 | CobQ/CobB/MinD/ParA nucleotide binding domain |
| Locus 3 | PAGK_2327 | hypothetical protein |
| Locus 3 | PAGK_2328 | hypothetical protein |
| Locus 3 | PAGK_2329 | hypothetical protein |
| Locus 3 | PAGK_2330 | hypothetical protein |
| Locus 3 | PAGK_2331 | hypothetical protein (similar to PPA1279) |
| Locus 3 | PAGK_2332 | plasmid partition protein ParA |
| Locus 3 | PAGK_2333 | hypothetical protein |
| Locus 3 | PAGK_2334 | hypothetical protein |
| Locus 3 | PAGK_2335 | hypothetical protein |
| Locus 3 | PAGK_2336 | putatove ribbon-helix-helix protein, copG family |
| Locus 3 | PAGK_2337 | putative ribonuclease E |
| Locus 3 | PAGK_2338 | hypothetical protein (similar to PPA1294) |
| Locus 3 | PAGK_2339 | hypothetical protein (similar to PPA1295) |
| Locus 3 | PAGK_2340 | putative permease |
| Locus 3 | PAGK_2341 | hypothetical protein (similar to PPA1297) |
| Locus 3 | PAGK_2342 | hypothetical protein (similar to PPA1298) |
| Locus 3 | PAGK_2343 | hypothetical protein (similar to PPA1299) |
| Locus 3 | PAGK_2344 | hypothetical protein (similar to CLOLEP_00122) |
| Locus 3 | PAGK_2345 | hypothetical protein (similar to CLOLEP_00123) |
| Locus 3 | PAGK_2346 | hypothetical protein (similar to CLOLEP_00124) |
| Locus 3 | PAGK_2347 | hypothetical protein (similar to CLOLEP_00125) |
| Locus 3 | PAGK_2348 | hypothetical protein (similar to CLOLEP_00126) |
| Locus 3 | PAGK_2349 | hypothetical protein (similar to CLOLEP_00127) |
| Locus 3 | PAGK_2350 | hypothetical protein |
| Locus 3 | PAGK_2351 | hypothetical protein (similar to CLOLEP_00129) |
| Locus 3 | PAGK_2352 | hypothetical protein (similar to CLOLEP_00130) |
| Locus 3 | PAGK_2353 | hypothetical protein (similar to CLOLEP_00131) |
| Locus 3 | PAGK_2354 | hypothetical protein (similar to CLOLEP_00132) |
| Locus 3 | PAGK_2355 | hypothetical protein (similar to CLOLEP_00134) |
| Locus 3 | PAGK_2356 | hypothetical protein (similar to CLOLEP_00135) |
| Locus 3 | PAGK_2357 | hypothetical protein (similar to CLOLEP_00141) |
| Locus 3 | PAGK_2358 | hypothetical protein (similar to CLOLEP_00142) |
| Locus 3 | PAGK_2359 | hypothetical protein (similar to CLOLEP_00143) |
| Locus 3 | PAGK_2360 | hypothetical protein (similar to CLOLEP_00144, RcpC) |
| Locus 3 | PAGK_2361 | hypothetical protein (similar to CLOLEP_00145, TadZ) |
| Locus 3 | PAGK_2362 | hypothetical protein (similar to CLOLEP_00146, TadA) |
| Locus 3 | PAGK_2363 | hypothetical protein (similar to CLOLEP_00147, TadB) |
| Locus 3 | PAGK_2364 | hypothetical protein (similar to CLOLEP_00148, TadC) |
| Locus 3 | PAGK_2365 | hypothetical protein (similar to CLOLEP_00149, Flp-1) |
| Locus 3 | PAGK_2366 | hypothetical protein (similar to CLOLEP_00151, TadE) |
| Locus 3 | PAGK_2367 | hypothetical protein (similar to CLOLEP_00152, TadE) |
| Locus 3 | PAGK_2368 | hypothetical protein (similar to CLOLEP_00153, TadE) |
| Locus 3 | PAGK_2369 | hypothetical protein (similar to CLOLEP_00154) |

TABLE 10-continued

List of genes encoded in Locus 3,
a linear plasmid and specific to RT4 and 5

| Locus | ID | Description |
|---|---|---|
| Locus 3 | PAGK_2370 | hypothetical protein (similar to CLOLEP_00157) |
| Locus 3 | PAGK_2371 | hypothetical protein (similar to CLOLEP_00158) |
| Locus 3 | PAGK_2372 | hypothetical protein (similar to CLOLEP_00159) |
| Locus 3 | PAGK_2373 | hypothetical protein (similar to CLOLEP_00160) |
| Locus 3 | PAGK_2374 | hypothetical protein |
| Locus 3 | PAGK_2375 | hypothetical protein (similar to CLOLEP_00162) |
| Locus 3 | PAGK_2376 | hypothetical protein (similar to CLOLEP_00163) |
| Locus 3 | PAGK_2377 | hypothetical protein (similar to CLOLEP_00164) |
| Locus 3 | PAGK_2378 | hypothetical protein (similar to CLOLEP_00166) |
| Locus 3 | PAGK_2379 | repA |
| Locus 3 | PAGK_2380 | CobQ/CobB/MinD/ParA nucleotide binding domain |
| Locus 3 | PAGK_2381 | hypothetical protein |
| Locus 3 | PAGK_2382 | hypothetical protein |
| Locus 3 | PAGK_2383 | Yag1E |
| Locus 3 | PAGK_2384 | hypothetical protein |
| Locus 3 | PAGK_2385 | hypothetical protein |
| Locus 3 | PAGK_2386 | hypothetical protein |
| Locus 3 | PAGK_2387 | hypothetical protein |
| Locus 3 | PAGK_2388 | hypothetical protein |
| Locus 3 | PAGK_2389 | hypothetical protein |
| Locus 3 | PAGK_2390 | hypothetical protein |
| Locus 3 | PAGK_2391 | hypothetical protein |
| Locus 3 | PAGK_2392 | ResA |

TABLE 11

List of genes encoded in Locus 4, RT8 specific region

| Locus | ID | Description |
|---|---|---|
| Locus 4 | HMPREF9576_00292 | tRNA adenylyltransferase |
| Locus 4 | HMPREF9576_00293 | conserved hypothetical protein |
| Locus 4 | HMPREF9576_00294 | conserved domain protein |
| Locus 4 | HMPREF9576_00295 | response regulator receiver domain protein |
| Locus 4 | HMPREF9576_00296 | histidine kinase |
| Locus 4 | HMPREF9576_00297 | hypothetical protein |
| Locus 4 | HMPREF9576_00298 | hypothetical protein |
| Locus 4 | HMPREF9576_00299 | hypothetical protein |
| Locus 4 | HMPREF9576_00300 | hypothetical protein |
| Locus 4 | HMPREF9576_00301 | hypothetical protein |
| Locus 4 | HMPREF9576_00302 | drug resistance MFS transporter, drug:H+ antiporter-2 (14 Spanner) (DH42) family protein |
| Locus 4 | HMPREF9576_00303 | hypothetical protein |
| Locus 4 | HMPREF9576_00304 | conserved domain protein |
| Locus 4 | HMPREF9576_00305 | beta-ketoacyl synthase, N-terminal domain protein |
| Locus 4 | HMPREF9576_00306 | hypothetical protein |
| Locus 4 | HMPREF9576_00307 | acetyltransferase, GNAT family |
| Locus 4 | HMPREF9576_00308 | putative (3R)-hydroxymyristoyl-ACP dehydratase |
| Locus 4 | HMPREF9576_00309 | putative acyl carrier protein |
| Locus 4 | HMPREF9576_00310 | putative 3-ketoacyl-(acyl-carrier-protein) reductase |
| Locus 4 | HMPREF9576_00311 | ornithine cyclodeaminase/mu-crystallin family protein |
| Locus 4 | HMPREF9576_00312 | pyridoxal-phosphate dependent enzyme |
| Locus 4 | HMPREF9576_00313 | lantibiotic dehydratase, C-terminus |
| Locus 4 | HMPREF9576_00314 | aminotransferase, class VII |

TABLE 11-continued

List of genes encoded in Locus 4, RT8 specific region

| Locus | ID | Description |
|---|---|---|
| Locus 4 | HMPREF9576_00315 | acyl carrier domain protein |
| Locus 4 | HMPREF9576_00316 | AMP-binding enzyme |
| Locus 4 | HMPREF9576_00317 | malonyl CoA-acyl carrier protein transacylase family protein |
| Locus 4 | HMPREF9576_00318 | ABC-2 type transporter |
| Locus 4 | HMPREF9576_00319 | ABC transporter, ATP-binding protein |
| Locus 4 | HMPREF9576_00320 | hypothetical protein |

Example 8—Targeted Phage Therapy

Bacteriophages play an important role in regulating the composition and dynamics of microbial communities, including the human skin microbiota. Bacteriophages of *Propionibacterium acnes*, a major skin commensal, were previously isolated and used as a typing system to distinguish different serotypes of *P. acnes*. However, molecular characterization of these phages had been lacking. Recent efforts in genome sequencing have improved our understanding of *P. acnes* phages and their interactions with bacterial hosts.

Bacteriophages are the most abundant organisms on earth (Mc Grath & van Sinderen, 2007) and are believed to outnumber bacteria by 10:1 in many diverse ecosystems (Rohwer, 2003). As important components of microbial communities, bacteriophages are a reservoir of diversity-generating elements (Rohwer & Thurber, 2009) and regulate both the abundances (Suttle, Chan, & Cottrell, 1990) and diversity of microbial hosts by predation (Rodriguez-Valera et al., 2009). The human skin is inhabited by hundreds of microbial species, including bacteria, fungi, and viruses (Grice & Segre, 2011). The homeostasis of this ecosystem is important to its function as a barrier against the invasion and colonization of pathogens on the skin. However, much remains to be learned about the nature and driving forces of the dynamics among the microorganisms in the skin microbial community. In particular, the relative abundances and interactions between bacteriophages and their bacterial hosts on the skin remained to be elucidated.

The microbial community in the pilosebaceous unit of the skin is dominated by *Propionibacterium acnes*, which accounts for approximately 90% of the microbiota ("(Nature Precedings Paper)," n.d.). *P. acnes* has been suggested as a pathogenic factor in the development of acne vulgaris (Bojar & Holland, 2004; Leyden, 2001), one of the most common human skin diseases. Above-detailed studies classified *P. acnes* strains into ribotypes (RT) based on their 16S ribosomal RNA (rRNA) sequences, and demonstrated that *P. acnes* strain population structure in pilosebaceous units differs between healthy skin and acne affected skin.

*P. acnes* bacteriophages exist on the human skin. In 1968, Zierdt et al. (Zierdt, Webster, & Rude, 1968) isolated such a phage, named phage 174, from spontaneous plaques of a *P. acnes* isolate (at the time known as *Corynebacterium acnes*). Phage 174 was able to lyse nearly all *P. acnes* strains tested in the study [10]. Subsequently, more *P. acnes* phages were isolated which exhibited varied life cycles that range from lytic to temperate [11, 12]. However, in the last decades, the study of *P. acnes* bacteriophages had been limited to the development of phage typing systems to distinguish the different serotypes of *P. acnes* [13, 14]_EN-REF_4, and extensive molecular characterization of the phages has been lacking.

Recent genomic sequencing of P. acnes bacteriophages (Farrar et al., 2007; Lood & Collin, 2011; Marinelli et al., 2012) have provided new insight into P. acnes phage diversity. P. acnes phages are similar to mycobacteriophages both morphologically and genetically, but have a much smaller genome. Currently 14 phage genome sequences are available. Sequencing additional phage isolates is needed to further characterize the diversity. Despite these recent sequencing efforts, the genome-level diversity of P. acnes phages in the human skin microbiome and their interactions with P. acnes and other Propionibacteria remain to be elucidated. P. acnes phages have diverse host specificities among different lineages of P. acnes strains [14]. Phage host specificity is important in determining how these phages regulate the composition and dynamics of P. acnes populations in the community. On the other hand, certain P. acnes strains may also influence phage populations through their anti-viral mechanisms, such as the bacterial immune system based on the transcription of clustered, regularly-interspaced short, palindromic repeat (CRISPR) sequence arrays. The CRISPR arrays contain oligonucleotide 'spacers' derived from phage DNA or plasmid DNA. In a manner analogous to RNA interference, the transcribed, single-stranded CRISPR RNA elements interact with CRISPR-associated (Cas) proteins to direct the degradation of DNA targets containing complementary 'protospacer' sequences from foreign DNA [16]. While characterizing the genome diversity of P. acnes, Applicants discovered that P. acnes strains of RT2 and RT6 harbor CRISPR arrays. The CRISPR mechanism may play a role in defending against phage or plasmid invasion.

To better understand the interactions between bacteria and bacteriophages in the human skin microbiome and their contributions to skin health and disease, the diversity and host specificity of P. acnes phages isolated from acne patients and healthy individuals was investigated. The genomes of 15 phage isolates were investigated and screened against a panel of 69 sequenced Propionibacteria strains to determine their host range and specificity.

Phage Isolation and General Genome Features

To characterize the genetic diversity and the abundance of P. acnes phages in the skin microbiome, 203 skin samples of pilosebaceous units from 179 individuals were collected, including 109 samples from normal individuals and 94 from acne patients. All of the samples were cultured for P. acnes under anaerobic conditions. Phage plaques in 49 samples were observed: 35 from normal individuals and 14 from acne patients. P. acnes phages were found more frequently in samples from normal individuals than from acne patients with statistical significance (p=0.005, Fisher's exact test). Among the 93 phage isolates that were obtained from these samples, five phages from acne patients and ten from normal individuals were selected for whole genome sequencing using 454 or Illumina platforms (Table 12).

TABLE 12

Phage Genome Information and Sequencing Statistics

| Phage Name | Genome Length (bp) | GC % | Total Input Reads | Total Input Bases | Coverage | Annotated ORFs | Presence of 11-nt Overhand |
|---|---|---|---|---|---|---|---|
| PHL111M01 | 29,140 | 54.33 | 5,453 | 2,865,116 | 98× | 46 | yes |
| PHL060L00 | 29,514 | 64.05 | 10,000 | 12,015,904 | 407× | 47 | yes |
| PHL112N00 | 29,266 | 54.45 | 10,000 | 12,270,460 | 419× | 47 | yes |
| PHL113M01 | 29,200 | 54.10 | 4,228 | 2,237,790 | 77× | 45 | yes |
| PHL114L00 | 29,464 | 54.21 | 10,000 | 12,270,600 | 416× | 47 | yes |
| PHL010M04 | 29,511 | 53.99 | 3,185 | 1,686,535 | 57× | 46 | not verified |
| PHL066M04 | 29,512 | 53.99 | 4,478 | 2,364,379 | 80× | 46 | yes |
| PHL073M02 | 29,503 | 53.99 | 4,700 | 2,529,669 | 86× | 46 | not verified |
| PHL071N05 | 29,467 | 53.92 | 6,143 | 3,059,098 | 104× | 46 | not verified |
| PHL057M10 | 29,377 | 54.26 | 4,456 | 2,313,471 | 79× | 46 | yes |
| PHL115M02 | 29,453 | 63.82 | 5,914 | 4,687,391 | 169× | 46 | yes |
| PHL085M01 | 29,451 | 63.82 | 10,000 | 12,552,610 | 426× | 46 | yes |
| PHL037M02 | 29,443 | 62.78 | 5,895 | 3,093,818 | 106× | 46 | yes |
| PHL085N00* | 29,454 | 53.83 | 20,000 | 3,904,239 | 133 | 45 | yes |
| PHL082M00* | 29,491 | 54.38 | 20,000 | 3,289,741 | 112 | 44 | yes |
| Average | 29,383 | 54.05 | 6,729 | 5,688,219 | 193.37 | 46 | |

Figure 29:
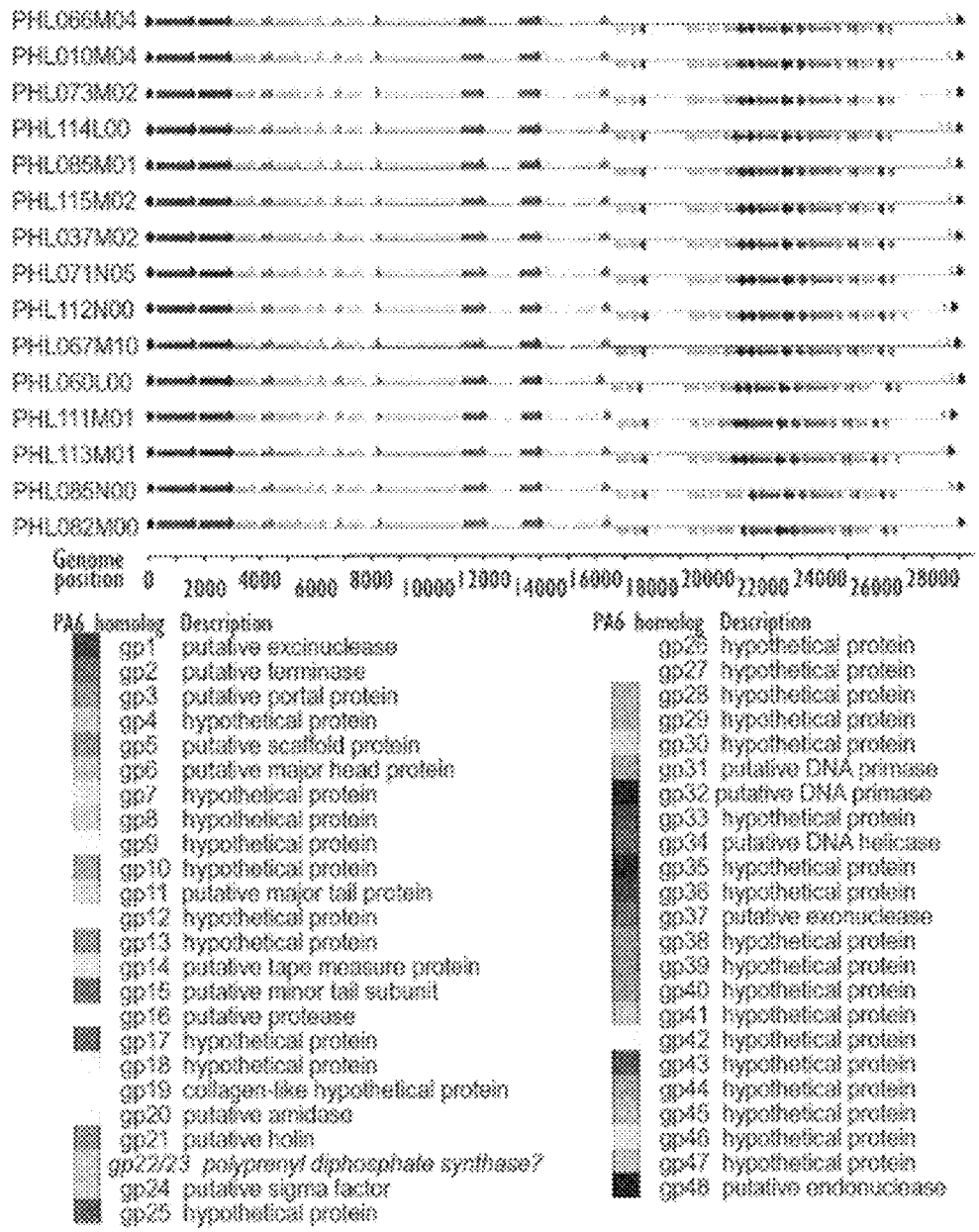
FIG. 29 provides *P. acnes* phage genomes and annotations. Genome organizations of all 15 phages are shown. Hatched arrows in previously published genomes represent newly annotated ORFs proposed. Italicized legend entries refer to newly-annotated or revised ORFs.

*sequenced on the Illumina MiSeq platform.
All other genomes were sequenced on the 454 platform All phage genomes were assembled, completed, and annotated (FIG. 29). The genomes of these 15 phages have comparable sizes (29.1-29.5 Kb) and GC content (53.8-54.5%), similar to the published P. acnes phage genomes. On average, 44 open reading frames (ORFs) were predicted in each genome. Consistent with the genome organization previously reported [11, 15], the ORFs were arranged compactly within the left and right arm regions of each genome. The left arm and right arm of the genomes can be distinguished by their opposite directions of transcription. The sequence identity between any pair of genomes is moderately high, ranging from 78.2 to 99.9% (Table 12).

Figure 30:
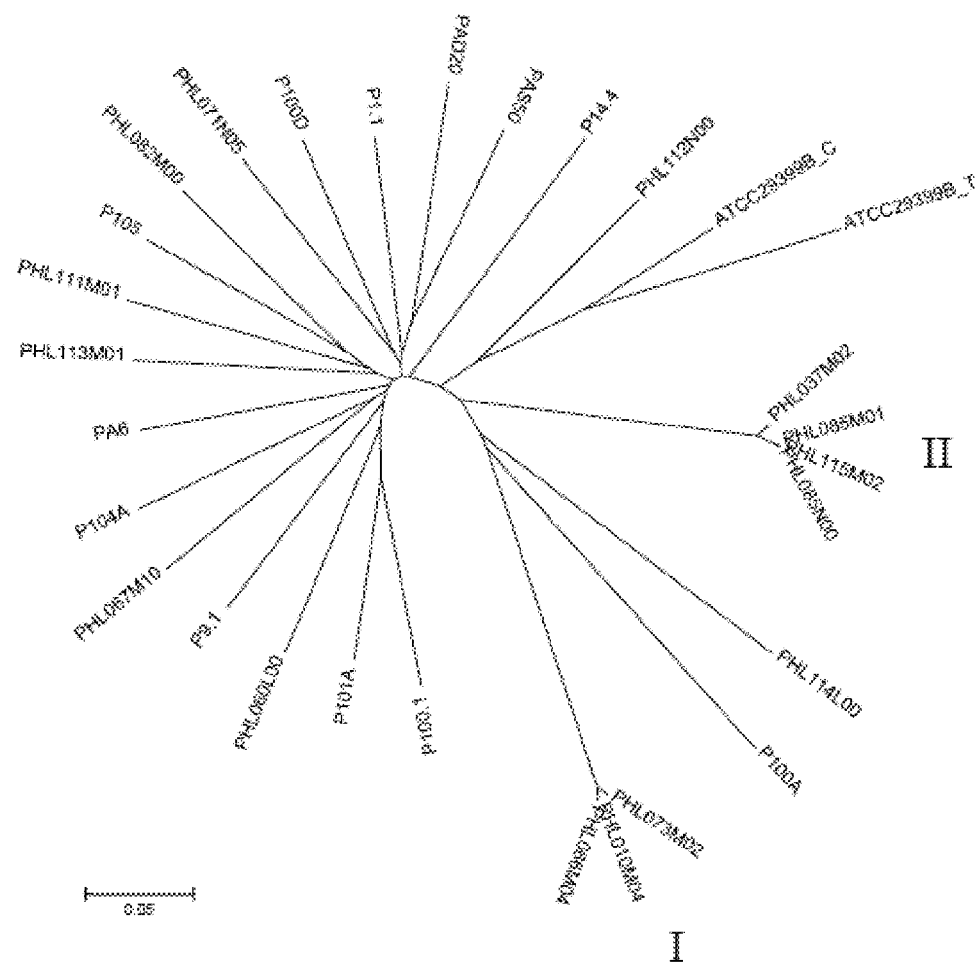
FIG. 30 provides a phylogenetic tree of 29 sequenced phage genomes constructed based upon the 6,148 SNPs in the core regions. Branches with bootstrap values less than 80 (based on 200 resamplings) were collapsed.
Figure 31:
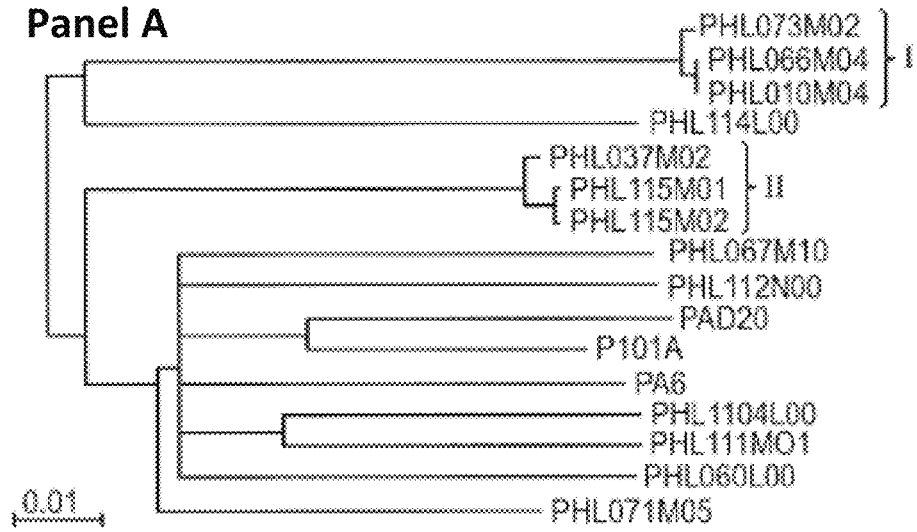
FIG. 31 provides phylogentic trees based on the genome sequences. (A) provides a phylogenetic tree constructed based on the entire genome sequences of all 16 phages. With the exception of PHL112N00, the phylogenetic relationships among the phages remain the same as using the core regions only, shown in FIG. 30. (B) shows the phylogenetic tree that was constructed using only the left-arm of the genomes, which are highly conserved among the phages. (C) shows the phylogenetic tree that was constructed using only the right-arm coding regions. Groups I and II from FIG. 30 are also indicated in the trees. Branches with bootstrap values less than 80 (based on 5,000 resamplings) were collapsed.
Figure 31:
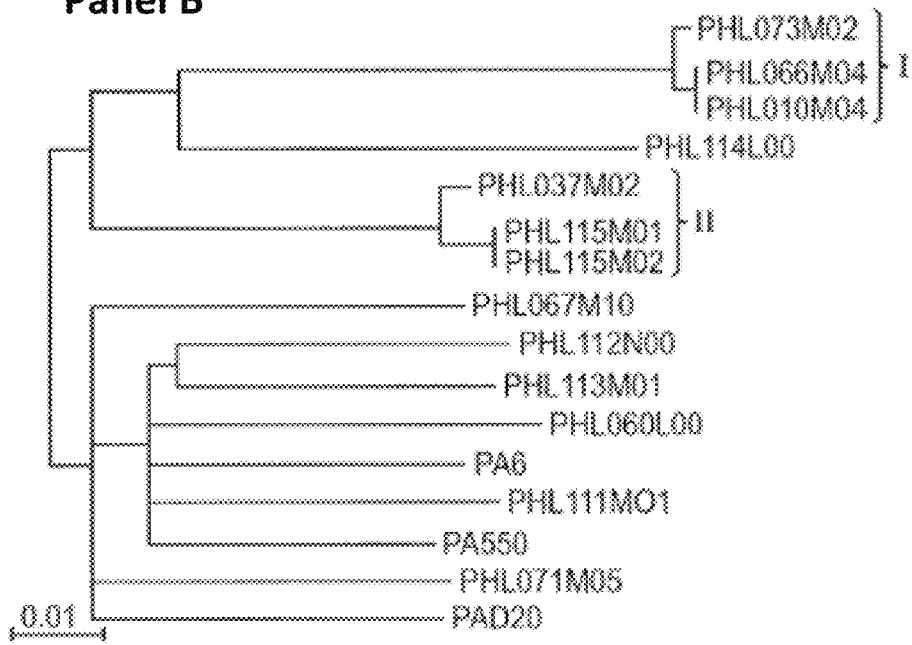
Figure 31:
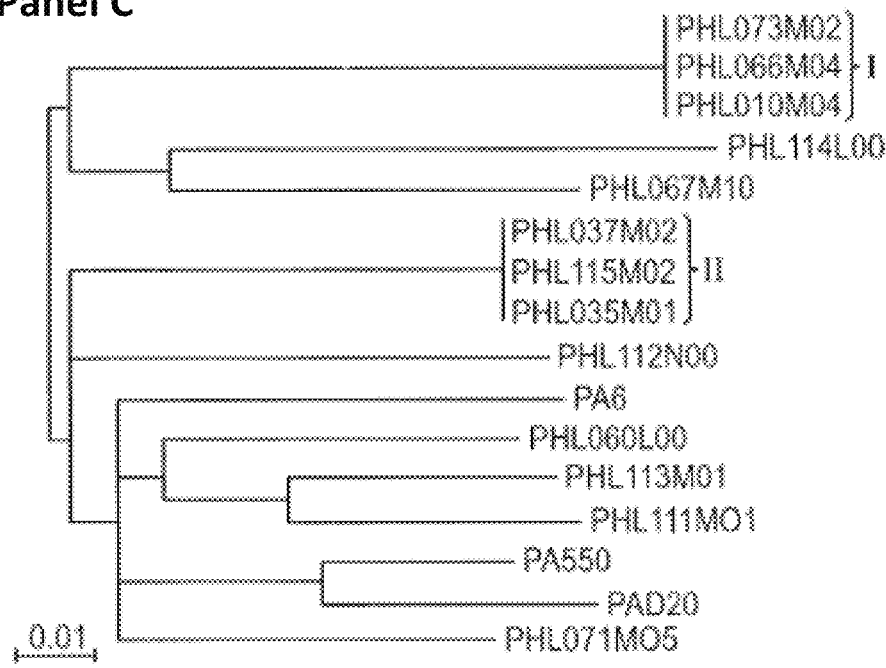

P. acnes Phages are Diverse with Subgroups of Highly Related Strains with Distinct Sites of Genetic Variations To investigate the genome diversity of P. acnes phages, all 29 sequenced phage genomes were compared, including Applicants' 15 phage genomes and the 14 published ones (Farrar et al., 2007; Lood & Collin, 2011; Marinelli et al., 2012). The core genomic regions shared by all 29 genomes have a combined length of 24,475 bp (83% of the average genome length) and contain 6,812 single-nucleotide polymorphisms (SNPs). A phylogenetic tree constructed from these 6,812 SNPs (FIG. 30) shows that most of the phage genomes isolated from all studies to date show comparable divergence from each other with an average distance of 0.301 (substitution rate at the SNP sites). However, also found were two groups of phages, named as Group I and Group II (FIG. 30), that are closely related with much shorter phylogenetic distances. The same results were obtained when the entire genome sequences (including core and non-core regions) were used in the calculation of phylogenetic relationships (FIG. 31).

We next determined whether the newly-sequenced phages belong to the phylogenetic groups discovered before. Lood et al. previously surveyed the phylogenetic diversity of *P. acnes* phages based on the nucleotide sequences encoding head proteins or amidases of phage isolates [12]. Three major phylogenetic groups were reported. Applicants' data were combined with the data from Lood et al. and Applicants reconstructed the phylogenetic trees of head protein and amidase gene sequences. The updated phylogenetic trees reproduced the relationships among the strains from the previous study (FIG. 32). However, Applicants' phages were grouped into separate clades. Moreover, by including the gene sequences from the current study, the longest phylogenetic distance among all studied phages was increased from 0.077 to 0.102 for the head protein gene and from 0.140 to 0.182 for the amidase gene. Although these distances are still considerably shorter than those of the closest outgroups (0.939, head protein from mycobacteriophage Che9d; 0.764, *P. acnes* KPA171202 amidase) [12], the analysis suggests that *P. acnes* phage diversity is broader than previously described.

Some of the *P. acnes* phages appear to be closely related strains as previously shown [12]. Among the 29 sequenced genomes, two groups of closely related strains were observed (FIG. 30). Group I consists of PHL066M04, PHL010M04, and PHL073M02, which are separated by an average phylogenetic distance of 0.002 at the genome level. Group II consists of PHL085M01, PHL085N00, PHL115M02, and PHL037M02, with an average phylogenetic distance of 0.004. These two groups are statistically robust when core regions or the entire genome or only the left-arm or rightarm coding regions were used in calculating the phylogeny (FIGS. 30 and 31).

Whether the genetic variations among Group I phages or Group II phages were located in particular regions of the genomes was investigated. The sites of sequence variation among Group I phages lie primarily within the region encoding a putataive type II holin and a peptidoglycan amidase (Gp20 and Gp21 as annotated in PA6, FIG. 33). These endolysins permeabilize the membrane and degrade the extracellular peptidoglycan layer to release new phage particles from the bacterial host. The majority of the sequence variations in these two genes among the Group I phage genomes are mostly synonymous and do not appear to affect the functions of the proteins. The genomes of PHL010M02 and PHL066M02 differ at only 11 sites, 9 of which occur in predicted coding regions.

Figure 33:
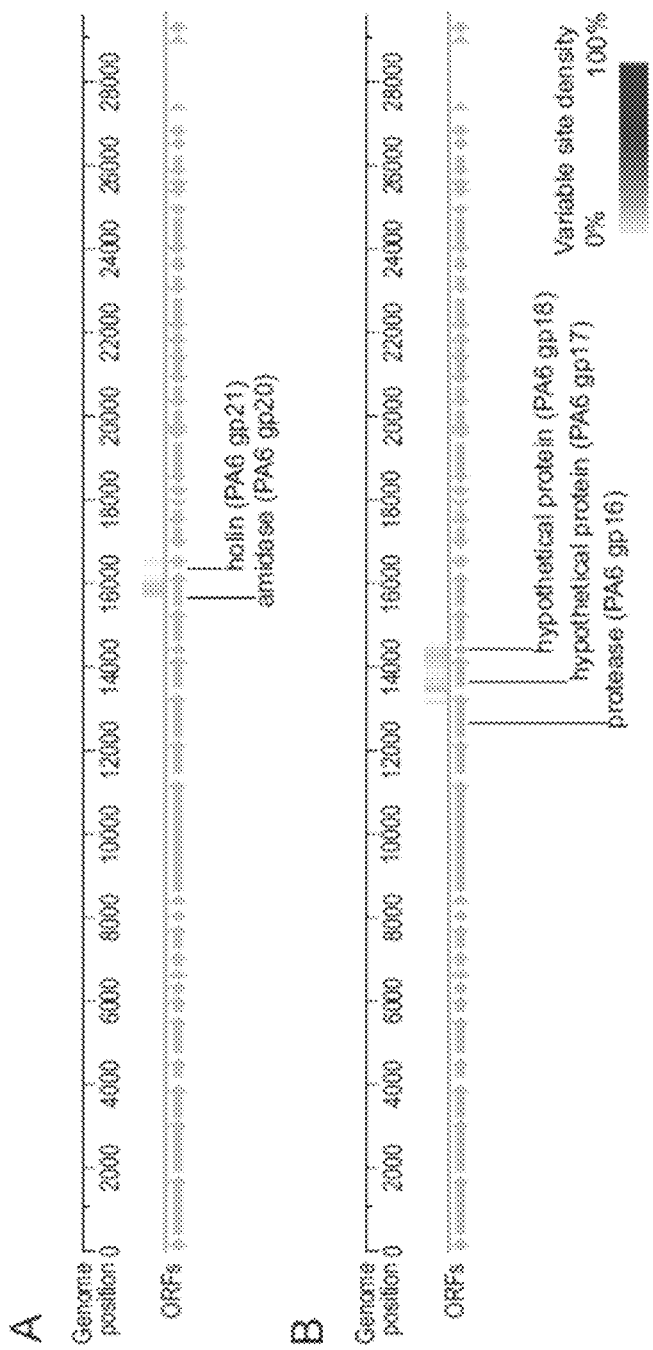
FIG. 33 reflects multiple alignments generated for genomes from Groups I and II of closely-related phages. Sites of nucleotide variations are mapped to a member from each group. The density of variable sites in each 50-nt window of the genome is indicated in red, with 100% density indicating that all 50 sites in the window vary between the group members. (A) provides variations among Group I phages (PHL010M04, PHL066M04, PHL073M02) mapped to the PHL010M04 genome. (B) provides variation among Group II phages (PHL115M02, PHL085M01, PHL085N00, PHL037M02) mapped to the PHL115M02 genome. Gray arrows represent ORFs in each genome.

Genetic variations among Group II members reside in a region encoding homologs of Gp16, Gp17, and Gp18 in PA6 (FIG. 33). These proteins' location near the 3' end of the left arm between structural proteins and lysis proteins suggests that they may be late-acting genes involved in viral protein processing and packaging.

Alternative Annotations of *P. acnes* Phage Genomes

The large number of newly-sequenced *P. acnes* phage strains provided an opportunity to validate and refine initial annotations of the *P. acnes* phage genomes. Based on the analysis, several alternative annotations of the phage genomes were confirmed.

All 15 phage genomes that were sequenced support an alternative annotation of the Gp22/23 locus, which was previously annotated as two ORFs, Gp22 and Gp23, encoded on the plus-strand in the PA6 genome. Homologs of the PA6 genes Gp22 and Gp23 were not consistently identified in the genomes, as many of the homologs have inconsistent start and stop codon positions at the expected plus-strand locations of these genes. However, on the minus-strand, all genomes appear to encode a single ORF with a length of 513-522 bp. This annotation is consistent with the annotation reported by Marinelli et al. (Marinelli et al., 2012), which is referred to herein as Gp22/23 (FIG. 29). While no known function was assigned to Gp22 or Gp23 of the original plus-strand annotation, the minus-strand annotation of Gp22/23 in PHL112N00 and PHL111M01 showed modest similarity to a zinc finger protein from *Arthroderma gypseum* (E-values 1.0e-4 and 5.7e-4, respectively). The PHL111M01 annotation also showed similarity to a polyprenyl diphosphate synthase from *Streptomyces albus* (E-value 2.6e-5) and a polyketide synthase from the *Frankia* genus (E-value 2.5e-4). The minus-strand Gp22/23 ORFs from most genomes are homologs of each other, except those in PHL067M10 and PHL114L00. The Gp22/23 ORFs in these two genomes form a separate group and share little nucleotide similarity to the other Gp22/23 ORFs despite being present at the same locus in the genome. The observation that this ORF appears in all the phage genomes on the minus strand suggests that this region may be part of the right arm. This is consistent with previous reports of a plus-strand transcriptional terminator that separates Gp22/23 from the rest of the left arm in PA6, PAD20, and PAS50 [11].

Homologs of the PA6 ORFs Gp42, Gp45, and Gp46, which occur in the right-arm of the genome near the ~1 kb non-coding region, were not consistently identified. The expected locations of each of these right-arm ORFs in the phage genomes frequently contained numerous stop codons and showed limited homology to corresponding regions of the PA6 genome. This is consistent with the generally high degree of nucleotide variation near the non-coding region and suggests that these ORFs may represent genes that are differentially present among different phage strains.

The sequencing data demonstrated that the ends of the phage genomes are flanked by 11-nucleotide single-stranded overhangs (Table 12). In the sequencing data of 10 phage genomes, 1-3 reads that span both the 3' and 5' ends of the genomes were found. The genome ends in these reads are consistently separated by a sequence that matches the 11-nt single-stranded extension previously reported (Marinelli et al., 2012). However, based on the sequencing data, the presence of overhangs in three of the 15 genomes: PHL010M04, PHL073M02, and PHL071N05, were not shown. It is possible that they were simply not detected, as overhang-containing reads were rarely observed in general (2.3 overhang reads per 10,000 reads). Nevertheless, the data do suggest that the phage DNA could be circularized at some point in their life cycle, as previously proposed [11]. The absence of the overhang sequence in reads that map to only one end of the genome may be an artifact of sample processing, as T4 DNA polymerase is used to 'polish' fragmented library DNA by digesting 3' single-strand extensions and extending the complement of 5' single-strand extensions (Roche Diagnostics, 2009). If so, it is surmisable that the overhang may exist on the 3' ends of the genome.

Host Range and Specificity of *P. acnes* Phages

To investigate the host range and specificity of *P. acnes* phages, the 15 sequenced phages were screened against a panel of 69 *Propionibacterium* strains, including 65 *P. acnes* strains, three *P. humerusii* strains, and one *P. granulosum* strain. Except for the *P. acnes* strains KPA171202 and ATCC11828, all of these *Propionibacterium* strains were isolated from the same cohort of subjects sampled for phages. The genomes of all 65 *P. acnes* strains and three *P. humerusii* strains were sequenced. A phylogenetic tree of the 65 *P. acnes* strains based on the SNPs in their core genomic regions was constructed (FIG. 33, left dendrogram). Based on the previously established typing of *P. acnes* strains by their RecA gene sequences [7], the bacterial collection included all major lineages of *P. acnes* found on the human skin, with multiple strains representing each type: IA-1, IA-2, IB-1, IB-2, IB-3 and II. The susceptibility/resistance of each of the 69 bacterial strains against each of our 15 sequenced phages was determined using a crossstreak method. In total, 1,035 bacterium-phage interactions were determined. Each experiment was repeated at least five times. For the bacterial strains that showed resistance to phages, the fold changes in efficiency of plaquing (EOP) was determined relative to the *P. acnes* strain ATCC6919, which is known to be susceptible to all tested strains.

Figure 34:
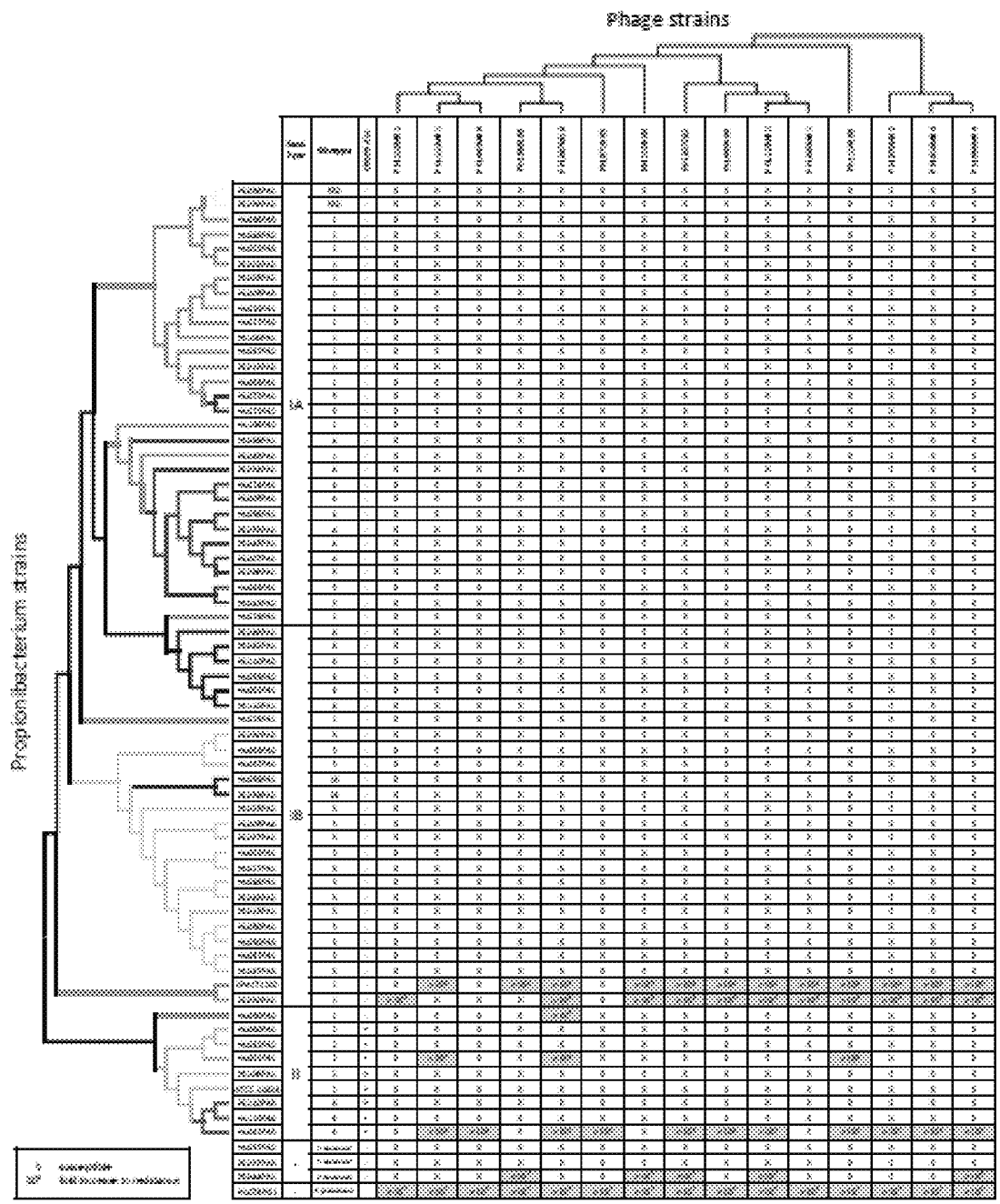
FIG. 34 shows host range and specificity of *P. acnes* phages. The susceptibility/resistance of 66 *P. acnes* strains, three *P. humerusii* strains, and one *P. granulosum* strain against 15 newly sequenced phages is shown. Dendrograms on the top and to the left represent the respective phylogenetic trees of the phages and *P. acnes* strains (only topology is shown). "S" indicates that the tested *Propionibacterium* strain was susceptible to the tested phage. Numbers in red represent the fold increase in resistance of the Propionibacteria strains against phages relative to *P. acnes* strain ATCC6919.

It was found that the susceptibility/resistance to phage is correlated with the *P. acnes* lineages. Five of the 69 *Propionibacterium* strains showed a 100-fold or greater increase in resistance against at least one phage. *P. acnes* strains of types IA-1, IA-2, IB-1, and IB-2 were all susceptible to all tested phages. However, two strains of type IB-3 (KPA171202 and HL030PA1) were highly resistant to some of the phages (FIG. 34). Type IB-3 strains encode components of a type III restriction modification system (genes PPA1611 and PPA1612 in KPA171202). This may explain their resistance to phages. KPA171202 encodes a cryptic prophage in the genome [17]. However, the sequence of the prophage is not related to any of the sequenced *P. acnes* phages, therefore, the presence of the cryptic prophage is unlikely to explain the resistance to phages. Three type II strains were also highly resistant to some of the phages. This is consistent with previous observations that strains of this type were more frequently resistant to phages [14].

On the other hand, the susceptibility/resistance of *P. acnes* strains to phages did not correlate with phage lineages (r=0.1343, p-value=0.115, Mantel test). Even the host ranges among closely-related phage strains in Group I or Group II are different (FIG. 34). One example is PHL066M04, a Group I phage that showed little similarity to other phages in the same group, but had a similar bacterium-phage interaction pattern to the Group II phages PHL115M02 and PHL037M02. These results suggest that bacterial factors may play an important role in determining the phage host range and specificity.

To determine whether these phages are specific to only *P. acnes* or if they are capable of interacting with other Propionibacteria, included were one *P. granulosum* strain and three *P. humerusii* strains in the bacterium-phage interaction experiment. *P. granulosum* is a common skin commensal with approximately 1.1% abundance in the pilosebaceous unit [7]. *P. humerusii* is a newly-defined species [18]. In the study cohort, *P. humerusii* is one of the major species found on the skin with an abundance of 1.9% in the pilosebaceous unit [7]. It is closely related to *P. acnes* with >98% identity in the 16S rRNA gene sequence [18]. While the *P. granulosum* strain showed strong resistance to all the phages tested, two *P. humerusii* strains, HL037PA2 and HL037PA3, were susceptible to all the phages. The third *P. humerusii* strain, HL044PA1, was lysed by ten of the 15 phages tested. This suggests that the host range of *P. acnes* phages is not limited to *P. acnes* but also includes *P. humerusii* and possibly other closely-related *Propionibacterium* species.

Resistance to Bacteriophages does not Correlate with the Presence of Matching CRISPR Spacers in *P. acnes* Strains Among the 65 *P. acnes* isolates, eight strains belong to RT2 and RT6 (RecA type II) and encode CRISPR/Cas genes, which function as a bacterial adaptive immune mechanism against foreign DNA. These RT2 and RT6 strains each have one to nine spacers, 33 nucleotides long, in their CRISPR arrays. In total, they encode 42 spacers, 28 of which are unique.

Figure 35:
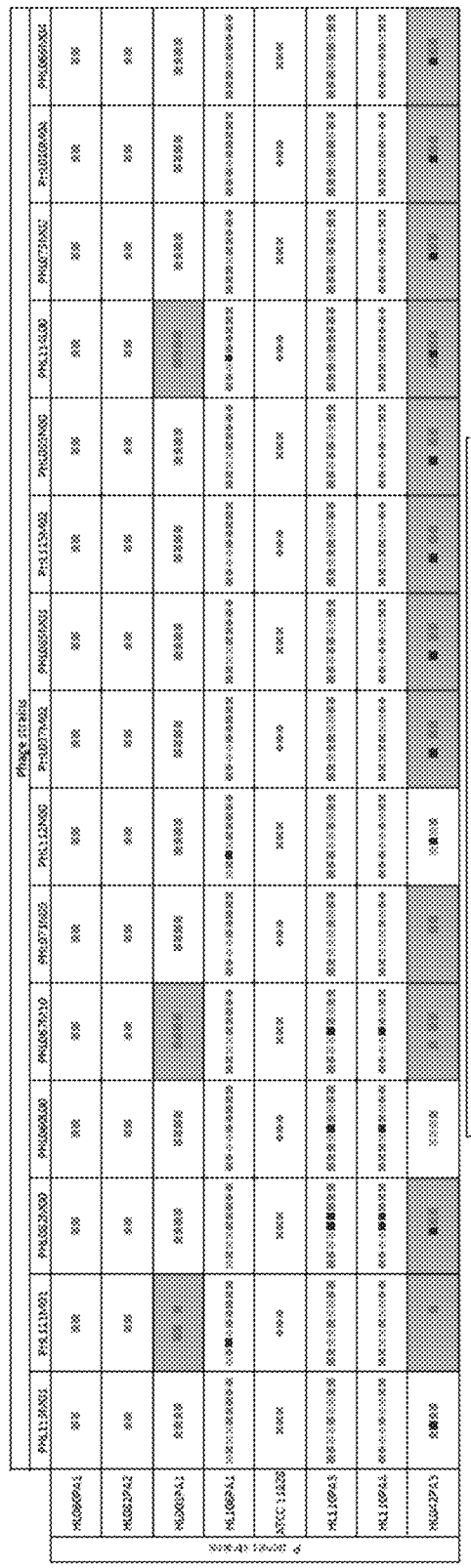
FIG. 35 provides a correlation between *P. acnes* resistance to phages and the presence of matched CRISPR spacers. The colored pixels in each cell represent the CRISPR spacers encoded in each *P. acnes* strain (shown in rows). Each red pixel means that this spacer has an exact protospacer match in the corresponding phage (shown in columns). Each orange pixel means that this spacer has a partially matched protospacer (one to two mismatches) in the corresponding phage. Gray pixels mean no matched protospacers. Pink cells indicate the bacterial resistance to the phages.
Figure 36:
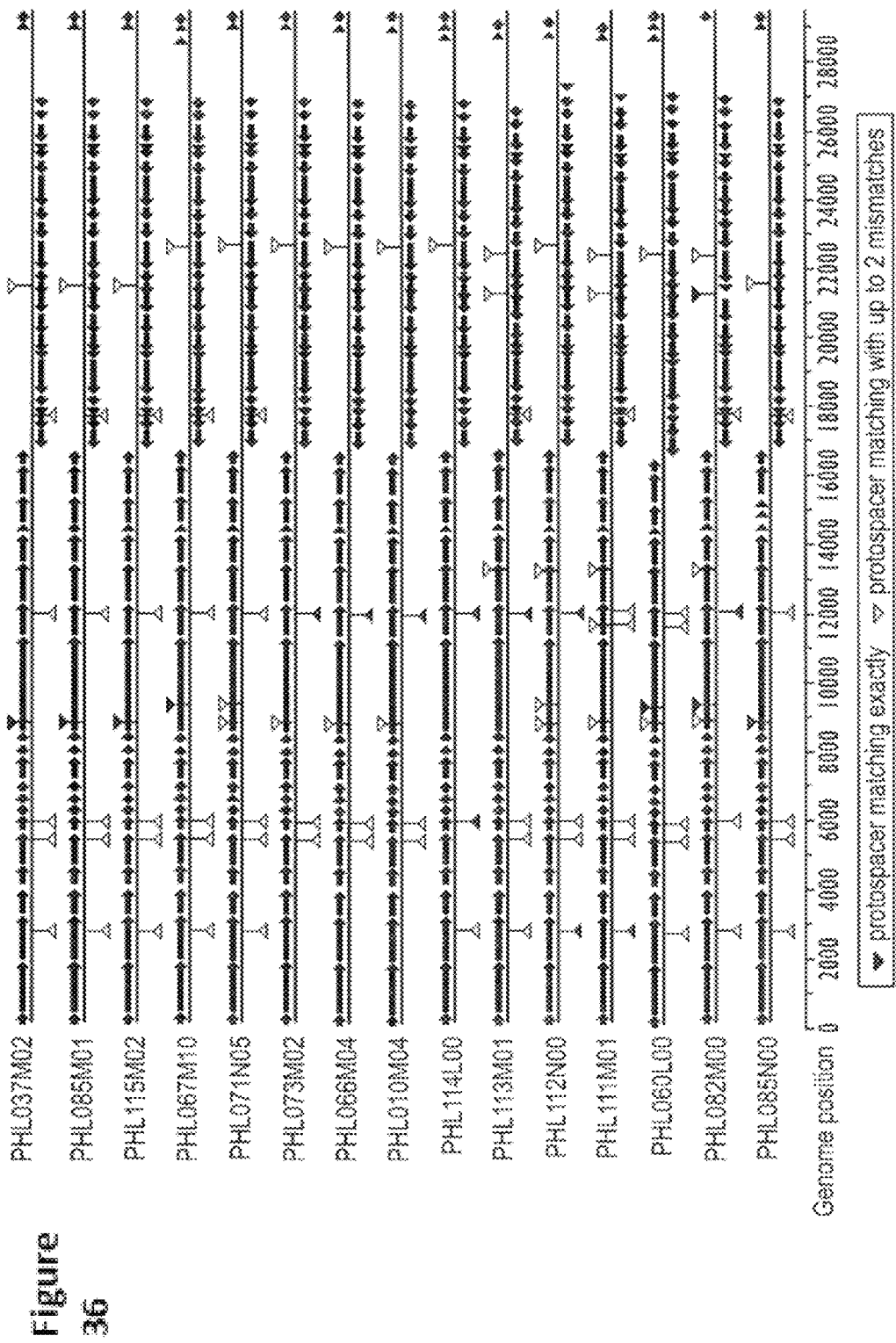
FIG. 36 reflects that each of the 15 sequenced phages was aligned to all 8 CRISPR spacer arrays identified in the *P. acnes* strains to identify protospacer sequences in each phage genome that have an exact match (red) or up to two mismatches (orange). Plus- and minus-strand protospacers are shown above and below the genomes, respectively.

Whether the CRISPR/Cas mechanism can explain phage susceptibility/resistance in the RT2 and RT6 strains was investigated. Protospacers in the 15 phage genomes that match a spacer sequence from the RT2 and RT6 *P. acnes* strains were identified. Up to two mismatches were allowed in the sequence alignments. In all phages, protospacers that match the spacers in at least two *P. acnes* strains were identified (FIG. 35). These protospacers are all single-copied in the phage genomes and are located primarily on the left arm (FIG. 36). Their locations are generally conserved among all other phage genomes harboring the same protospacer sequences.

The susceptibility/resistance patterns of the eight RT2 and RT6 *P. acnes* strains showed little correlation with either the number of spacers in each array that had protospacer matches (r=0.207) or whether at least one match could be found against the CRISPR array in general (r=0.202). Susceptibility/resistance to phages also did not correlate with the pattern with which any specific spacer matched (maximum absolute correlation 0.051).

Figure 37:
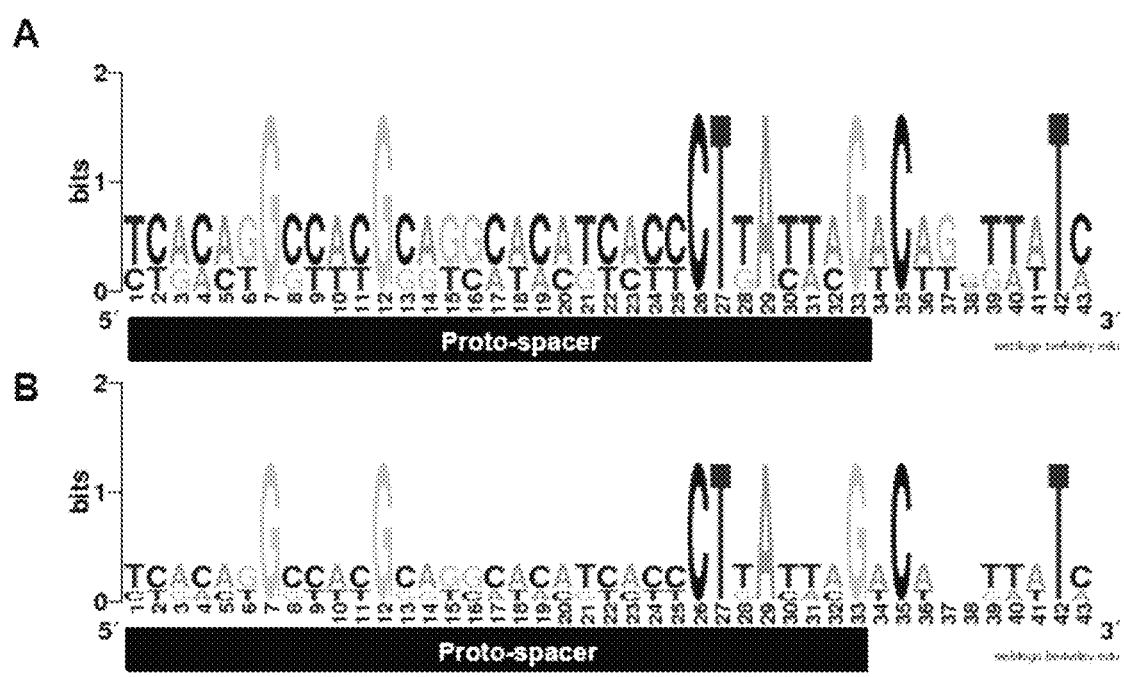
FIG. 37 reflects sequence conservation in protospacers and PAMs. The protospacers that match exactly to the CRISPR spacers encoded in strain HL042PA3 and their associated PAM sequences are shown. Sequence conservation among the protospacer motifs from the phages that HL042PA3 is resistant to is shown in (A) and susceptible to is shown in (B).

Phages can escape the CRISPR defense mechanism by mutating sites involved in protospacer recognition. The short nucleotide motif downstream of the protospacer, known as the protospacer-adjacent motif (PAM), is highly conserved among targets of CRISPR/Cas systems [19]. Mutations in these nucleotides have been found to disrupt CRISPR-mediated resistance despite complete complementarity in the protospacer sequence [20-22]. To determine whether the lack of correlation between bacterial susceptibility/resistance and the presence of matching spacer sequences is due to mutations within the PAM sequence, the PAMs of the nine protospacers that have exact matches to the spacer sequences encoded in HL042PA3 were examined. Six of these protospacers come from phages that HL042PA3 was resistant to, while the other three protospacers are from the phages that were able to lyse HL042PA3. Among the six protospacers, sequence conservation at several sites within their 33-nucleotide length and within the ten downstream nucleotides expected to contain the PAMs were observed (FIG. 37). This suggests that these protospacer motifs are conserved and can be targeted by HL042PA3 CRISPRs. However, these same nucleotide positions are also conserved in the three protospacers from other phages (PHL113M01, PHL112N00, and PHL085M01) that were able to lyse HL042PA3 (FIG. 37). Thus, the conservation of protospacer motifs including the PAMs cannot explain the lack of correlation between bacterial susceptibility/resistance and the presence of matching spacer sequences In summary, the data demonstrate that encoding CRISPR spacers that match against the genome of an invading phage is not sufficient for an effective defense, suggesting that transcriptional and/or translational regulation of CRISPR RNA and Cas gene expression may also be required for CRISPR-mediated resistance. Interactions between these bacteria and phages may also depend on additional phage and bacterial components involved in phage binding, entry, replication, or release.

A diverse group of *P. acnes* bacteriophages that reside on the human skin has been revealed. Most of the sequenced phages show moderately high genetic similarity with certain strains forming closely-related groups. These phages show various patterns of interaction with *P. acnes* and *P. humerusii* strains, but these patterns do not correlate with phage phylogeny. It was determined that resistance or susceptibility to phages correlated well with *P. acnes* lineages. Types IA-1, IA-2, IB-1, and IB-2 were all susceptible to all tested phages, while certain strains of types IB-3 and II were resistant to some phages. Phage resistance in type II *P. acnes* strains does not correlate with the presence of CRISPR spacers that match to phage protospacers, suggesting that additional mechanisms, such as regulation of the CRISPR/Cas system and/or other antiviral mechanisms, are needed in conferring the phage resistance.

This study suggests an important regulatory role of *P. acnes* bacteriophages in the skin microbiome. The strain-specific host ranges demonstrate the ability of these phages to regulate particular subsets of the *P. acnes* population and *P. humerusii* population. Among these subsets of *Propionibacterium* populations, phages may also disseminate genes that potentially modify virulence, as suggested by Lood and Collin [11], or competitiveness, as it was suggested that gp22/23 encoded in some phages may be potentially involved in the production of polyketide antimicrobials. Both the selective lysis and modification of *P. acnes* strains by phages potentially regulates the relative abundances of the commensal and pathogenic strains of *P. acnes* on the skin. This delicate balance between commensals and pathogens can be especially important for skin health and disease at sites where *P. acnes* dominates. Based on the metagenomic shotgun sequencing data, it is estimated that the ratio between *P. acnes* phage and *P. acnes* in the pilosebaceous unit is 1:20 [7], which is far different from the phage:bacteria ratios estimated in environmental microbial communities, where viruses typically outnumber bacteria [23]. This suggests that the human host also plays a role in selecting and regulating the composition and diversity of the microbiome.

Materials and Methods

Propionibacteria Culture

*P. acnes*, *P. humerusii*, and *P. granulosum* strains were cultured under anaerobic conditions in Clostridial media (Oxoid) at 37° C. for 4-6 days. *Propionibacterium* cultures were used to prepare top agar overlays for phage culture on A media plates (12 g/L pancreatic digest of casein, 12 g/L Difco yeast extract, 22.2 mM D-glucose, 29.4 mM g/L potassium phosphate monobasic, 8 mM magnesium sulphate heptahydrate, 20 g/L Difco agar).

Phage Isolation and DNA Extraction

Plaques found on skin sample culture plates were isolated by puncturing the agar with a pipet tip and resuspending in 50 μL SM buffer (0.1 M sodium chloride, 8 mM magnesium sulfate heptahydrate, 1M Tris-HCl, pH 7.5, 2% gelatin, 1 mM calcium chloride). The phage resuspension was spread onto A media plates with top agar containing *P. acnes* strain ATCC 6919. After incubation at 37° C. for 2 days, phages were eluted with 8 mL SM buffer at room temperature, filtered with 0.22 uM PES filter (Millipore), and stored at 4° C. Phage titers were determined by plaque assay.

Phage DNA extraction was performed using the Lambda Mini Kit (Qiagen) with the following modifications. Phage particles were precipitated in Buffer L2 by centrifugation at 20,000 g for 1 hour. Extracted DNA was eluted with Buffer QF and precipitated with isopropanol overnight at −20° C. before centrifugation.

Phage Genome Sequencing and Annotation

Phage genomes were sequenced in multiplex using the Roche GS FLX Titanium or Illumina MiSeq platforms. De novo assembly of reads was performed with MIRA [24], and the resulting contigs were manually finished in Consed [25]. For phages covered by more than 20,000 reads, assembly was performed on a randomly-selected subset of 10,000 reads for 454 data or 20,000 reads for MiSeq data. Fully assembled phage genomes were annotated using Genemark.hmm [26] and Glimmer v3.02 [27].

Genome Sequence Alignment and Phylogenetic Tree Construction

Sequences present in all 16 phage genomes were defined as core regions of the phage genome. To identify these core regions, alignments were first generated between the PA6 genome and each of the other 15 phage genomes using Nucmer [28]. This yielded 15 sets of starting and ending coordinates describing intervals within the PA6 genome that align with any given phage genome. The core regions were then calculated for all phages by determining the overlapping intervals between all of the 15 coordinate sets. The core region sequences were concatenated for the subsequent multiple sequence alignments. Single nucleotide polymorphisms (SNPs) on the core regions were identified by using the "show-snps" option of Nucmer with the default setting. Using MEGA5 [29], phylogenetic trees were constructed by the Neighbor Joining method on p-distances based on SNP sites. Bootstrapping was based on 200 replicates.

Multiple sequence alignments of full-length phage genomes, left and right arm coding regions, head protein sequences, and amidase sequences were each generated with MAFFT [30] or Muscle [31]. Phylogenetic trees were constructed in Seaview [32] based on the BioNJ method applied to the Jukes-Cantor distances between the sequences. All trees were bootstrapped for 5,000 replicates.

Determination of Variation Sites

Multiple sequence alignments of Group I and Group II phages were generated using MAFFT [30]. In each of these alignments, the positions of all mismatches and gaps (discrepancies) were recorded relative to a reference genome that was chosen at random. Contiguous gaps in the reference genome were counted as a single discrepancy. The reference genome was divided into 50-nucleotide windows, and the discrepancy density of each sequence window was calculated as the total number of discrepancies it contained. Densities were plotted in Artemis [33].

To determine the single-nucleotide variations within each strain, all read data for each phage, including reads not initially included in the de novo genome assembly, were mapped to their corresponding genomes using Mira. as the sites in each phage genome assembly.

Bacterial Resistance Test

The susceptibilities/resistances of *Propionibacterium* strains against 15 phages were determined using a modified cross-streak assay. The bacterial strains were cultured and streaked in parallel across A media plates (5-6 isolates on each plate, ~1 cm apart, along with ATCC 6919 as a control). Approximately 5 μL of 106 pfu/mL phage suspension was applied onto each streak, and then the plates were incubated at 37° C. anaerobically for 2 days. At least five replicates of each cross-streak experiment were performed to determine whether the strains were susceptible or resistant judged based on lysis. The resistance of the bacterial strains was further quantified by assaying the efficiency of plaquing of the phages relative to *P. acnes* strain ATCC 6919, calculated as the following:

$$\text{Resistance} = \frac{1}{\text{Efficiency of Plaquing}} = \frac{\text{Titer of Phage Strain } X \text{ on } ATCC6919}{\text{Titer of Phage Strain } X \text{ on Bacterial Strain } Y}$$

A 100-fold or greater increase in efficiency of plaquing was considered to be evidence of resistance.

Phage Interaction Correlation

To determine whether genetically similar phages have similar host range and specificity, the correlation between their phylogenetic and phenotypic relationships was calculated, the latter based on results from the bacterial resistance test. Each column in the bacterial resistance table, which represents the host range of a given phage, was converted to binary form by assigning 1 to instances of resistance and 0 to instances of susceptibility. The Euclidean distance between each column was used to calculate a phenotype distance matrix between all phages. A phylogenetic distance matrix among the phage genomes was calculated using MEGA5 [29]. Using the ade4 package [34] in R, a Mantel test was performed on the phenotype and phylogenetic distance matrices to determine the correlation between the two. 10,000 permutations were performed.

CRISPR Search

CRISPR spacer sequences were identified in *P. acnes* genomes using CRISPRfinder [35]. The extracted spacer sequences were aligned against all phage sequences using BLASTn. Protospacers with up to two mismatches were identified.

Results

The genomes of 15 *P. acnes* phages isolated from human skin were sequenced. The phage genomes showed moderately high sequence similarity and were comparable in size and organization. Based on a comparison of the genomes, most phages diverge from each other, while some of them form closely-related groups that were not described previously. When tested against a panel of 69 *Propionibacterium* strains, these phages lysed all *P. acnes* strains except some strains from type IB-3 and II. Some of the phages were also able to lyse *Propionibacterium humerusii* strains. It was found that bacterial susceptibility/resistance to phages had no significant correlation with phage phylogeny or the presence of the CRISPR spacers in type II *P. acnes* strains that match the protospacers in the phage genomes.

Conclusions

With 15 new phagel genomes, it was determined that the diversity of *P. acnes* phages is broader than previously described with novel groups added. The host range and specificity are different among the phages, but are not correlated with the phylogeny of phage genomes. It was also found that encoding CRISPR spacers that match to phage genomes is not sufficient to confer *P. acnes* resistance to phages. This study provides new insight into the potential application of phages in treating acne and other *P. acnes* associated diseases.

REFERENCES CITED IN EXAMPLE 8

1. Mc Grath S, van Sinderen D (eds): Bacteriophage: Genetics and Molecular Biology. Norfolk, UK: Caister Academic Press; 2007.
2. Rohwer F: Global phage diversity. Cell 2003, 113:141.
3. Rohwer F, Thurber R V: Viruses manipulate the marine environment. Nature 2009, 459:207-212.
4. Suttle C A, Chan A M, Cottrell M T: Infection of Phytoplankton by Viruses and Reduction of Primary Productivity. Nature 1990, 347:467-469.
5. Rodriguez-Valera F, Martin-Cuadrado A B, Rodriguez-Brito B, Pasic L, Thingstad T F, Rohwer F, Mira A: Explaining microbial population genomics through phage predation. Nature reviews Microbiology 2009, 7:828-836.
6. Grice E A, Segre J A: The skin microbiome. Nature reviews Microbiology 2011, 9:244-253.
7. precedings.nature.com/documents/5305/version/1
8. Bojar R A, Holland K T: Acne and *Propionibacterium acnes*. Clin Dermatol 2004, 22:375-379.
9. Leyden J J: The evolving role of *Propionibacterium acnes* in acne. Semin Cutan Med Surg 2001, 20:139-143.
10. Zierdt C H, Webster C, Rude W S: Study of the anaerobic corynebacteria. International Journal of Systematic Bacteriology 1968, 18:33-47.
11. Lood R, Collin M: Characterization and genome sequencing of two *Propionibacterium acnes* phages displaying pseudolysogeny. BMC genomics 2011, 12:198.
12. Lood R, Morgelin M, Holmberg A, Rasmussen M, Collin M: Inducible Siphoviruses in superficial and deep tissue isolates of *Propionibacterium acnes*. BMC microbiology 2008, 8:139.
13. Jong E C, Ko H L, Pulverer G: Studies on bacteriophages of *Propionibacterium acnes*. Med Microbiol Immunol 1975, 161:263-271.
14. Webster G F, Cummins C S: Use of bacteriophage typing to distinguish *Propionibacterium* acne types I and II. Journal of clinical microbiology 1978, 7:84-90.
15. Farrar M D, Howson K M, Bojar R A, West D, Towler J C, Parry J, Pelton K, Holland K T: Genome sequence and analysis of a *Propionibacterium acnes* bacteriophage. Journal of bacteriology 2007, 189:4161-4167.
16. Horvath P, Barrangou R: CRISPR/Cas, the immune system of bacteria and archaea. Science 2010, 327:167-170.
17. Brzuszkiewicz E, Weiner J, Wollherr A, Thurmer A, Hupeden J, Lomholt H B, Kilian M, Gottschalk G, Daniel R, Mollenkopf H J, et al: Comparative genomics and transcriptomics of *Propionibacterium acnes*. PloS one 2011, 6:e21581.
18. Butler-Wu S M, Sengupta D J, Kittichotirat W, Matsen F A, 3rd, Bumgarner R E: Genome sequence of a novel species, *Propionibacterium humerusii*. Journal of bacteriology 2011, 193:3678.
19. Mojica F J, Diez-Villasenor C, Garcia-Martinez J, Almendros C: Short motif sequences determine the targets of the prokaryotic CRISPR defence system. Microbiology 2009, 155:733-740.
20. Westra E R, van Erp P B, Kunne T, Wong S P, Staals R H, Seegers C L, Bollen S, Jore M M, Semenova E, Severinov K, et al: CRISPR immunity relies on the consecutive binding and degradation of negatively supercoiled invader DNA by Cascade and Cas3. Molecular cell 2012, 46:595-605.
21. Semenova E, Jore M M, Datsenko K A, Semenova A, Westra E R, Wanner B, van der Oost J, Brouns S J, Severinov K: Interference by clustered regularly interspaced short palindromic repeat (CRISPR) RNA is governed by a seed sequence. Proceedings of the National Academy of Sciences of the United States of America 2011, 108:10098-10103.
22. Semenova E, Nagornykh M, Pyatnitskiy M, Artamonova, II, Severinov K: Analysis of CRISPR system function in plant pathogen *Xanthomonas oryzae*. FEMS microbiology letters 2009, 296:110-116.

23. Srinivasiah S, Bhaysar J, Thapar K, Liles M, Schoenfeld T, Wommack K E: Phages across the biosphere: contrasts of viruses in soil and aquatic environments. Research in microbiology 2008, 159:349-357.
24. Chevreux B, Pfisterer T, Drescher B, Driesel A J, Muller W E, Wetter T, Suhai S: Using the miraEST assembler for reliable and automated mRNA transcript assembly and SNP detection in sequenced ESTs. Genome research 2004, 14:1147-1159.
25. Gordon D, Abajian C, Green P: Consed: a graphical tool for sequence finishing. Genome research 1998, 8:195-202.
26. Lukashin A V, Borodovsky M: GeneMark.hmm: new solutions for gene finding. Nucleic acids research 1998, 26:1107-1115.
27. Delcher A L, Harmon D, Kasif S, White O, Salzberg S L: Improved microbial gene identification with GLIMMER. Nucleic acids research 1999, 27:4636-4641.
28. Kurtz S, Phillippy A, Delcher A L, Smoot M, Shumway M, Antonescu C, Salzberg S L: Versatile and open software for comparing large genomes. Genome biology 2004, 5:R12.
29. Tamura K, Peterson D, Peterson N, Stecher G, Nei M, Kumar S: MEGA5: molecular evolutionary genetics analysis using maximum likelihood, evolutionary distance, and maximum parsimony methods. Molecular biology and evolution 2011, 28:2731-2739.
30. Katoh K, Misawa K, Kuma K, Miyata T: MAFFT: a novel method for rapid multiple sequence alignment based on fast Fourier transform. Nucleic acids research 2002, 30:3059-3066.
31. Edgar R C: MUSCLE: multiple sequence alignment with high accuracy and high throughput. Nucleic acids research 2004, 32:1792-1797.
32. Gouy M, Guindon S, Gascuel O: SeaView version 4: A multiplatform graphical user interface for sequence alignment and phylogenetic tree building. Molecular biology and evolution 2010, 27:221-224.
33. Rutherford K, Parkhill J, Crook J, Horsnell T, Rice P, Rajandream M A, Barrell B: Artemis: sequence visualization and annotation. Bioinformatics 2000, 16:944-945.
34. Dray S, Dufour A B: The ade4 package: Implementing the duality diagram for ecologists. Journal of Statistical Software 2007, 22:1-20.
35. Grissa I, Vergnaud G, Pourcel C: CRISPRFinder: a web tool to identify clustered regularly interspaced short palindromic repeats. Nucleic acids research 2007, 35:W52-57.

(Nature Precedings Paper). (n.d.). Retrieved from precedings.nature.com/documents/5305/version/1

Bojar, R. a, & Holland, K. T. (2004). Acne and *Propionibacterium acnes*. Clinics in dermatology, 22(5), 375-9. doi:10.1016/j.clindermato1.2004.03.005

Farrar, M. D., Howson, K. M., Bojar, R. a, West, D., Towler, J. C., Parry, J., Pelton, K., et al. (2007). Genome sequence and analysis of a *Propionibacterium acnes* bacteriophage. Journal of bacteriology, 189(11), 4161-7. doi:10.1128/JB.00106-07

Grice, E. a, & Segre, J. a. (2011). The skin microbiome. Nature reviews. Microbiology, 9(4), 244-53. doi:10.1038/nrmicro2537

Leyden, J. J. (2001). The evolving role of *Propionibacterium acnes* in acne. Seminars in cutaneous medicine and surgery, 20(3), 139-43. doi:10.1053/sder.2001.28207

Lood, R., & Collin, M. (2011). Characterization and genome sequencing of two *Propionibacterium acnes* phages displaying pseudolysogeny. BMC genomics, 12(1), 198. doi:10.1186/1471-2164-12-198

Marinelli, L. J., Fitz-gibbon, S., Hayes, C., Bowman, C., Inkeles, M., Loncaric, A., & Russell, D. A. (2012). *Propionibacterium acnes* Bacteriophages Display Limited Genetic Diversity and Broad Killing Activity against Bacterial Skin Isolates. mBio, 3(5), 1-13. doi:10.1128/mBio.00279-12.Editor Mc Grath, S., & van Sinderen, D. (eds). (2007). Bacteriophage: Genetics and Molecular Biology. Norfolk, UK: Caister Academic Press.

Roche Diagnostics. (2009). GS FLX Titanium General Library Preparation Method Manual. Mannheim: Roche Diagnostics GmbH.

Rodriguez-Valera, F., Martin-Cuadrado, A.-B., Rodriguez-Brito, B., Pasić, L., Thingstad, T. F., Rohwer, F., & Mira, A. (2009). Explaining microbial population genomics through phage predation. Nature reviews. Microbiology, 7(11), 828-36. doi:10.1038/nrmicro2235

Rohwer, F. (2003). Global phage diversity. Cell, 113(2), 141.

Zierdt, C. H., Webster, C., & Rude, W. S. (1968). Study of the anaerobic corynebacteria. International Journal of Systematic Bacteriology, 18, 33-47.

All the strains of RT4, RT5, and RT8 show sensitivity to all of the phages shown in Table 13. Therefore, acne patients may be treated with phage by using phage strains that are listed in Table 13:

TABLE 13

Host range and specificity of *P. acnes* phages

| | RecA Type | Ribo-type | CRISPR/Cas | PHL113M01 | PHL111M01 | PHL082M00 | PHL060L00 | PHL067M10 | PHL071N05 |
|---|---|---|---|---|---|---|---|---|---|
| HL036PA1 | IA | 532 | − | S | S | S | S | S | S |
| HL036PA2 | | 532 | − | S | S | S | S | S | S |
| HL036PA3 | | 1 | − | S | S | S | S | S | S |
| HL046PA2 | | 1 | − | S | S | S | S | S | S |
| HL002PA3 | | 1 | − | S | S | S | S | S | S |
| HL002PA2 | | 1 | − | S | S | S | S | S | S |
| HL005PA2 | | 1 | − | S | S | S | S | S | S |
| HL005PA3 | | 1 | − | S | S | S | S | S | S |
| HL020PA1 | | 1 | − | S | S | S | S | S | S |
| HL027PA2 | | 1 | − | S | S | S | S | S | S |
| HL100PA1 | | 1 | − | S | S | S | S | S | S |
| HL087PA2 | | 1 | − | S | S | S | S | S | S |
| HL013PA2 | | 1 | − | S | S | S | S | S | S |
| HL063PA1 | | 1 | − | S | S | S | S | S | S |
| HL072PA1 | | 5 | − | S | S | S | S | S | S |
| HL072PA2 | | 5 | − | S | S | S | S | S | S |

TABLE 13-continued

Host range and specificity of *P. acnes* phages

| | | | | | | | | | |
|---|---|---|---|---|---|---|---|---|---|
| HL106PA2 | | 1 | – | S | S | S | S | S | S |
| HL099PA1 | | 4 | – | S | S | S | S | S | S |
| HL083PA1 | | 1 | – | S | S | S | S | S | S |
| HL038PA1 | | 1 | – | S | S | S | S | S | S |
| HL074PA1 | | 4 | – | S | S | S | S | S | S |
| HL005PA1 | | 4 | – | S | S | S | S | S | S |
| HL056PA1 | | 4 | – | S | S | S | S | S | S |
| HL053PA1 | | 4 | – | S | S | S | S | S | S |
| HL045PA1 | | 4 | – | S | S | S | S | S | S |
| HL007PA1 | | 4 | – | S | S | S | S | S | S |
| HL096PA1 | | 4 | – | S | S | S | S | S | S |
| HL043PA1 | | 5 | – | S | S | S | S | S | S |
| HL043PA2 | | 5 | – | S | S | S | S | S | S |
| HL078PA1 | | 1 | – | S | S | S | S | S | S |
| HL086PA1 | IB | 8 | – | S | S | S | S | S | S |
| HL082PA1 | | 8 | – | S | S | S | S | S | S |
| HL110PA2 | | 8 | – | S | S | S | S | S | S |
| HL053PA2 | | 8 | – | S | S | S | S | S | S |
| HL092PA1 | | 8 | – | S | S | S | S | S | S |
| HL110PA1 | | 8 | – | S | S | S | S | S | S |
| HL025PA1 | | 1 | – | S | S | S | S | S | S |
| HL030PA2 | | 3 | – | S | S | S | S | S | S |
| HL063PA2 | | 3 | – | S | S | S | S | S | S |
| HL037PA1 | | 3 | – | S | S | S | S | S | S |
| HL059PA1 | | 16 | – | S | S | S | S | S | S |
| HL059PA2 | | 16 | – | S | S | S | S | S | S |
| HL025PA2 | | 3 | – | S | S | S | S | S | S |
| HL005PA4 | | 3 | – | S | S | S | S | S | S |
| HL067PA1 | | 3 | – | S | S | S | S | S | S |
| HL002PA1 | | 3 | – | S | S | S | S | S | S |
| HL027PA1 | | 3 | – | S | S | S | S | S | S |
| HL046PA1 | | 3 | – | S | S | S | S | S | S |
| HL083PA2 | | 3 | – | S | S | S | S | S | S |
| HL013PA1 | | 3 | – | S | S | S | S | S | S |
| HL050PA1 | | 3 | – | S | S | S | S | S | S |
| HL050PA3 | | 3 | – | S | S | S | S | S | S |
| HL087PA1 | | 3 | – | S | S | S | S | S | S |
| HL087PA3 | | 3 | – | S | S | S | S | S | S |
| KPA171202 | | 1 | – | S | >$10^4$ | S | >$10^4$ | >$10^5$ | S |
| HL030PA1 | | 1 | – | >$10^4$ | S | S | S | >$10^2$ | S |
| HL050PA2 | II | 1 | – | S | S | S | S | >$10^4$ | S |
| HL060PA1 | | 2 | + | S | S | S | S | S | S |
| HL082PA2 | | 2 | + | S | S | S | S | S | S |
| HL001PA1 | | 2 | + | S | >$10^7$ | S | S | >$10^7$ | S |
| HL106PA1 | | 2 | + | S | S | S | S | S | S |
| ATCC 11828 | | 2 | + | S | S | S | S | S | S |
| HL110PA3 | | 6 | + | S | S | S | S | S | S |
| HL110PA4 | | 6 | + | S | S | S | S | S | S |
| HL042PA3 | | 6 | + | S | >$10^6$ | >$10^6$ | S | >$10^7$ | >$10^5$ |
| HL037PA2 | — | *P. humerusii* | – | S | S | S | S | S | S |
| HL037PA3 | | *P. humerusii* | – | S | S | S | S | S | S |
| HL044PA1 | | *P. humerusii* | – | S | S | S | >$10^3$ | S | S |
| HL078PG1 | — | *P. granulosum* | | >$10^7$ | >$10^7$ | >$10^7$ | >$10^7$ | >$10^7$ | >$10^7$ |

| | PHL1125N00 | PHL037Z02 | PHL085N00 | PHL115M02 | PHL085M01 | PHL114L00 | PHL073M02 | PHL010M04 | PHL066M04 |
|---|---|---|---|---|---|---|---|---|---|
| HL036PA1 | S | S | S | S | S | S | S | S | S |
| HL036PA2 | S | S | S | S | S | S | S | S | S |
| HL036PA3 | S | S | S | S | S | S | S | S | S |
| HL046PA2 | S | S | S | S | S | S | S | S | S |
| HL002PA3 | S | S | S | S | S | S | S | S | S |
| HL002PA2 | S | S | S | S | S | S | S | S | S |
| HL005PA2 | S | S | S | S | S | S | S | S | S |
| HL005PA3 | S | S | S | S | S | S | S | S | S |
| HL020PA1 | S | S | S | S | S | S | S | S | S |
| HL027PA2 | S | S | S | S | S | S | S | S | S |
| HL100PA1 | S | S | S | S | S | S | S | S | S |

TABLE 13-continued

Host range and specificity of *P. acnes* phages

| | | | | | | | | | |
|---|---|---|---|---|---|---|---|---|---|
| HL087PA2 | S | S | S | S | S | S | S | S | S |
| HL013PA2 | S | S | S | S | S | S | S | S | S |
| HL063PA1 | S | S | S | S | S | S | S | S | S |
| HL072PA1 | S | S | S | S | S | S | S | S | S |
| HL072PA2 | S | S | S | S | S | S | S | S | S |
| HL106PA2 | S | S | S | S | S | S | S | S | S |
| HL099PA1 | S | S | S | S | S | S | S | S | S |
| HL083PA1 | S | S | S | S | S | S | S | S | S |
| HL038PA1 | S | S | S | S | S | S | S | S | S |
| HL074PA1 | S | S | S | S | S | S | S | S | S |
| HL005PA1 | S | S | S | S | S | S | S | S | S |
| HL056PA1 | S | S | S | S | S | S | S | S | S |
| HL053PA1 | S | S | S | S | S | S | S | S | S |
| HL045PA1 | S | S | S | S | S | S | S | S | S |
| HL007PA1 | S | S | S | S | S | S | S | S | S |
| HL096PA1 | S | S | S | S | S | S | S | S | S |
| HL043PA1 | S | S | S | S | S | S | S | S | S |
| HL043PA2 | S | S | S | S | S | S | S | S | S |
| HL078PA1 | S | S | S | S | S | S | S | S | S |
| HL086PA1 | S | S | S | S | S | S | S | S | S |
| HL082PA1 | S | S | S | S | S | S | S | S | S |
| HL110PA2 | S | S | S | S | S | S | S | S | S |
| HL053PA1 | S | S | S | S | S | S | S | S | S |
| HL092PA1 | S | S | S | S | S | S | S | S | S |
| HL110PA1 | S | S | S | S | S | S | S | S | S |
| HL025PA1 | S | S | S | S | S | S | S | S | S |
| HL030PA2 | S | S | S | S | S | S | S | S | S |
| HL063PA2 | S | S | S | S | S | S | S | S | S |
| HL037PA1 | S | S | S | S | S | S | S | S | S |
| HL059PA1 | S | S | S | S | S | S | S | S | S |
| HL059PA2 | S | S | S | S | S | S | S | S | S |
| HL025PA2 | S | S | S | S | S | S | S | S | S |
| HL005PA4 | S | S | S | S | S | S | S | S | S |
| HL067PA1 | S | S | S | S | S | S | S | S | S |
| HL002PA1 | S | S | S | S | S | S | S | S | S |
| HL027PA1 | S | S | S | S | S | S | S | S | S |
| HL046PA1 | S | S | S | S | S | S | S | S | S |
| HL083PA2 | S | S | S | S | S | S | S | S | S |
| HL013PA1 | S | S | S | S | S | S | S | S | S |
| HL050PA1 | S | S | S | S | S | S | S | S | S |
| HL050PA3 | S | S | S | S | S | S | S | S | S |
| HL087PA1 | S | S | S | S | S | S | S | S | S |
| HL087PA3 | S | S | S | S | S | S | S | S | S |
| KPA171202 | $>10^7$ | $>10^3$ | $>10^4$ | $>10^4$ | $>10^4$ | $>10^4$ | $>10^4$ | $>10^5$ | $>10^7$ |
| HL030PA1 | $>10^3$ | $>10^3$ | $>10^3$ | $>10^3$ | $>10^2$ | $>10^3$ | $>10^4$ | $>10^5$ | $>10^4$ |
| HL050PA2 | S | S | S | S | S | S | S | S | S |
| HL060PA1 | S | S | S | S | S | S | S | S | S |
| HL082PA2 | S | S | S | S | S | S | S | S | S |
| HL001PA1 | S | S | S | S | S | $>10^6$ | S | S | S |
| HL106PA1 | S | S | S | S | S | S | S | S | S |
| ATCC 11828 | S | S | S | S | S | S | S | S | S |
| HL110PA3 | S | S | S | S | S | S | S | S | S |
| HL110PA4 | S | S | S | S | S | S | S | S | S |
| HL042PA3 | S | $>10^7$ | $>10^6$ | $>10^7$ | S | $>10^7$ | $>10^7$ | $>10^7$ | $>10^7$ |
| HL037PA2 | S | S | S | S | S | S | S | S | S |
| HL037PA3 | S | S | S | S | S | S | S | S | S |
| HL044PA1 | $>10^4$ | $>10^3$ | S | $>10^2$ | S | S | S | S | $>10^2$ |
| HL078PG1 | $>10^7$ | $>10^7$ | $>10^7$ | $>10^7$ | $>10^7$ | $>10^7$ | $>10^7$ | $>10^7$ | $>10^7$ |

S susceptible
10' fold increase in resistance

Strains in the IB-3 lineage show resistance against most of the tested phages. Therefore, patients with those strains may not benefit as much from phage therapy. SEQ ID NOs 55-81 include four unique genomic sequences for strains in the IB-3 lineage and for several other strains, such as IB-3-s1 (IB-3 and SK187), IB-3-s2 (IB-3 and HL025PA1), IB-3-s3 (IB-3 and HL201PA1), IB-3-s4 (IB-3 and HL201PA1). The sequence similarities range from 95% to 100%. Primers targeting these sequences can be used to estimate and predict the effectiveness of phage therapy.

Figure 26:
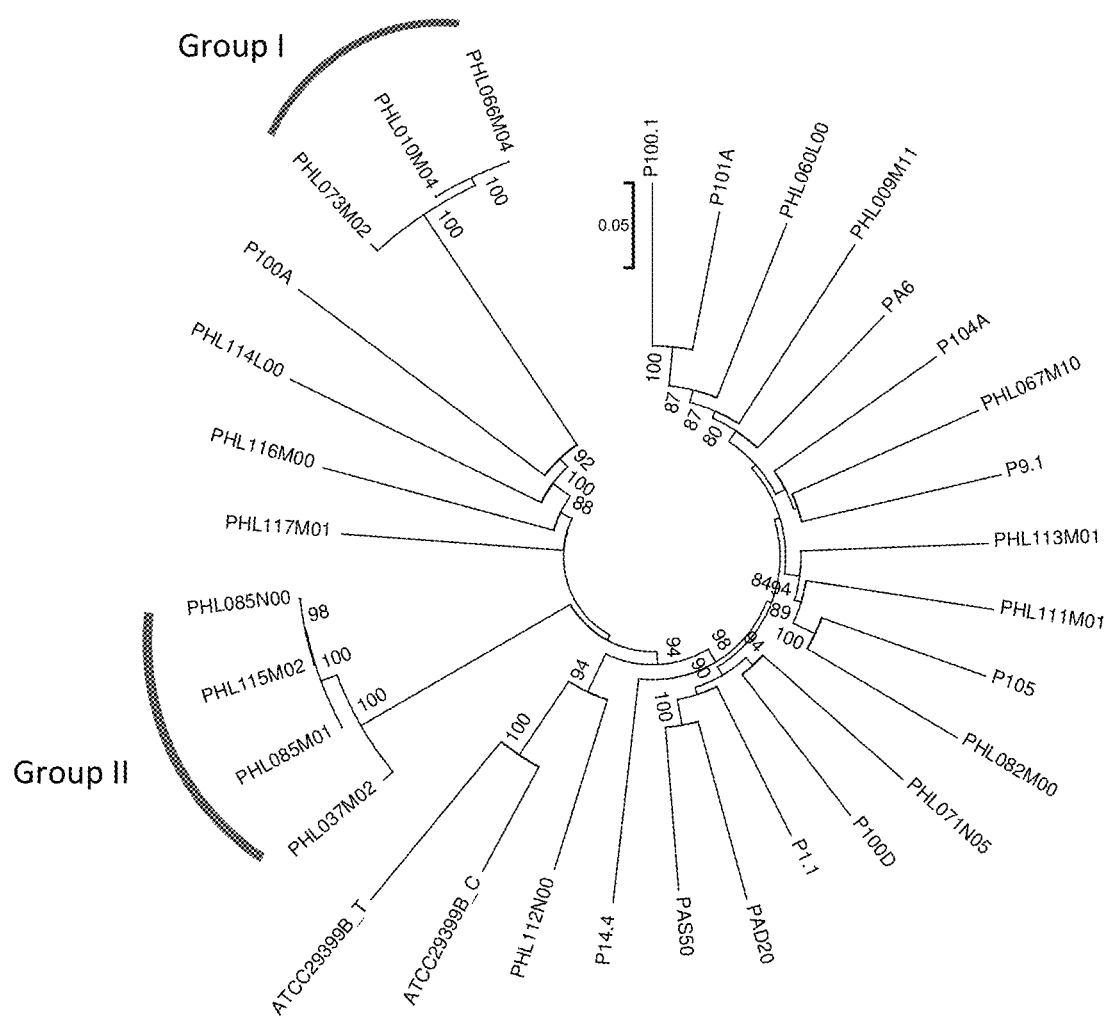
FIG. 26 shows the evolutionary relationships/phylogenetic tree of 32 phages.
Figure 27:
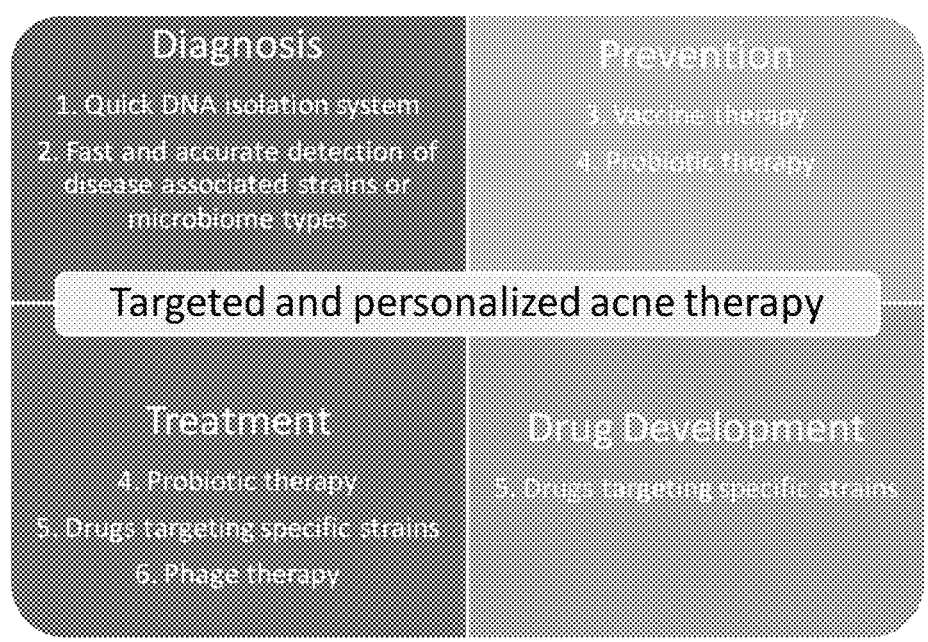
FIG. 27 shows a diagram of the methods of the invention for the diagnosis and personalization of therapy for acne.
Figure 28:
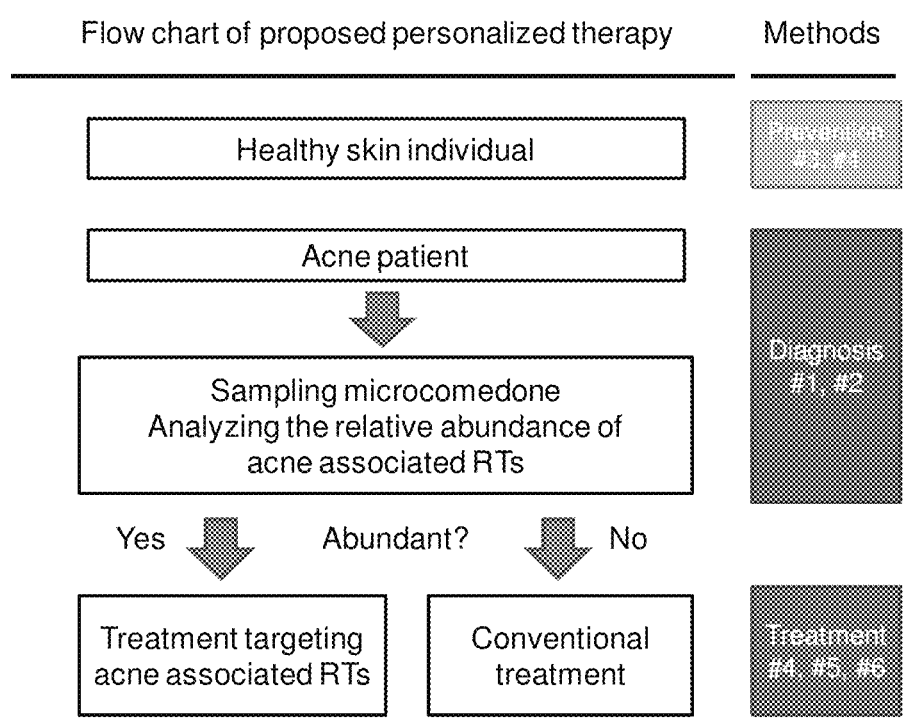
FIG. 28 shows a flow chart of the methods of the invention for the diagnosis and personalization of therapy for acne.

FIG. 26 shows the phylogenetic tree of the 32 phages including the 18 sequenced phages. There are phage strains highly similar to each other, such as the ones in Groups I and II. This suggests that the same phages can be found in different individuals and supports that a particular phage strain can be used as a common treatment agent for different individuals. SEQ ID NOs 33-50 reflect the genome sequences of the 18 sequenced phages, including the 15 phages shown in Table 13.

Potential Therapeutic Phage for Patients with Microbiome Type I Include:
PHL113M01, PHL111M01, PHL082M00, PHL060L00, PHL067M10, PHL071N05, PHL112N00, PHL037M02, PHL085N00, PHL115M02, PHL085M01, PHL114L00, PHL073M02, PHL010M04, and PHL066M04.

Potential Therapeutic Phage for Patients with Microbiome Type I with IB-3 Strain Include:
PHL082M00 and PHL071N05.

Potential Therapeutic Phage for Patients with Microbiome Type II Include:
PHL113M01, PHL060L00, PHL112N00, and PHL085M01.

Potential Therapeutic Phage for Patients with Microbiome Type III or Dominant RT8 Include:
PHL113M01, PHL111M01, PHL082M00, PHL060L00, PHL067M10, PHL071N05, PHL112N00, PHL037M02, PHL085N00, PHL115M02, PHL085M01, PHL114L00, PHL073M02, PHL010M04, and PHL066M04.

Potential Therapeutic Phage for Patients with Microbiome Type IV Include:
PHL113M01, PHL111M01, PHL082M00, PHL060L00, PHL067M10, PHL071N05, PHL112N00, PHL037M02, PHL085N00, PHL115M02, PHL085M01, PHL114L00, PHL073M02, PHL010M04, and PHL066M04.

Potential Therapeutic Phage for Patients with Microbiome Type V Include:
PHL113M01, PHL111M01, PHL082M00, PHL060L00, PHL067M10, PHL071N05, PHL112N00, PHL037M02, PHL085N00, PHL115M02, PHL085M01, PHL114L00, PHL073M02, PHL010M04, and PHL066M04.

Specific Interactions Between *Propionibacterium humerusii* and *P. acnes* Phages Some of the *P. acnes* phage strains can lyse a closely related *Propionibacterium* species, *P. humerusii*, which has been hypothesized to be associated with infection in prostheses. *P. acnes* phage strains that can lyse *P. humerusii* strains can be potentially used as a therapeutic agent for *P. humerusii* associated diseases.

Potential Therapeutic Phage for *P. humerusii* Associated Diseases Include:
PHL113M01, PHL111M01, PHL082M00, PHL067M10, PHL071N05, PHL085N00, PHL085M01, PHL114L00, PHL073M02, and PHL010M04. ORFs in Phage Genomes That Show Identity of 85% or Less to Their PA6 Homolog

| phase_gene name | nucleotide differences | percent difference relative to PA6 | PA6 ORF length |
|---|---|---|---|
| PA6_gp10 | | | 372 |
| PHL113M01_gp9 | 56 | 0.849462366 | |
| PHL112N00_gp9 | 58 | 0.838709877 | |
| PHL114L00_gp10 | 60 | 0.838709677 | |
| PHL010M04_gp11 | 56 | 0.849462366 | |
| PHL082M00_gp10 | 60 | 0.838709677 | |
| PA6_gp19 | | | 747 |
| PHL114L00_gp19 | 120 | 0.83935743 | |
| PHL010M04_gp20 | 138 | 0.814261044 | |
| PHL055M04_gp20 | 138 | 0.814261044 | |
| PHL073M02_gp20 | 138 | 0.814261044 | |
| PA6_gp44 | | | 309 |
| PHL060L00_gp47 | 83 | 0.731391586 | |
| PHL056M04_gp43 | 75 | 0.757281553 | |
| PHL056M04_gp43 | 74 | 0.760517799 | |
| PHL073M02_gp43 | 74 | 0.760517799 | |
| PHL067M10_gp43 | 74 | 0.760517799 | |
| PHL082N00_gp43 | 66 | 0.786407767 | |
| PA6_gp33 | | | 357 |
| PHL115M02_gp37 | 54 | 0.848739456 | |
| PHL085M02_gp32 | 54 | 0.848739456 | |
| PHL037M02_gp31 | 54 | 0.848739456 | |
| PHL085N00_gp32 | 54 | 0.848739456 | |
| PA6_gp45 | | | 183 |
| PHL111M02_gp44. | 33 | 0.819672131 | |
| PA6_gp21 | | | 402 |
| PHL112N00_gp20 | 71 | 0.823383085 | |
| PHL010M02_gp22 | 85 | 0.788557214 | |
| PHL056M02_gp22 | 84 | 0.791044776 | |
| PHL073M02_gp22 | 78 | 0.805970149 | |
| PHL071N05_gp21 | 61 | 0.848258786 | |
| PHL087M10_gp22 | 63 | 0.843285582 | |
| PHL115M02_gp26 | 65 | 0.838308455 | |
| PHL085M01_gp22 | 65 | 0.838308458 | |
| PHL037M02_gp21 | 65 | 0.838308455 | |
| PHL085M00_gp22 | 65 | 0.838308458 | |
| PA6_gp40 | | | 228 |
| PHL111M01_gp41 | 37 | 0.837719288 | |
| PHL080L00_gp42 | 37 | 0.837719288 | |
| PHL112N00_gp39 | 54 | 0.763157885 | |
| PHL113M01_gp43 | 38 | 0.833333333 | |
| PHL114L00_gp40 | 40 | 0.824562404 | |
| PHL010M04_gp40 | 50 | 0.780702754 | |
| PHL066M04_gp40 | 50 | 0.780702754 | |
| PHL073M02_gp40 | 50 | 0.780702754 | |
| PHL071N06_gp39 | 39 | 0.828847358 | |
| PHL067M10_gp40 | 37 | 0.837719288 | |
| PHL115M02_gp45 | 43 | 0.811403509 | |
| PHL085M01_gp40 | 43 | 0.811403509 | |
| PHL037M02_gp39 | 43 | 0.811403509 | |
| PHL085N00_gp40 | 43 | 0.811403509 | |
| PHL082M00_gp39 | 42 | 0.815789474 | |
| PA6_gp22_23 | | | 504 |
| PHL114L00_gp22 | 187 | 0.628958254 | |
| PHL010M04_gp23 | 110 | 0.781746032 | |
| PHL066M04_gp23 | 110 | 0.781746032 | |
| PHL073M02_gp23 | 110 | 0.781746032 | |
| PHL067M10_gp23 | 186 | 0.630952383 | |
| PA6_gp29 | | | 567 |
| PHL060L00_gp30 | 88 | 0.844797178 | |
| PHL112N00_gp27 | 105 | 0.814814815 | |
| PHL114L00_gp28 | 98 | 0.827160494 | |
| PA6_gp35 | | | 471 |
| PHL114L00_gp33 | 76 | 0.838641189 | |
| PA6_gp41 | | | 540 |
| PHL111M02_gp42 | 109 | 0.798188145 | |
| PHL060L00_gp43 | 104 | 0.807407407 | |
| PHL112N00_gp40 | 118 | 0.781481481 | |
| PHL113M01_gp44 | 107 | 0.801851852 | |
| PHL114L00_gp41 | 124 | 0.77037037 | |
| PHL071N05_gp40 | 110 | 0.796296296 | |
| PHL067M10_gp41 | 119 | 0.77962963 | |
| PHL115M02_gp46 | 112 | 0.792592593 | |
| PHL085M02_gp41 | 112 | 0.792592593 | |
| PHL037M02_gp40 | 112 | 0.792592593 | |
| PHL085N00_gp41 | 112 | 0.792592593 | |
| PHL082M00_gp40 | 111 | 0.794444444 | |
| PA6_gp47 | | | 180 |
| PHL115M02_gp50 | 35 | 0.80555556 | |
| PHL085M02_gp44 | 35 | 0.80555556 | |
| PHL037M02_gp44 | 35 | 0.80555556 | |
| PHL111M02_gp45 | 43 | 0.781111111 | |
| PHL071N05_gp44.1 | 32 | 0.822222222 | |
| PHL114L00_gp45.1 | 38 | 0.788888889 | |
| PHL113M01_gp47 | 31 | 0.827777778 | |
| PHL085M00_gp45 | 55 | 0.805555556 | |
| PA6_gp24 | | | 393 |
| PHL114L00_gp23 | 75 | 0.809160305 | |
| PHL010M04_gp24 | 66 | 0.832061069 | |
| PHL066M04_gp24 | 66 | 0.832061069 | |
| PHL073M02_gp24 | 66 | 0.832061069 | |
| PHL067M10_gp24 | 61 | 0.844783715 | |
| PHL115M02_gp29 | 65 | 0.834505598 | |
| PHL085M01_gp24 | 65 | 0.834505598 | |
| PHL037M02_gp23 | 65 | 0.834505598 | |
| PHL085N00_gp24 | 65 | 0.834505598 | |
| PA6_gp30 | | | 564 |
| PHL111M02_gp29 | 115 | 0.796099291 | |
| PHL113M01_gp31 | 105 | 0.813829787 | |
| PHL082M00_gp20 | 118 | 0.794326241 | |
| PA6_gp18 | | | 264 |
| PHL112N00_gp17 | 40 | 0.848484848 | |
| PHL082M00_gp18 | 41 | 0.84469697 | |
| PA6_gp37 | | | 948 |

-continued

| phase_gene name | nucleotide differences | percent difference relative to PA6 | PA6 ORF length |
|---|---|---|---|
| PHL112N00_gp34 | 168 | 0.82278481 | |
| PHL114L00_gp35 | 163 | 0.828059072 | |
| PA6_gp36 | | | 411 |
| PHL111M01_gp36 | 80 | 0.805352798 | |
| PHL112N00_gp33 | 76 | 0.815085158 | |
| PHL113M01_gp38 | 82 | 0.800486618 | |
| PHL114L00_gp34 | 86 | 0.790754258 | |
| PHL101M04_gp35 | 82 | 0.800486618 | |
| PHL066M04_gp35 | 82 | 0.800486618 | |
| PHL073M02_gp35 | 82 | 0.800486618 | |
| PHL071N05_gp34 | 82 | 0.800486618 | |
| PHL115M02_gp40 | 68 | 0.834549878 | |
| PHL085M01_gp35 | 68 | 0.834549878 | |
| PHL037M02_gp34 | 68 | 0.834549878 | |
| PHL085N00_gp35 | 68 | 0.834549878 | |
| PHL082M00_gp34 | 85 | 0.793187348 | |

Example 9—Drug Development

Based on the foregoing, it is now known that some *P. acnes* strains are associated with acne. Therefore, at the time of diagnosis, it will be useful for dermatologists to know which strains are dominant on the skin of the patient. In order to do this, at first one needs to extract bacterial DNA from the skin sample of the patient. The method/kit to isolate bacterial DNA from the skin for downstream analysis detailed above can be implemented in practice. After bacterial DNA is extracted, the fast and accurate detection/diagnosis method/kit to identify the microbiome type of the patients, detailed above, can be implemented for diagnosis. Once the microbiome type of the patient is diagnosed, several approaches can be used to treat the patient.

For example, if the patient has microbiome types IV or V, or is dominated by *P. acnes* RT10 strains, it is less likely antibiotic treatment would succeed, because these strains are antibiotic resistant. These patients should be treated using other therapies, such as retinoids or the methods. In the case that the patient has the virulent ribotypes, including RT4, RT5, and RT8, drugs targeting specifically to RT4, RT5, and RT8, can be used. For example, small molecules, antisense molecules, siRNA, biologics, antibodies, or combinations thereof targeting the genetic elements and biological pathways unique to the *P. acnes* strains associated with acne, detailed above, can be used.

Example 10—Additional Therapies

In the case that the dominant *P. acnes* strains in the patient do not harbor a set of CRISPR/Cas, additional treatment of phage therapy based on the foregoing can be used. For example, bacteriophage-based strain-specific therapy to treat acne can be employed. An alternative treatment strategy is to balance the relative abundance of the *P. acnes* strains by promoting the growth of health-associated strains. The strains associated with health can be used as probiotics. These can be topical creams, solutions, or other cosmetic products.

For prevention purposes, vaccine can be developed against virulent strains of *P. acnes*.

Longitudinal studies determine whether the microbiome types change over time and whether certain strains persist on subjects after treatment.

Inoculation experiments, inoculating virulent and healthy strains, determine whether *P. acnes* strain population changes.

Specific interactions between *P. acnes* strains and phages may be studied.

Immune responses in human cells against different strains of *P. acnes* may also be measured.

The following publications are incorporated herein by reference in their entireties for all purposes, as are all other publications referenced herein and the

SEQUENCE LISTING

E. Grice et al., 324 Science 1190-1192 (2009).

SEQUENCE LISTING

The patent contains a lengthy sequence listing. A copy of the sequence listing is available in electronic form from the USPTO web site (https://seqdata.uspto.gov/?pageRequest=docDetail&DocID=US11692229B2). An electronic copy of the sequence listing will also be available from the USPTO upon request and payment of the fee set forth in 37 CFR 1.19(b)(3).

What is claimed is:

1. A method for treating an individual suffering from acne, comprising: administering to the individual an effective amount of a probiotic that comprises at least one strain of *P. acnes* that is associated with healthy or normal skin based on its 16S rDNA.

2. The method according to claim 1, wherein said strain is an RT6 strain.

3. The method according to claim 1, wherein said strain has at least 95% homology to SEQ ID NO:51, SEQ ID NO:52, SEQ ID NO:53, or SEQ ID NO:54.

4. The method according to claim 3, wherein said strain has at least 99% homology to SEQ ID NO:51, SEQ ID NO:52, SEQ ID NO:53, or SEQ ID NO:54.

5. A method for treating an individual suffering from acne, comprising: administering to the individual an effective amount of a metabolite produced by a strain of *P. acnes* that is associated with healthy or normal skin, wherein said metabolite is selected from the group consisting of bacterial culture supernatant, cell lysate, proteins, nucleic acids, lipids, and other bacterial molecules.

6. The method according to claim 5, wherein said strain is an RT6 strain.

7. The method according to claim 5, wherein said strain has at least 95% homology to SEQ ID NO:51, SEQ ID NO:52, SEQ ID NO:53, or SEQ ID NO:54.

8. The method according to claim 7, wherein said strain has at least 99% homology to SEQ ID NO:51, SEQ ID NO:52, SEQ ID NO:53, or SEQ ID NO:54.

* * * * *